(12) United States Patent
Tang

(10) Patent No.: US 11,040,100 B2
(45) Date of Patent: *Jun. 22, 2021

(54) RAPID AND PROLONGED IMMUNOGIC THERAPEUTIC

(71) Applicant: Altimmune, Inc, Gaithersburg, MD (US)

(72) Inventor: De-Chu C Tang, Plano, TX (US)

(73) Assignee: Altimmune Inc., Gaithersburg, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/926,704

(22) Filed: Jul. 12, 2020

(65) Prior Publication Data

US 2020/0338184 A1 Oct. 29, 2020

Related U.S. Application Data

(63) Continuation of application No. 16/206,211, filed on Nov. 30, 2018, which is a continuation of application No. 14/862,322, filed on Sep. 23, 2015, now Pat. No. 10,183,069, which is a continuation-in-part of application No. 13/426,037, filed on Mar. 21, 2012, now Pat. No. 9,175,310.

(60) Provisional application No. 61/568,054, filed on Dec. 7, 2011, provisional application No. 61/454,819, filed on Mar. 21, 2011.

(51) Int. Cl.
| | |
|---|---|
| *A61K 39/235* | (2006.01) |
| *A61K 39/215* | (2006.01) |
| *A61K 39/07* | (2006.01) |
| *C12N 7/00* | (2006.01) |
| *A61K 9/00* | (2006.01) |
| *A61K 39/00* | (2006.01) |
| *A61K 39/12* | (2006.01) |
| *A61K 39/145* | (2006.01) |
| *A61K 39/155* | (2006.01) |
| *A61K 39/39* | (2006.01) |

(52) U.S. Cl.
CPC .......... *A61K 39/215* (2013.01); *A61K 9/0043* (2013.01); *A61K 39/00* (2013.01); *A61K 39/07* (2013.01); *A61K 39/12* (2013.01); *A61K 39/145* (2013.01); *A61K 39/155* (2013.01); *A61K 39/235* (2013.01); *A61K 39/39* (2013.01); *C12N 7/00* (2013.01); *A61K 2039/5254* (2013.01); *A61K 2039/5256* (2013.01); *A61K 2039/541* (2013.01); *A61K 2039/543* (2013.01); *A61K 2039/545* (2013.01); *A61K 2039/58* (2013.01); *A61K 2039/70* (2013.01); *C12N 2710/10034* (2013.01); *C12N 2710/10043* (2013.01); *C12N 2760/16134* (2013.01)

(58) Field of Classification Search
CPC ............ C12N 15/86; C12N 2810/6018; C12N 2710/10371; C12N 15/861; A61K 39/215; A61K 48/00; A61K 39/235; A61K 2039/5252; A61K 39/155; A61K 2039/543; A61K 2039/5254; A61K 2039/58; A61K 39/00; A61K 2039/541; A61K 9/0043; A61P 31/20; A61P 37/04

See application file for complete search history.

(56) References Cited

U.S. PATENT DOCUMENTS

| | | | |
|---|---|---|---|
| 5,578,308 A | 11/1996 | Capiau et al. | |
| 5,597,727 A | 1/1997 | Kohama et al. | |
| 5,679,647 A | 10/1997 | Carson et al. | |
| 5,683,700 A | 11/1997 | Charles et al. | |
| 5,877,159 A | 3/1999 | Powell et al. | |
| 6,114,148 A | 9/2000 | Seed et al. | |
| 6,348,450 B1 | 2/2002 | Tang et al. | |
| 6,716,823 B1 * | 4/2004 | Tang | A61K 39/001182 514/44 R |
| 6,787,351 B2 * | 9/2004 | Chen | C12N 15/86 435/320.1 |
| 6,841,381 B1 | 1/2005 | Robinson et al. | |

(Continued)

FOREIGN PATENT DOCUMENTS

| | | |
|---|---|---|
| AU | 2005201381 A1 | 4/2005 |
| CA | 2528067 C | 8/2015 |

(Continued)

OTHER PUBLICATIONS

CDC on line report, published on Feb. 15, 2020.*
(NCBI Bookshelf, A service of the National Library of Medcine, National Institute of Health, Medical Biology, 4th edition, Edited by Baron S, chapter 67, p. 1-7 , Adenovirus by Walter Doeifier, 1996, The University of Texas Medical Branch at Galveston, 1996).*
Cohen, et al. "Attenuated Nontoxinogenic and Nonencapsulated Recombinant Bacillus Anthracis Spore Vaccines Protect Against Anthrax" Infection and Immunity, 2000, 68(8):4549-4558.

(Continued)

*Primary Examiner* — Bao Q Li
(74) *Attorney, Agent, or Firm* — Koren Anderson; Duane Morris LLP

(57) ABSTRACT

The present invention shows that intranasal administration of E1/E3-defective adenovirus particles may confer rapid and broad protection against viral and bacterial pathogens in a variety of disease settings. Protective responses lasted for many weeks in a single-dose regimen in animal models. When a pathogen-derived antigen gene was inserted into the E1/E3-defective adenovirus genome, the antigen-induced protective immunity against the specific pathogen was elicited before the adenovirus-mediated protective response declined away, thus conferring rapid, prolonged, and seamless protection against pathogens. In addition to E1/E3-defective adenovirus, other bioengineered non-replicating vectors encoding pathogen-derived antigens may also be developed into a new generation of rapid and prolonged immunologic-therapeutic (RAPIT).

11 Claims, 20 Drawing Sheets

Specification includes a Sequence Listing.

(56) References Cited

U.S. PATENT DOCUMENTS

| | | | |
|---|---|---|---|
| 8,865,182 | B2 | 10/2014 | Mayall et al. |
| 9,175,310 | B2 | 11/2015 | Tang |
| 9,452,209 | B2 | 9/2016 | Ballou et al. |
| 9,605,275 | B2 * | 3/2017 | Tang .................. A61K 39/00 |
| 9,855,328 | B2 | 1/2018 | Tang et al. |
| 10,131,695 | B2 | 11/2018 | Garcia-Sastre et al. |
| 10,183,060 | B2 | 1/2019 | Schreiber et al. |
| 2002/0051791 | A1 | 5/2002 | Galloway et al. |
| 2003/0091579 | A1 | 5/2003 | Manns et al. |
| 2005/0239701 | A1 | 10/2005 | Baker et al. |
| 2006/0223742 | A1 | 10/2006 | Salazar |
| 2007/0003576 | A1 | 1/2007 | Gambotto et al. |
| 2008/0187557 | A1 | 8/2008 | Sambhara et al. |
| 2009/0175897 | A1 | 7/2009 | Tang et al. |
| 2009/0291472 | A1 | 11/2009 | Lu et al. |
| 2010/0008947 | A1 | 1/2010 | Tikoo |
| 2010/0183673 | A1 | 7/2010 | Balint et al. |
| 2011/0081375 | A1 | 4/2011 | Tucker |
| 2015/0071964 | A1 | 3/2015 | Tang |

FOREIGN PATENT DOCUMENTS

| | | |
|---|---|---|
| WO | WO-1997/016532 A1 | 5/1997 |
| WO | WO-1998/020734 A1 | 5/1998 |
| WO | WO-2001/19968 A1 | 3/2001 |
| WO | WO-2003/040305 A2 | 5/2003 |
| WO | WO-2003/070920 A1 | 8/2003 |
| WO | WO-2006/063101 A2 | 1/2007 |
| WO | WO-2006/113214 A2 | 5/2007 |
| WO | WO-2006/127956 A2 | 10/2007 |
| WO | WO-2010/037027 A2 | 4/2010 |
| WO | WO-2019/195626 A1 | 10/2019 |

OTHER PUBLICATIONS

Grandvalet, et al. "Identification of Genes Involved in the Activation of the Bacillus Thuringiensis inhA Metalloprotease Gene At the Onset of Sporulation" Microbiology, 2001,147:1805-1813.

Guttmann, et al. "Phenotypic and Genotypic Comparisons of 23 Strains From the Bacillus Cereus Complex for A Selection of Known and Putative B. Thuringiensis Virulence Factors" FEMS Microbiology Letters, 2000,188:7-13.

Huang, et al. "Identification of Bacillus Anthracis Proteins Associated With Germination and Early Outgrowth by Proteomic Profiling of Anthrax Spores" Proteomics, 2004,4:2653-2661.

Huang, et al. "Proteomics Reveals That Proteins Expressed During the Early Stage of Bacillus Anthracis Infection Are Potential Targets for the Development of Vaccines and Drugs" Geno. Prot. Bioinfo. 2004, 2(3):143-151.

Jedrzejas, "The Structure and Function of Novel Proteins of Bacillus Anthracis and Other Spore Forming Bacteria: Development of Novel Prophylactic and Therapeutic Agents" Critical Reviews in Biochemistry and Molecular Biology, 2002, 37(5):339-373.

Jedrzejas, Three-Dimensional Structure and Molecular Mechanism of Novel Enzymes of Spore-Forming Bacteria, Wed. Sci. Monit, 2002, 8(8):RA183-190.

Keitel et al. "Recombinant protective antigen 102 (rPA102): profile of a second-generation anthrax vaccine" Expert Rev. Vaccines, 2006, 5(4):417-430.

Leppla et al. "Development of an improved vaccine for anthrax" The Journal of Clinical Investigation, 2002,110(2):141-144.

Lovgren, et al. "Molecular Characterization of Immune Inhibitor A, A Secreted Virulence Protease From Bacillus Thuringiensis" Molecular Microbiology, 1990,4(12):2137-2146.

Mock, et al. "Anthrax" Annu. Rev. Microbiol., 2001, vol. 55: 647-71.

Murakami, et al., "A Single Short Stretch of Homology Between Adenoviral Vector and Packaging Cell Line Can Give Rise to Cytopathic Effect-Inducing, Helper-Dependent E1-Positive Particles" Human Gene Therapy, 2002,13:909-920.

Pitt et al., "In vitro correlate of immunity in a rabbit model of inhalational anthrax*" Vaccine, 2001,19:4768-4773.

Price et al, "Protection against Anthrax Lethal Toxin Challenge by Genetic Immunization with a Plasmid Encoding the Lethal Factor Protein" Infection and Immunity, 2001, 69(7):4509-4515.

Purcell et al. "Dissecting the Role of Peptides in the Immune Response: Theory, Practice and the Application to Vaccine Design" Journal of Peptide Science, 2003, 9:255-281.

Read, et al. "Comparative Genome Sequencing for Discovery of Novel Polymorphisms in Bacillus Anthracis" Science, 2002, 296:2028-2033.

Read, et al. "The Genome Sequence of Bacillus Anthracis Ames and Comparison to Closely Related Bacteria" Nature, 2003, 423:81-86.

Shi, et al. "Protection against Tetanus by Needle-Free Inoculation of Adenovirus-Vectored Nasal and Epicutaneous Vaccines" Journal of Virology, 2001, 75(23):11474-11482.

Welkos, et al. "In-Vitro Characterization of the Phagocytosis and Fate of Anthrax Spores in Macrophages and the Effects of Anti-PA Antibody" J. Med. Microbiol., 2002, 51:821-831.

Welkos, et al. "The Role of Antibodies to Bacillus Anthracis and Anthrax Toxin Components in Inhibiting the Early Stages of Infection by Anthrax Spores", Microbiology, 2001,147:1677-1685.

Francois et al. "Avian adenovirus CELO recombinants expressing VP2 of infectious bursal disease virus induce protection against bursal disease in chickens" Vaccine, 2004, 22: 2351-2360.

Webster et al. "Efficacy of nucleoprotein and haemagglutinin antigens expressed in fowlpox virus as vaccine for influenza in chickens" Vaccine, 1991, 9: 303-308.

Takahashi et al. "Adenovirus-mediated ectopic expression of Msx2 in even-numbered rhombomeres induces apoptotic elimination of cranial neural crest cells in ovo" Development, 1998, 125: 1627-1635.

Adam et al. "Replication-defective adenovirus type 5 as an in vitro and in vivo gene transfer vector in chickens" J. Gen. Virol., 1995, 76(12):3153-3157.

Ding, et al. "In ovo vaccination with the Eimeria tenella EtMIC2 gene induces protective immunity against coccidiosis" Vaccine, 2005, 23:3733-3740.

Fallaux, et al. "New Helper Cells and Matched Early Region 1-Deleted Adenovirus Vectors Prevent Generation of Replication-Competent Adenoviruses" Human Gene Therapy, 1998, 9(13):1909-1917.

Gao, et al., "Protection of Mice and Poultry From Lethal H5N1 Influenza Virus Through Adenovirus-Based immunization", Journal of Virology, 2006, 80(4): 1959-1964.

He, et al. "A simplified system for generating recombinant adenoviruses" PNAS, 1998, 95:2509-2514.

McGrory, et al. "A simple technique for the rescue of early region I mutations into infectious human adenovirus type 5" Virology, 1988, 163(2):614-617.

Wesley, et al., "Protection of Weaned Pigs by Vaccination With Human Adenovirus 5 Recombinant Viruses Expressing the Hemagglutinin and the Nucleoprotein of H3N2 Swine Influenza Virus", Vaccine 2004, 22:3427-3434.

Park et al., "Mucosal immunity induced by adenovirus-based H5N1 HPAI vaccine confers protection against a lethal H5N2 avian influenza virus challenge", Virology, 2009, 395 (2):182-189.

Tang et al., "Adenovirus as a carrier for the development of influenza virus-free avian influenza vaccines". Expert. Rev. Vaccine, 2009, . 8(4): 469-481.

Gallichan, et al., "Mucosal immunity and Protection after Intranasal Immunization with Recombinant Adenovirus Expressing Herpes Simplex Virus Glycoprotein B" The Journal of Infectious Diseases, 1993, 168:622-629.

Hubbard, et al., "Fate of aerosolized recombinant DNA-produced alpha 1-antitrypsin: use of the epithelial surface if the lower respiratory tract to administer proteins of therapeutic importance" PNAS, 1989, 86:680-684.

J.S. Final Rejection dated Apr. 17, 2017, which issued in U.S. Appl. No. 14/980,874.

European Search Report dated Jul. 3, 2017, which issued during prosecution of corresponding European Application No. EP 17 16 2446.

(56) References Cited

OTHER PUBLICATIONS

Hardy, et al., "Construction of Adenovirus Vectors through Cre-lox Recombination" Journal of Virology, 1997, 71(3):1842-1849.

Huang, et al., "A differential proteome in tumors suppressed by an adenovirus-based skin patch vaccine encoding human carcinoembryonic antigen" Proteomics, 2005, 5(4): 1013-1023.

Imler. "Adenovirus vectors as recombinant viral vaccines" Vaccine, 1995,13(13):1143-1151.

Kodihall, et al. "Cross-Protection among Lethal H5N2 Influenza Viruses Induced by DNA Vaccine to the Hemagglutinin" Journal of Virology, 1997, 71(5):3391-3396.

Lemckert, et al., "Immunogenicity of Heterologous Prime-Boost Regimens Involving Recombinant Adenovirus Serotype 11 (Ad11) and AD35 Vaccine Vectors in the Presence of Anti-Ad5 Immunity" Journal of Virology, 2005, 79(15):9694-9701.

Abe et al., "Baculovirus Induces an Innate Immune Response and Confers Protection from Lethal Influenza Virus Infection in Mice" Journal of Immunology, 2003, 171:1133-1139.

Arevalo et al., "Mucosal vaccination with a multicomponent adenovirus-vector vaccine protects against *Streptococcus pneumonia* infection in the lung" FEMS Immunology & Medical Microbiology, 2009, 55(3):346-351.

Banfalvi et al., "DNA synthesis in vivo and in vitro in *Escherichia coli* irradiated with ultraviolet light", Eur J Biochem, 1987. 162(2):305-9.

Brenner et al., "Heat shock protein-based therapeutic strategies against human immunodeficiency virus type 1 infection", Infect Dis Obstet Gynecol., 1999, 7(I-2):80-90.

Cui et al., "Non-invasive immunization on the skin using DNA vaccine", Curr Drug Deliv., 2006, 3(I):29-35.

Epstein et al., "Protection against multiple influenza A subtypes by vaccination with highly conserved nucleoprotein" Vaccine, 2005, 23(46-47):5404-5410.

Ginsberg et al., "A mouse model for investigating the molecular pathogenesis of adenovirus pneumonia" Proc. Natl. Acad. Sci., 1991, 88(5):1651-1655.

Glenn et al., "Skin immunization made possible by cholera toxin" Nature, 1998, 391:851-852.

Hartman et al., "Adenovirus vector induced Innate Immune responses: Impact upon efficacy and toxicity in gene therapy and vaccine applications" Virus Res., 2008, 132(0):1-14.

He et al., "A simplified system for generating recombinant adenoviruses" Proc. Nat. Acad. Sci. 1998, 95:2509-2514.

Hughes et al., "Molecular evolution of the vertebrate immune system" BioEssays, 1997, 19(9):777.

International Preliminary Report on Patentability dated Sep. 24, 2013 which issued during prosecution of International Application No. PCT/US2012/029927.

Lambe, et al. "Immunity Against Heterosubtypic Influenza Virus Induced by Adenovirus and MVA Expressing Nucleoprotein and Matrix Protein-1" Scientific Reports, 2013, 3{1443):1-8.

Lemiale et al., "Enhanced mucosal immunoglobulin A response of intranasal adenoviral vector human immunodeficiency virus vaccine and localization in the central nervous system" Journal of Virology, 2003, 77(18):10078-10087.

Lou et al. "A protocol for rapid generation of recombinant adenovirus using the AdEasy system" Nature Protocols, 2007, 2(5):1236-1247.

Mikszta et al., "Protective Immunization against Inhalational 1 Anthrax: A Comparison of Minimally Invasive delivery platforms", Journal of Infectious Diseases, 2005, 191(2):278-288.

Mittal et al., "Immunization with DNA, adenovirus or both in biodegradable alginate microspheres: effect of route of inoculation on immune response" Vaccine, 2000, 19(2-3):253-263.

Okada et al., "Intranasal Immunization of a DNA Vaccine with IL-12-and Granulocyte-Macrophage Colony—stimulating factor (GM-CSF)-expressing plasmids in liposomes induces strong mucosal and cell-mediated immune responses against HIV-1 antigens" The Journal of Immunology, 1997, 159(7):3638-3647.

Patel et al., "A Porcine Adenovirus with Low Human Seroprevalence is a Promising Alternative Vaccine Vector to Human Adenovirus 5 in an H5N1 Virus Disease Model" PloS ONE, 2010, 5(12):1-11.

Pittet et al., "Bacterial contamination of the hands of hospital staff during routine patient care", Arch Intern Med., 1999, 159(8):821-6.

Roy et al. "Partial protection against H5N1 influenza in mice with a single dose of a chimpanzee adenovirus vector expressing nucleoprotein" Vaccine, 2007, 25(39-40):6845-6851.

Strid et al., "Disruption of the stratum corneum allows potent epicutaneous immunization with protein antigens resulting in a dominant systemic Th2 response" European Journal of Immunology, 2004, 34(8):2100-2109.

Sullivan et al., "Development of a preventative vaccine for Ebola virus infection in primates" Nature, 2000, 408:605-609.

Supplementary European Search Report dated Aug. 7, 2014, which issued during prosecution of EP Application No. 12 76 0743.

Tang et al., "Recombinant adenovirus encoding the HA gene from swine H3N2 influenza virus partially protects mice from challenge with heterologous virus: A/HK/1/68 (H3N2)*" Archive Virology, 2002, 147:2125-2141.

Torrieri-Dramard et al., "Intranasal DNA Vaccination Induces Potent Mucosal and Systemic Immune Responses and Cross-protective Immunity Against Influenza Viruses" Molecular Therapy, 2011, 19(3):602-611.

Van Kam Pen et al. "Safety and immunogenicity of adenovirus-vectored nasal and epicutaneous influenza vaccines in humans" Vaccine, 2005, 23:1029-1036.

Zakhartchouk et al., "Severe Acute Respiratory Syndrome Coronavirus Nucleocapsid Protein Expressed by an Adenovirus Vector is Phosphorylated and Immunogenic in Mice", Journal of General Virology, 2005, 86:211-215.

Zhang et al., "Topical application of *Escherichia coli*-vectored vaccine as a simple method for eliciting protective immunity" Infect Immun., 2006, 74(6):3607-17.

Zhang, et al., "Enhanced delivery of naked DNA to the skin by non-invasive in vivo electroporation" Biochim Biophys Acta., 2002, 1572(I):I-9.

Zhang et al., "Adenovirus-Vectored Drug-Vaccine Duo as a Rapid-Response Tool for Conferring Seamless Protection against Influenza" PLoS ONE, 2011, 6(7):I-8.

Altimmune Corporate Presentation Aug. 2020.

Altimmune Launches Clinical Trial of T-COVIDTM, an Investigational Intranasal Immune Modulator for the Treatment of Patients with Early COVID-19 Jun. 1, 2020 https://ir.altimmune.com/news-releases/news-release-details/altimmune-launches-clinical-trial-t-covidtm-investigational.

NasoVAX in Patients With Early Coronavirus Infectious Disease 2019 (COVID-19) https://clinicaltrials.gov/ct2/show/study/NCT04442230?term=altimmune&draw=2&rank=2#contacts.

U.S. Appl. No. 14/870,570, Targets and Compositions for Use in Decontamination, Immunprophylaxis, and Post-Exposure Therapy Against Anthrax, filed Sep. 30, 2015, Granted, U.S. Pat. No. 9,968,667.

U.S. Appl. No. 15/978,618, Targets and Compositions for Use in Decontamination, Immunprophylaxis, and Post-Exposure Therapy Against Anthrax, filed May 14, 2018, Pending, US 2019-0046630.

U.S. Appl. No. 13/426,037, Rapid and Prolonged Immunogic Therapeutic, filed Mar. 21, 2012, Granted, U.S. Pat. No. 9,175,310.

U.S. Appl. No. 14/143,104, Rapid and Prolonged Immunogic Therapeutic, filed Dec. 30, 2013, Granted, U.S. Pat. No. 9,605,275.

U.S. Appl. No. 14/862,322, Rapid and Prolonged Immunogic Therapeutic, filed Sep. 23, 2015, Granted, U.S. Pat. No. 10,183,069.

U.S. Appl. No. 16/206,211, Rapid and Prolonged Immunogic Therapeutic, filed Nov. 30, 2018, Pending, US 2019-0134178.

U.S. Appl. No. 16/926,703, Rapid and Prolonged Immunogic Therapeutic, filed Jul. 11, 2020, Pending, Not yet published.

U.S. Appl. No. 16/840,723, Broad and Long-Lasting Influenza Vaccine, filed Apr. 6, 2020, Pending, Not yet published.

* cited by examiner

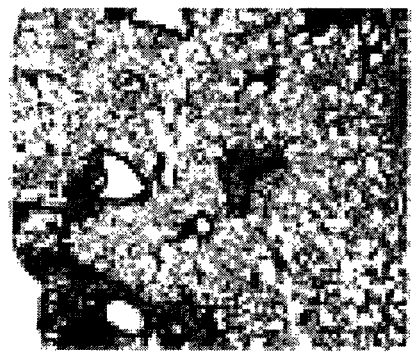
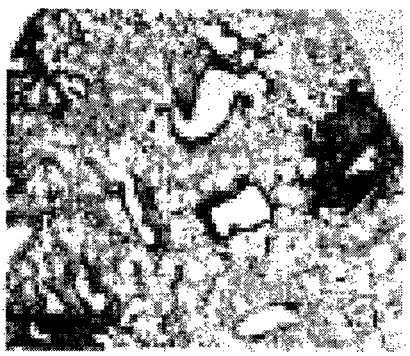
FIGS. 6A-D

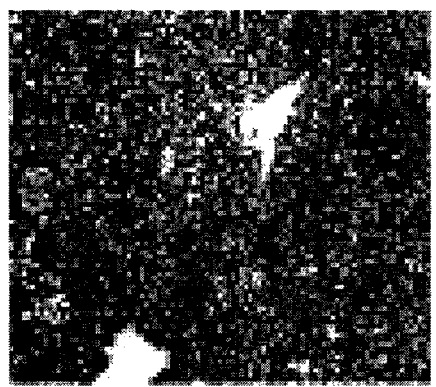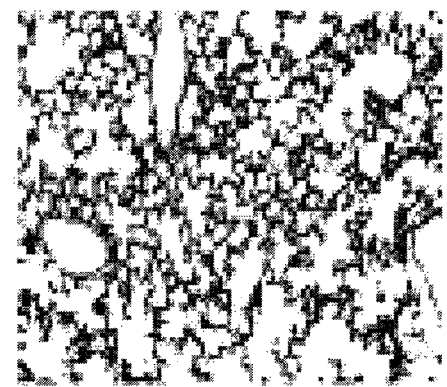
FIGS. 6E-H

A
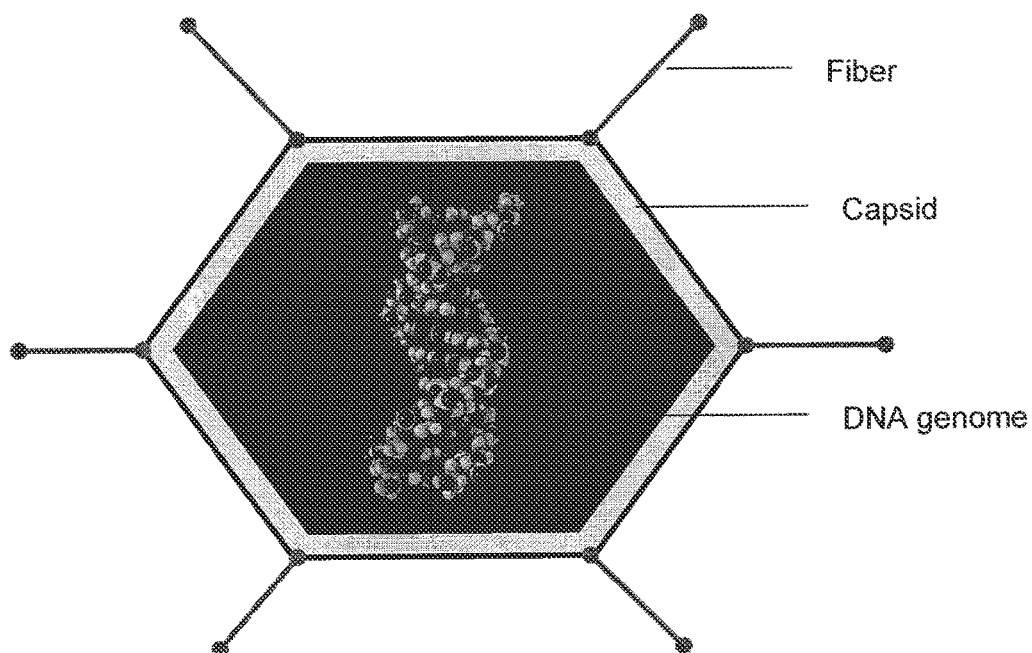
B
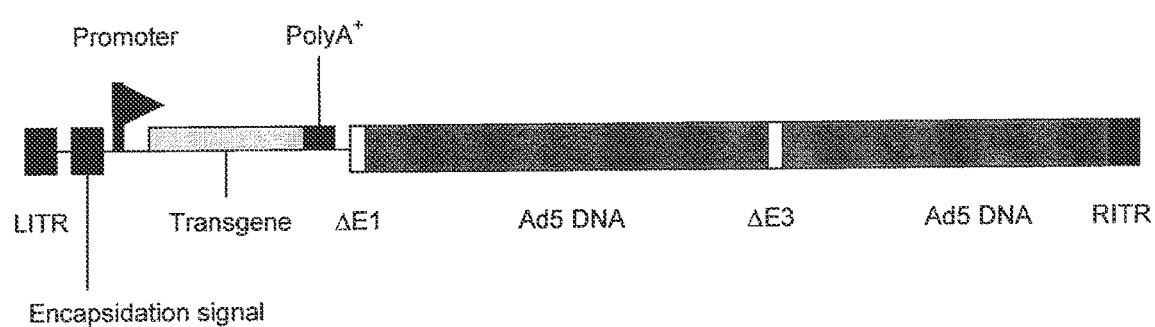
FIG. 9

RAPID AND PROLONGED IMMUNOGIC THERAPEUTIC

RELATED APPLICATIONS AND INCORPORATION BY REFERENCE

This application is a continuation of U.S. application Ser. No. 16/206,211 filed 30 Nov. 2018, which is a continuation of U.S. application Ser. No. 14/862,322 filed 23 Sep. 2015, which is a continuation in part of U.S. application Ser. No. 13/426,037 filed 21 Mar. 2012, which claims priority to U.S. provisional patent application Ser. Nos. 61/454,819 filed 21 Mar. 2011 and 61/568,054 filed 7 Dec. 2011.

Reference is made to U.S. Pat. Nos. 6,348,450, 6,706,693, 6,716,823 and 7,524,510, US Patent Publication Nos. 20030045492, 20030125278, 20040009936, 20050271689, 20070178115, 20090175897 and 20110268762 and U.S. patent application Ser. No. 12/959,791.

The foregoing applications, and all documents cited therein or during their prosecution ("appin cited documents") and all documents cited or referenced in the appin cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FEDERAL FUNDING LEGEND

This invention was supported, in part, by National Institutes of Health grants 2-R44-AI-068285-02, 1-UC1-AI-067198-01 and 1-UC1-A067205-1; a National Institutes of Health contract N01-AI-30063; and a National Institute of Allerby and Infectious Diseases Non-Clinical Evaluation Agreement. The federal government may have certain rights to this invention.

FIELD OF THE INVENTION

The present invention relates generally to the fields of immunology and therapeutic technology. The present invention also relates to methods to elicit rapid-prolonged innate immune responses and uses thereof.

BACKGROUND OF THE INVENTION

The disease-fighting power of immunologics (e.g., vaccines) and therapeutics (e.g., drugs) have been a public health bonanza credited with the worldwide reduction of mortality and morbidity. The goal to further amplify the power of medical intervention requires the development of a new generation of rapid-response immunologics that can be mass produced at low costs and mass administered by nonmedical personnel; as well as a new generation of therapeutics that can confer prolonged protection preferably not impaired by drug resistance. The new immunologics and therapeutics also have to be endowed with a higher safety margin than that of conventional vaccines and drugs.

Use of conventional drugs against microbial pathogens often induces drug resistance over time because microbes constantly evolve under mutational pressure. This invention illustrates that an anti-viral or anti-bacterial state can be rapidly induced in animals following intranasal administration of an E1/E3-defective ($\Delta$E1E3) adenovirus particle by changing the habitat in the airway that impedes the growth of pathogens. Since the adenovirus particle does not directly attack a pathogen, there is little chance for this novel therapeutic to induce drug resistance. Furthermore, the adenovirus-induced anti-pathogen state can persist for many weeks in animals, long enough for overlapping with the induction of protective immunity elicited by a pathogen-derived antigen expressed from the adenovirus, if a pathogen-derived antigen is inserted into the adenovirus genome as a vaccine. It is conceivable that a non-replicating adenovirus particle can be co-administered with other mucosal vaccines as a therapeutic adjunct.

The nonreplicating adenovirus-vectored vaccine holds promise in boosting vaccine coverage because the vector can be rapidly manufactured in serum-free suspension cells in response to a surge in demand. Moreover, preexisting adenovirus immunity does not interfere appreciably with the potency of an adenovirus-vectored nasal vaccine. In addition to human vaccination, animals can also be mass immunized by this class of vectored vaccines.

There is a litany of demands for better vaccines. Although vaccination proves to be the most cost-effective method for the prevention of disease, a sweeping offensive to boost vaccine coverage remains a compelling goal in the movement toward improved public health worldwide. Current vaccines that have been licensed for marketing include killed whole microorganisms, live attenuated microorganisms, microbial extracts, purified or recombinant proteins, DNA vaccines and virus-like particles. Even though many diseases have been defeated by the broad distribution of these vaccines, the goal to generate community (herd) immunity in a wide variety of disease settings remains elusive owing to a number of problems in current vaccination programs.

Specifically, vaccine-associated adverse side effects range from local and systemic inflammatory response, fever, platelet activation, cardiac autonomic dysfunction, anaphylactic reaction (induced by needle injection of certain vaccines) [Salomon M E, Halperin R, Yee J. Evaluation of the two-needle strategy for reducing reactions to DPT vaccination. Am. J. Dis. Child. 141, 796-798 (1987), Lanza G A, Barone L, Scalone G et al. Inflammation-relaxed effects of adjuvant influenza A vaccination on platelet activation and cardiac autonomic function. J. Intern. Med. 269, 118-125 (2011), Jae S Y, Heffernan K S, Park S H et al. Does an acute inflammatory response temporarily attenuate parasympathetic reactivation? Clin. Auton. Res. 20, 229-233 (2010) and Sever J L, Brenner A I, Gale A D et al. Safety of anthrax vaccine: an expanded review and evaluation of adverse events reported to the Vaccine Adverse Event Reporting System (VAERS). Pharmacoepidemiol. Drug Saf. 13, 825-840 (2004)] to the rare occurrence of paralytic poliomyelitis (mediated by ingestion of the oral polio vaccine) [Minor P. Vaccine-derived poliovirus (VDPV): impact on poliomyelitis eradication. Vaccine 27, 2649-2652 (2009)]; myoperi-carditis (induced by inoculation of the Dryvax smallpox vaccine) [Poland G A, Grabenstein J D, Neff J M. The US smallpox vaccination program: a review of a large modern era smallpox vaccination implementation program. Vaccine 23, 2078-2081 (2005)] and Bell's palsy (induced by a bacterial toxin nasal adjuvant) [Lewis I) J, Huo Z, Barnett S et al. Transient facial nerve paralysis palsy) following intranasal delivery of a genetically detoxified mutant of *Escheri-*

*chia coli* heat labile toxin. PLoS ONE 4, e6999 (2009) and Couch R B. Nasal vaccination, *Escherichia coli* enterotoxin, and Bell's palsy. N. Engl. J. Med. 350, 860-861 (2004)].

In 2010, a sudden rise of narcolepsy among vaccinees was reported in a few countries following needle injection of an H1N1 pandemic influenza vaccine containing the squalene adjuvant. Injection of, qualene alone can induce rheumatoid arthritis in animals [Carlson B C, Jansson A M, Larsson A, Bucht A, Lorentzen J C. The endogenous adjuvant squalene can induce a chronic T-cell-mediated arthritis in rats. Am. J. Pathol. 156, 2057-2065 (2000)]. As emerging evidence shows that chronic, low-grade inflammation is associated with cardiovascular disease [Finch C E, Crimmins E M. Inflammatory exposure and historical changes in human life-spans. Science 305, 17361739 (2004)], obesity [Gregor M F, Hotamisligil G S. Inflammatory mechanisms in obesity. Annu. Rev. Immunol. 29, 415-445 (2011)], diabetes [Gregor M F, Hotamisligil G S. Inflammatory mechanisms in obesity. Annu. Rev. Immunol. 29, 415-445 (2011)], cancer [O'Callaghan I) S, O'Donnell I), O'Connell F, O'Byrne K J. The role of inflammation in the pathogenesis of non-small cell lung cancer. J. Thorac. Oncol. 5, 2024-2036 (2010)] and neurological disorder [Witte M E, Geurts J J, de Vries H E, van der Valk P, van Horssen J. Mitochondrial dysfunction: a potential link between neuroinflammation and neurodegeneration? Mitochondrion 10, 411-418 (2010)], vaccine-induced inflammation now needs focused attention.

Whether an acute inflammatory reaction induced by injection of an immunostimulating vaccine-adjuvant complex [Salomon M E, Halperin R, Yee J. Evaluation of the two-needle strategy for reducing reactions to DPT vaccination. Am. J. Dis. Child. 141, 796-798 (1987), Lanza G A, Barone L, Scalone G et al. Inflammation-related effects of adjuvant influenza A vaccination on platelet activation and cardiac autonomic function. J. Intern, Med. 269, 118-125 (2011) and Jae S Y, Heffernan K 5, Park S H et al. Does an acute inflammatory response temporarily attenuate parasympathetic reactivation? Clin. Auton. Res. 20, 229-233 (2010)] could evolve into a chronic, low-grade inflammation and trigger any of these ailments in a subset of vaccinees over time is of paramount importance in public health; however, this potential hazard has not been rigorously investigated. Since the concept of vaccine safety is evolving from 'protection against pathogen-induced diseases' to 'no possibility of inducing adverse consequences', any known extraneous agents, toxicity and residual virulence found in a vaccine would not be allowed, and any possibility of inducing unknown side effects (e.g., inflammation in vital organs) should be avoided.

Mucosal and systemic immune responses are elicited and regulated with a considerable degree of independence and most vaccines have been administered invasively by intramuscular injection, which induces good systemic immunity but often weak mucosal immunity that is crucial in defense against mucosal pathogens (e.g., influenza virus, *Mycobaterium tuberculosis* and HIV) [Gallichan W S, Rosenthal K L. Long-lived cytotoxic T lymphocyte memory in mucosal tissues after mucosal hut not systemic immunization, J. Exp. Med. 184, 1879-1890 (1996) and Saurer L, McCullough K C, Summerfield A. In vitro induction of mucosa-type dendritic cells by all-trans retinoic acid. J. Immunol. 179, 3504-3514 (2007)]. Efficient induction of mucosal immunity usually employs nasal or oral vaccination owing to the unique ability of resident mucosal dendritic cells (DCs) to induce IgA switching and to imprint mucosa-specific homing receptors (e.g., CCR9 and α4β7 integrin) on lymphocytes [Saurer L, McCullough K C, Summerfield A. In vitro induction of mucosa-type dendritic cells by all-trans retinoic acid. J. Immunol. 179,3504-3514 (2007) and Molenaar R, Greuter M. van der Marel A P et al. Lymph node strornal cells support dendritic cell-induced gut-homing of T cells. J. Immunol. 183, 6395-6402 (2009)].

In addition to weak mucosal immunity induced by an injectable vaccine, the syringe needle as a vaccine administration device also poses serious problems through intentional or inadvertent unsterile re-use, needlestick injury, improper waste disposal, as well as limited injection service by licensed medical personnel during a crisis [Tang D C, Van Kampen K R. Toward the development of vectored vaccines in compliance with evolutionary medicine. Expert Rev. Vaccines 7(4), 399-402 (2008)]. Public fear of pointed needles (aichmophobia) plays another role in hindering vaccine coverage. Some people may thus prefer the odds of getting a disease versus the odds of inflicting pain, injury, or death by systemic vaccination. Since the objective of vaccination programs is to reduce the overall probability of infection by generating community (herd) immunity, the mission will be undermined by a hold-off on vaccination owing to public fear of risks. To date, enabling technologies for reversing negative perceptions by developing a new generation of rapid-response vaccines that are safe, efficacious, painless and economical are emerging on the horizon.

Citation or identification of any document in this application is not an admission that such document is available as prior art to the present invention.

SUMMARY OF THE INVENTION

The present invention is based upon the inventor's serendipitous finding that a transgene-free ΔE1E3 adenovirus empty particle or an adenovirus vector encoding a pathogen-derived antigen could elicit a rapid-prolonged-broad protective response against pathogens in a variety of disease settings when intranasally administered.

Without being bound by limitation, Applicant hypothesizes that adenovirus may be involved in activating specific arms of innate immunity that impede growth of respiratory mucosal pathogens.

The present invention relaters to a method of inducing a response in a patient in need thereof which may comprise administering to the patient an adenovirus that is defective or deleted in its E1 and/or E3 regions in an amount effective to induce the response. In an advantageous embodiment, the patient may be a mammal.

In one embodiment, the adenovirus does not contain and express a transgene.

In another embodiment, the adenovirus may contain and express a nucleic acid molecule encoding a gene product. In particular, the adenovirus may comprise an exogenous or heterologous nucleic acid molecule encoding a pathogen-derived gene product that elicits protective immunity. The exogenous or heterologous nucleic acid molecule may encode an epitope of interest. In particular, the exogenous or heterologous nucleic acid molecule may encode one or more influenza virus; respiratory syncytial virus (RSV); *Bacillus anthracia*; or other pathogen-derived epitopes of interest and/or one or more influenza antigens.

In an advantageous embodiment, the adenovirus may be a human adenovirus. In another embodiment, the immune response may be elicited within 24 hours. In another embodiment, the administration results in a protective response from about one day to about 47 days.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIGS. 6A-H depicts Lung histopathology induced by PR8 infection. (A and E) Lung resected from an untreated control mouse (FIG. 3) 19 days post-PR8 challenge. (B and F) Lung resected from a normal Balb/c mouse as a control. (C and G) Lung resected from an AdE/in/−2 mouse (FIG. 3) 19 days post-PR8 challenge; each section is a representative of three mice. (D and H) Lung resected from an AdNC/in/−2 mouse (FIG. 3) 19 days post-PR8 challenge; each section is a representative of three mice. Lung sections were examined on a Zeiss Axioskop2 plus microscope using a 2× (A-D) or a 10× (E-H) objective lens in conjunction with an Axiocam digital camera.

FIG. 9 depicts architecture of adenovirus. (A) Structure of an Ad particle. Ad is an icosahedral, non-enveloped DNA virus. Its tightly coiled DNA genome is packaged inside a hexagonal protein capsid. (B) Layout of the ΔE1E3 Ad5 vector. The ΔE1E3 Ad5 vector has been widely used in a large number of gene therapy as well as vaccine trials. Its high immunogenicity was considered a hurdle for re-administration; however, the problem has been lessened by recent evidence showing that ΔE1E3 Ad5-vectored nasal vaccines can bypass pre-existing Ad.5 immunity. Ad: Adenovirus; LITR: Left inverted terminal repeat; Promoter: A common promoter to drive transgene expression is the cytomegalovirus early promoter; PolyA+; A common polyadenylation site is the SV40 polyadenylation signal; RITR: Right inverted terminal repeat.

Figure 1:
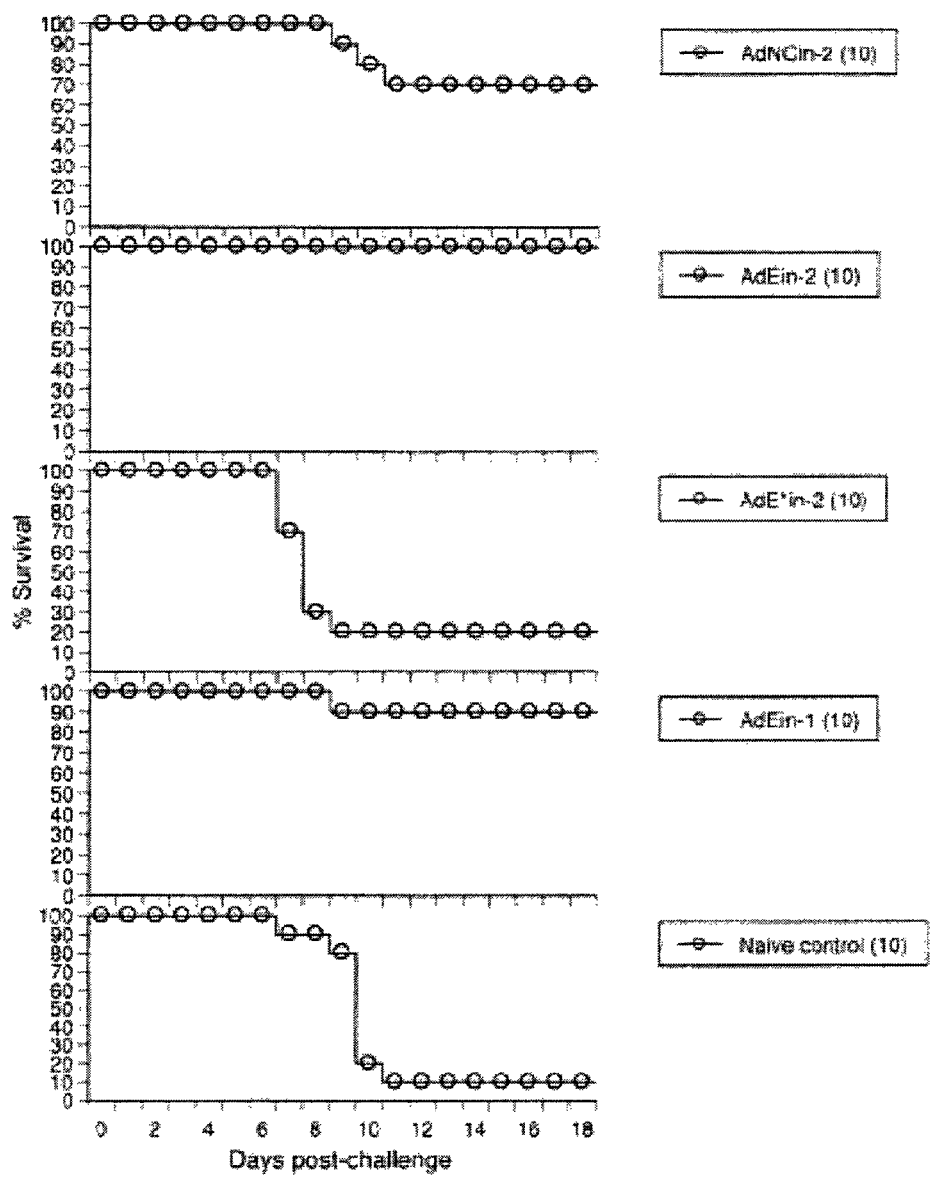
FIG. 1 shows rapid protection of mice against influenza virus challenges by intranasal administration of adenovirus particles.

Also contemplated by the present invention are receptor-binding ligands, recombinant vectors, drug-vaccine compositions, and recombinant adenoviruses that can comprise subviral particles from more than one adenovirus serotype. For example, it is known that adenovirus vectors can display an altered tropism for specific tissues or cell types (Havenga, M. J. E. et al., 2002), and therefore, mixing and matching of different adenoviral capsids, i.e., fiber, or penton proteins from various adenoviral serotypes may be advantageous. Modification of the adenoviral capsids, including fiber and penton can result in an adenoviral vector with a tropism that is different from the unmodified adenovirus. Adenovirus vectors that are modified and optimized in their ability to infect target cells can allow for a significant reduction in the therapeutic or prophylactic dose, resulting in reduced local and disseminated toxicity.

Viral vector gene delivery systems are commonly used in gene transfer and gene therapy applications. Different viral vector systems have their own unique advantages and disadvantages. Viral vectors that may be used to express the pathogen-derived ligand of the present invention include but are not limited to adenoviral vectors, adeno-associated viral vectors, alphavirus vector, herpes simplex viral vector, and retroviral vectors, described in more detail below.

Adenovirus vectors have many characteristics which are ideal for gene delivery, especially delivery into the respiratory tract. Examples of these characteristics include:
(a) ability of adenovirus vectors to transduce both mitotic and postmitotic cells in situ;
(b) existing technology to prepare stocks containing high titers of virus [greater than $10^{12}$ ifu (infectious units) per ml] to transduce cells in situ at high multiplicity of infection (MOI);
(c) inhalation of adenovirus is in compliance with evolutionary medicine (Tang and Van Kampen, 2008);
(d) potency of an intranasally-administered adenovirus vector may not be interfered by preexisting immunity to adenovirus (Hoelscher et al., 2006; Shi et al., 2001; Van Kampen et al., 2005); while not wishing to be bound by theory, this may be attributed to the high efficiency of gene delivery, high level of transgene expression, and high degree of antigen presentation along the mucosal barrier in the respiratory tract;
(e) capability of adenovirus to induce high levels of transgene expression (at least as an initial burst); and
(f) ease with which replication-defective adenovirus vectors can be bioengineered.

Additional general features of adenoviruses are that the biology of the adenovirus is characterized in detail; the adenovirus is not associated with severe human pathology; the adenovirus is extremely efficient in introducing its DNA into the host cell; the adenovirus can infect a wide variety of cells and has a broad host range; the adenovirus can be produced in large quantities with relative ease; and the adenovirus can be rendered replication defective and/or non-replicating by deletions in the early region 1 ("E1") of the viral genome.

Reference is made to U.S. Pat. No. 5,990,091 issued Nov. 23, 1999, Einat et al. or Quark Biotech, Inc., WO 99/60164, published Nov. 25, 1999 from PCT/US99/11066, filed May 14, 1999, Fischer or Rhone Merieux, Inc., WO98/00166, published Jan. 8, 1998 from PCT/US97/11486, filed Jun. 30, 1997 (claiming priority from U.S. application Ser. Nos. 08/675,556 and 08/675,566), van Ginkel et al., J. Immunol 159(2):685-93 (1997) ("Adenoviral gene delivery elicits distinct pulmonary-associated T helper cell responses to the vector and to its transgene"), and Osterhaus et al., Immunobiology 184(2-3):180-92 (1992) ("Vaccination against acute respiratory virus infections and measles in man"), for information concerning expressed gene products, antibodies and uses thereof, vectors for in vivo and in vitro expression of exogenous nucleic acid molecules, promoters for driving expression or for operatively linking to nucleic acid molecules to be expressed, method and documents for producing such vectors, compositions comprising such vectors or nucleic acid molecules or antibodies, dosages, and modes and/or routes of administration (including compositions for nasal administration), inter alia, which can be employed in the practice of this invention; and thus, U.S. Pat. No. 5,990,091 issued Nov. 23, 1999, Einat et al. or Quark Biotech, Inc., WO 99/60164, published Nov. 25, 1999 from PCT/US99/11066, filed May 14, 1999, Fischer or Rhone Merieux, Inc., WO98/00166, published Jan. 8, 1998 from PCT/US97/11486, filed Jun. 30, 1997 (claiming priority from U.S. application Ser. Nos. 08/675,556 and 08/675,566), van Ginkel et al., J. Immunol 159(2):685-93 (1997) ("Adenoviral gene delivery elicits distinct pulmonary-associated T helper cell responses to the vector and to its transgene"), and Osterhaus et al., Immunobiology 184(2-3): 180-92 (1992) ("Vaccination against acute respiratory virus infections and measles in man") and all documents cited or referenced therein and all documents cited or referenced in documents cited in each of U.S. Pat. No. 5,990,091 issued Nov. 23, 1999, Einat et al. or Quark Biotech, Inc., WO 99/60164, published Nov. 25, 1999 from PCT/US99/11066, filed May 14, 1999, Fischer or Rhone Merieux, Inc., WO98/00166, published Jan. 8, 1998 from PCT/US97/11486, filed Jun. 30, 1997 (claiming priority from U.S. application Ser. Nos. 08/675,556 and 08/675,566), van Ginkel et al., J. Immunol 159(2):685-93 (1997) ("Adenoviral gene delivery elicits distinct pulmonary-associated. T helper cell responses to the vector and to its transgene"), and Osterhaus et al., Immunobiology 184(2-3):180-92 (1992) ("Vaccination against acute respiratory virus infections and measles in man") are hereby incorporated herein by reference. Information in U.S. Pat. No. 5,990,091 issued Nov. 23, 1999, WO 99/60164, WO98/00166, van Ginkel et al., J. Immunol 159(2):685-93 (1997), and Osterhaus et al., Immunobiology 184(2-3): 180-92 (1992) can be relied upon for the practice of this invention (e.g., expressed products, antibodies and uses thereof, vectors for in vivo and in vitro expression of exogenous nucleic acid molecules, exogenous nucleic acid molecules encoding epitopes of interest or antigens or therapeutics and the like, promoters, compositions comprising such vectors or nucleic acid molecules or expressed products or antibodies, dosages, inter alia).

It is noted that immunological products and/or antibodies and/or expressed products obtained in accordance with this invention can be expressed in vitro and used in a manner in which such immunological and/or expressed products and/or antibodies are typically used, and that cells that express such immunological and/or expressed products and/or antibodies can be employed in in vitro and/or ex vivo applications, e.g., such uses and applications can include diagnostics, assays, ex vivo therapy (e.g., wherein cells that express the gene product and/or immunological response are expanded in vitro and reintroduced into the host or animal), etc., see U.S. Pat. No. 5,990,091, WO 99/60164 and WO 98/00166 and documents cited therein.

Further, expressed antibodies or gene products that are isolated from herein methods, or that are isolated from cells expanded in vitro following herein administration methods, can be administered in compositions, akin to the administration of subunit epitopes or antigens or therapeutics or antibodies to induce immunity, stimulate a therapeutic response and/or stimulate passive immunity. The quantity to be administered will vary for the patient (host) and condition being treated and will vary from one or a few to a few hundred or thousand micrograms, e.g., 1 µg to 1 mg, from about 100 ng/kg of body weight to 100 mg/kg of body weight per day and preferably will be from 10 pg/kg to 10 mg/kg per day.

A vector can be administered to a patient or host in an amount to achieve the amounts stated for gene product (e.g., epitope, antigen, therapeutic, and/or antibody) compositions. Of course, the invention envisages dosages below and above those exemplified herein, and for any composition to be administered to an animal or human, including the components thereof, and for any particular method of administration, it is preferred to determine therefor: toxicity, such as by determining the lethal dose (LD) and $LD_{50}$ in a suitable animal model e.g., rodent such as mouse; and, the dosage of the composition(s), concentration of components therein and timing of administering the composition(s), which elicit a suitable response, such as by titrations of sera and analysis thereof, e.g., by ELISA and/or seroneutralization analysis, Such determinations do not require undue experimentation from the knowledge of the skilled artisan, this disclosure and the documents cited herein. And, the invention also comprehends sequential administration of inventive compositions or sequential performance of herein methods, e.g., periodic administration of inventive compositions such as in the course of therapy or treatment for a condition and/or booster administration of immunological compositions and/or in prime boost regimens; and, the time and manner for sequential administrations can be ascertained without undue experimentation.

The dosage of the adenovirus of the present invention may be from about $10^6$ ifu. to about $10^{10}$ ifu. The dosage may be about $10^6$ ifu, about $10^7$ ifu, about $10^8$ ifu, about $10^9$ ifu or about $10^{10}$ ifu. In an advantageous embodiment, the dosage is about $10^6$ ifu, about $10^7$ ifu or about $10^8$ ifu.

In a particularly advantageous embodiment, multiple dosages of the adenovirus of the present invention. In a particularly advantageous embodiment, about two doses are administered. In an advantageous embodiment, the doses are administered about 20 days apart, about 25 days apart, about 30 days apart, about 35 days apart, about 40 days apart, about 45 days apart, about 50 days apart, about 55 days apart, about 60 days apart or about 65 days apart. Advantageously, the doses are administered about 40 days apart, about 41 days apart, about 42 days apart, about 43 days apart, about 44 days apart, about 45 days apart, about 46 days apart, about 47 days apart, about 48 days apart, about 49 days apart or about 50 days apart.

Further, the invention comprehends compositions and methods for making and using vectors, including methods for producing gene products and/or immunological products and/or antibodies in vivo and/or in vitro and/or ex vivo (e.g., the latter two being, for instance, after isolation therefrom from cells from a host that has had a non-invasive administration according to the invention, e.g., after optional expansion of such cells), and uses for such gene and/or immunological products and/or antibodies, including in diagnostics, assays, therapies, treatments, and the like. Vector compositions are formulated by adinixin.g the vector with a suitable carrier or diluent; and, gene product and/or immunological product and/or antibody compositions are likewise formulated by admixing the gene and/or immunological product and/or antibody with a suitable carrier or diluent; see, e.g., U.S. Pat. No. 5,990,091, WO 99/60164, WO 98/00166, documents cited therein, and other documents cited herein, and other teachings herein (for instance, with respect to carriers, diluents and the like).

In an advantageous embodiment, the vector expresses a gene encoding an influenza antigen, a RSV antigen, a HIV antigen, a SIV antigen, a HPV antigen, a HCV antigen, a HBV antigen, a CMV antigen or a Staphylococcus antigen. The influenza may be swine influenza, seasonal influenza, avian influenza, H1N1 influenza or H5N1 influenza.

In another advantageous embodiment, the vector expresses a gene which encodes influenza hemagglutinin, influenza nuclear protein, influenza M2, tetanus toxin C-fragment, anthrax protective antigen, anthrax lethal factor, rabies glycoprotein, HBV surface antigen, HIV gp 120, HW gp 160, human carcinoembryonic antigen, malaria CSP, malaria SSP, malaria MSP, malaria pfg, *Mycobacterium tuberculosis* HSP or a mutant thereof.

In an embodiment of the invention, the immune response in the animal is induced by genetic vectors expressing genes encoding antigens of interest in the animal's cells. The antigens of interest may be selected from any of the antigens described herein.

In another embodiment of the method, the animal's cells are epidermal cells. In another embodiment of the method, the immune response is against a pathogen or a neoplasm. In another embodiment of the method, the genetic vector is used as a prophylactic vaccine or a therapeutic vaccine. In another embodiment of the invention, the genetic vector comprises genetic vectors capable of expressing an antigen of interest in the animal's cells. In a further embodiment of the method, the animal is a vertebrate.

With respect to exogenous DNA for expression in a vector (e.g., encoding an epitope of interest and/or an antigen and/or a therapeutic) and documents providing such exogenous DNA, as well as with respect to the expression of transcription and/or translation factors for enhancing expression of nucleic acid molecules, and as to terms such as "epitope of interest", "therapeutic", "immune response", "immunological response", "protective immune response", "immunogenic composition", "immunogenic composition", and "vaccine composition", inter alia, reference is made to U.S. Pat. No. 5,990,091 issued Nov. 23, 1999, and WO 98/00166 and WO 99/60164, and the documents cited therein and the documents of record in the prosecution of that patent and those PCT applications; all of which are incorporated herein by reference. Thus, U.S. Pat. No. 5,990,091 and WO 98/00166 and WO 99/60164 and documents cited therein and documents or record in the prosecution of that patent and those PCT applications, and other documents cited herein or otherwise incorporated herein by reference, can be consulted in the practice of this invention; and, all exogenous nucleic acid molecules, promoters, and vectors cited therein can be used in the practice of this invention. In this regard, mention is also made of U.S. Pat. Nos. 6,004,777, 5,997,878, 5,989,561, 5,976,552, 5,972,597, 5,858,368, 5,863,542, 5,833,975, 5,863,542, 5,843,456, 5,766,598, 5,766,597, 5,762,939, 5,756,102, 5,756,101, 5,494,807.

In another embodiment of the invention, the animal is advantageously a vertebrate such as a mammal, bird, reptile, amphibian or fish; more advantageously a human, or a companion or domesticated or food-producing or feed-producing or livestock or game or racing or sport animal such as a cow, a dog, a cat, a goat, a sheep or a pig or a horse, or even fowl such as turkey, ducks or chicken. In an especially advantageous another embodiment of the invention, the vertebrate is a human.

In another embodiment of the invention, the genetic vector is a viral vector, a bacterial vector, a protozoan vector, a retrotransposon, a transposon, a virus shell, or a DNA vector. In another embodiment of the invention, the viral vector, the bacterial vector, the protozoan vector and the DNA vector are recombinant vectors. In another embodiment of the invention, the immune response is against influenza A. In another embodiment of the invention, the immune response against influenza A is induced by the genetic vector expressing a gene encoding an influenza hetnagglutinin, an influenza nuclear protein, an influenza M2 or a fragment thereof in the animal's cells. In another embodiment of the invention, the genetic vector is selected from the group consisting of viral vector and plasmid DNA.

in another embodiment of the invention, the genetic vector is an adenovirus. In another embodiment of the invention, the adenovirus vector is defective in its E1 region. In another embodiment of the invention, the adenovirus vector is defective in its E3 region. In another embodiment of the invention, the adenovirus vector is defective in its E1 and/or E3 regions. In another embodiment of the invention, the DNA is in plasmid form. In another embodiment of the invention, the contacting step further comprises disposing the genetic vector containing the gene of interest on a delivery device and applying the device having the genetic vector containing the gene of interest therein to the skin of the animal. In another embodiment of the invention, the genetic vector encodes an immunomodulatory gene, as co-stimulatory gene or a cytokine gene. In another embodiment of the invention, the vector has all viral genes deleted. In another embodiment of the invention, the genetic vector induces an anti-tumor effect in the animal. In a further embodiment of the invention, the genetic vector expresses an oncogene, a tumor-suppressor gene, or a tumor-associated gene.

Representative examples of antigens which can be used to produce an immune response using the methods of the present invention include influenza hemagglutinin, influenza nuclear protein, influenza M2, tetanus toxin C-fragment, anthrax protective antigen, anthrax lethal factor, rabies glycoprotein, HBV surface antigen, HIV gp 120, HIV gp 160, human carcinoembryonic antigen, malaria. CSP, malaria SSP, malaria MSP, malaria pfg, and *Mycobacterium tuberculosis* HSP, etc. Most preferably, the immune response produces a protective effect against neoplasms or infectious pathogens.

In another embodiment of the present invention, the vector further contains a gene selected from the group consisting of co-stimulatory genes and cytokine genes. In this method the gene is selected from the group consisting of a GM-CSF gene, a B7-1 gene, a B7-2 gene, an interleukin-2 gene, an interleukin-12 gene and interferon genes.

The recombinant vectors and methods of the present invention can be used in the treatment or prevention of various respiratory pathogens. Such pathogens include, but are not limited to, influenza virus, severe acute respiratory syndrome-associated coronavirus (SARS-CoV), human rhinovirus (HRV), and respiratory syncytial virus (RSV).

In addition, the present invention comprehends the use of more than therapeutic ligand, immunogen or antigen in the vectors and methods disclosed herein, delivered either in separate recombinant vectors, or together in one recombinant vector so as to provide a multivalent vaccine or immunogenic composition that stimulates or modulates immunogenic response to one or more influenza strains and/or hybrids. Further, the present invention encompasses the use of a therapeutic ligand, immunogen or antigen from more than one pathogen in the vectors and methods disclosed herein, delivered either in separate recombinant vectors, or together in one recombinant vector.

Embodiments of the invention that use DNA/adenovirus complexes can have the plasmid DNA complexed with adenovirus vectors utilizing a suitable agent therefor, such as either PEI (polyethylenimine) or polylysine. The adenovirus vector within the complex may be either "live" or "killed" by UV irradiation. The UV-inactivated adenovirus vector as a receptor-binding ligand and an endosomolysis agent for facilitating DNA-mediated transfection (Cotten et al., 1992) may raise the safety margin of the vaccine carrier. The DNA/adenovirus complex is used to transfect epidermal cells of a vertebrate in a non-invasive mode foruse as an immunizing agent.

Genetic vectors provided by the invention can also code for immunomodulatory molecules which can act as an adjuvant to provoke a humoral and/or cellular immune response. Such molecules include cytokines, co-stimulatory molecules, or any molecules that may change the course of an immune response. One can conceive of ways in which this technology can be modified to enhance still further the immunogenicity of antigens.

In terms of the terminology used herein, an immunologically effective amount is an amount or concentration of the genetic vector encoding the gene of interest, that, when administered to an animal, produces an immune response to the gene product of interest.

Various epitopes, antigens or therapeutics may be delivered topically by expression thereof at different concentrations. Generally, useful amounts for adenovirus vectors are at least approximately 100 pfu and for plasmid DNA at least approximately 1 ng of DNA. Other amounts can be ascertained from this disclosure and the knowledge in the art, including documents cited and incorporated herein by reference, without undue experimentation.

The methods of the invention can be appropriately applied to prevent diseases as prophylactic vaccination or treat diseases as therapeutic vaccination.

The vaccines of the present invention can be administered to an animal either alone or as part of an immunological composition.

Beyond the human vaccines described, the method of the invention can be used to immunize animal stocks. The term animal means all animals including humans. Examples of animals include humans, cows, dogs, cats, goats, sheep, horses, pigs, turkey, ducks and chicken, etc. Since the immune systems of all vertebrates operate similarly, the applications described can be implemented in all vertebrate systems.

The present invention also encompasses combinations of vectors, in particular adenovirus vectors. For example, an empty adenovector (E1/E3 deleted with no insert) may be sequentially or simultaneously administered to a patient in need thereof along with another vector, such as an adenovector, which may be E1/E3 deleted with an insert, such as an exogenous gene as herein described. Without being bound by theory, the empty adenovector (E1/E3 deleted with no insert) may initially elicit a rapid immune response wherein a vector expressing an exogeneous gene, such as an antigen or epitope, may elicit an additional protective response.

Although the present invention and its advantages have been described in detail, it should be understood that various changes, substitutions and alterations can be made herein without departing from the spirit and scope of the invention as defined in the appended claims. The present invention will be further illustrated in the following Examples which are given for illustration purposes only and are not intended to limit the invention in any way.

EXAMPLES

Example 1

Adenovirus Particle as a Broad-Spectrum Drug Against Respiratory Pathogens

Although vaccination is an effective approach for preventing infectious diseases when administered weeks or months in advance, it is too slow to protect animals or people who are at immediate risk. An agent capable of reducing the severity of an infection when taken shortly before or after an infection is of paramount importance in public health. Tamiflu (oseltamivir phosphate) and Relenza (zanamivir) have proven effective in preventing influenza virus infections; however, these neuraminidase inhibitors may generate drug-resistant influenza virus strains over time (Poland et al., 2009). Similar to viruses, drug-resistant bacteria are also commonly generated by overuse of drugs (Davies and Davies, 2010). It is thus urgent to develop additional drugs because medical personnel will have the option to use another drug in the pipeline for arresting pathogens when one drug in use is impaired by drug resistance.

Figure 2:
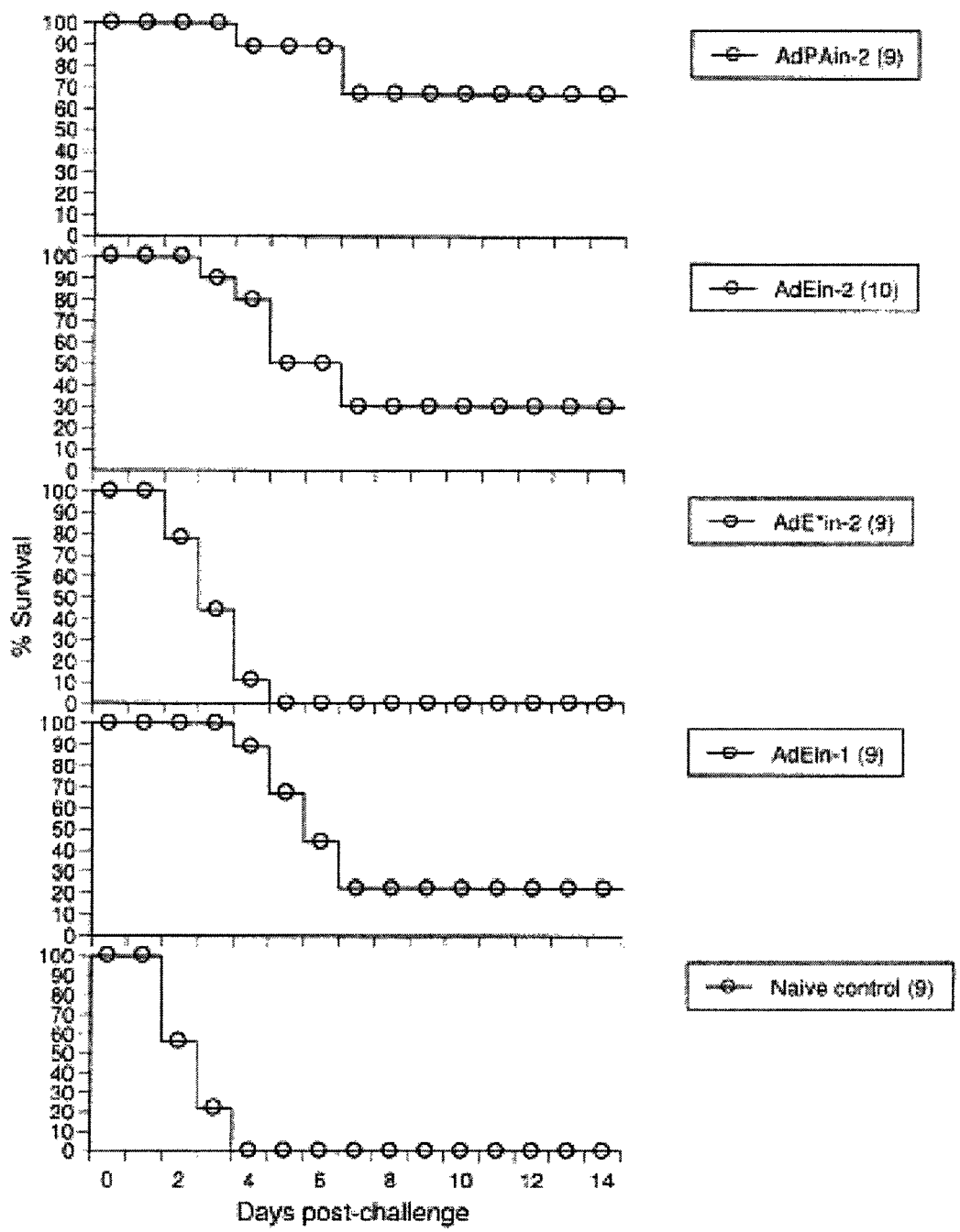
FIG. 2 shows rapid protection of mice against anthrax by intranasal administration of adenovirus particles.
Figure 15:
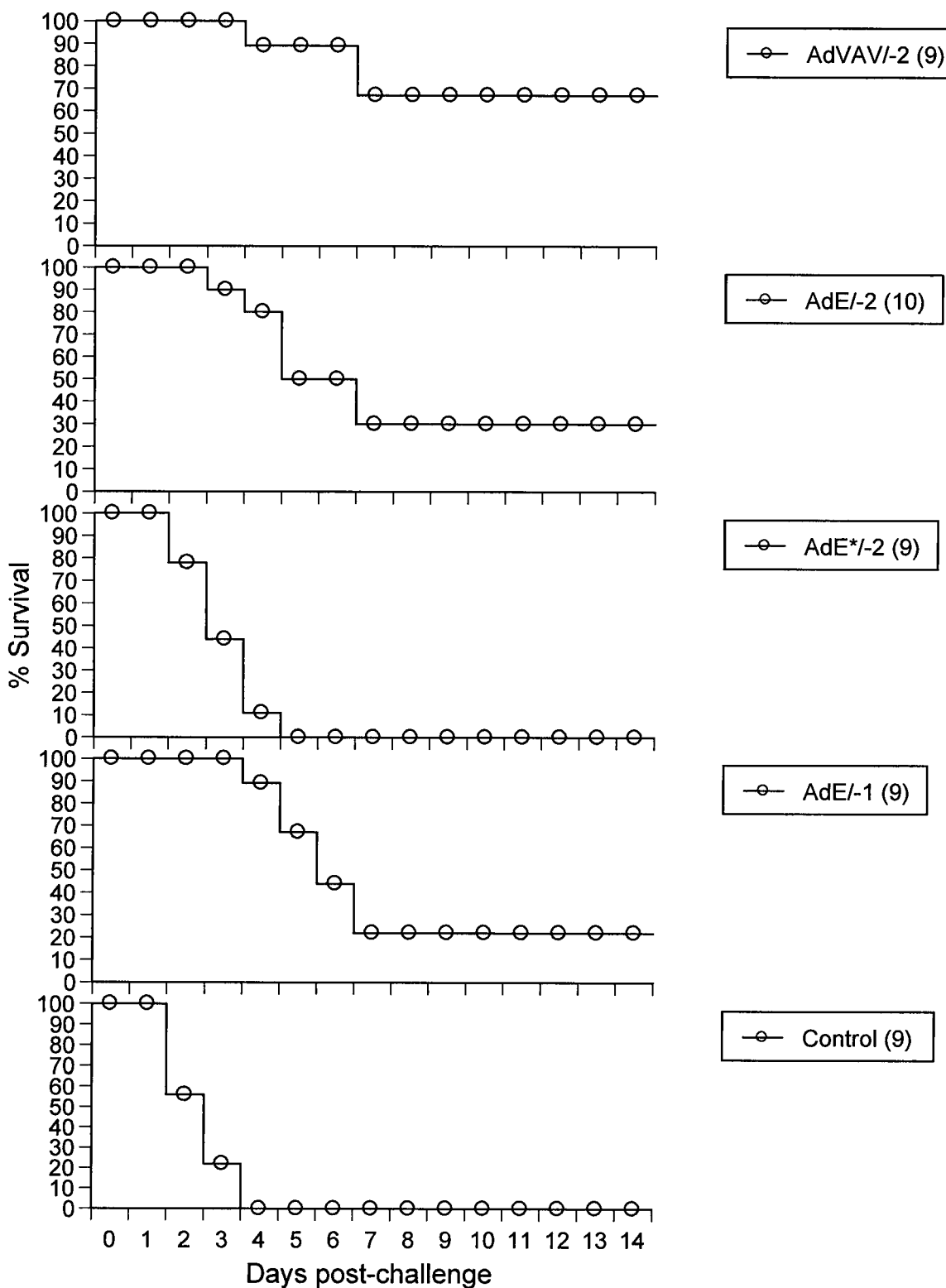

Applicant has demonstrated that intranasal instillation of E1l/3-defective adenovirus (Ad) particles 1-2 days prior to intranasal challenge with a lethal dose of influenza virus could confer rapid protection against influenza in mice (FIG. 1). Applicant has also shown that intranasal administration of Ad 1-2 days prior to intranasal challenge with a lethal dose of *Bacillus anthracia* Sterne spores was also able to protect mice against anthrax (FIGS. 2 and 15). It is conceivable that intranasal administration of Ad rapidly induces an array of reactions that impede growth of other microbes in the respiratory tract.

Since the Ad has been bioengineered into a non-replicating vaccine carrier with an excellent safety profile in animals and humans (Tang et al., 2009), it is conceivable that an Ad vector encoding a pathogen-derived antigen may be developed into a drug vaccine duo (DVD), which is able to confer rapid and broad protection against a variety of pathogens before adaptive immunity is induced; followed by elicitation of pathogen specific protective immunity as a vaccine; in a single package. FIGS. 1 and 2 show that not only the transgene-free Ad backbone (AdE) could confer rapid protection against viruses and bacteria as a drug, but also its counterparts encoding pathogen derived antigens were able to arrest pathogens as a drug.

Methods of FIG. 1. Purified AdNC.H1.1 vectors encoding the HA1 of A/NC/20/99 (H1N1) influenza virus and its transgene-free counterpart (AdE) were administered dropwise in a volume of 0.05 ml into the nostril of each young BALB/c mouse (2 months old) using a mechanical pipet as described (Shi et al., 2001) prior to challenge. One or two days post-Ad administration, mice were challenged intranasally with a lethal dose (0.2 HA units) of the A/PRI8/34 (H1N1) influenza virus and monitored daily for survival.

Results of FIG. 1. Seventy percent of mice (7/10) were protected against a lethal dose of live A/PR/8/34 influenza virus by intranasal instillation of the AdNC.H1.1 vector at a dose of $1.7\times10^8$ infectious units (ifu) 2 days prior to challenge (AdEin−2); 100% of mice (10/10) were protected against influenza by intranasal instillation of the AdE vector at a dose of $1.7\times10^6$ ifu 2 days prior to challenge (AdEin−2); 20% of mice (2/10) were protected against influenza by intranasal instillation of the AdE vector at a dose of $1.7\times10^6$ ifu 2 days prior to challenge (AdE*in−2); 90% of mice (9/10) were protected against influenza by intranasal instillation of the AdE vector at a dose of $1.7\times10^8$ ifu 1 day prior to challenge (AdEin−1); all control mice (Naive control) died within 10 days post-challenge. The data was plotted as % survival versus days after challenge. Numbers in parentheses represent the number of animals in each group.

Significance of FIG. 1. Protection of animals against influenza by intranasal administration of an Ad vector 1 or 2 days prior to live influenza virus challenge shows that the Ad particle is able to rapidly induce an anti-viral state in the respiratory tract. Since Ad vectors encoding influenza virus. HA have been developed into influenza vaccines (Hoelscher et al., 2006; Tang et al, 2009; Van Kampen et al., 2005) and the AdNC.H1.1 vector encoding the A/NC/20/99 HA still conferred rapid protection as an influenza drug before adaptive immunity was elicited, there is compelling evidence that this regimen represents a drug-vaccine duo (DVD) that can confer broad and rapid protection as an anti-viral drug followed by elicitation of protective immunity as an anti-viral vaccine, in a single package.

Methods of FIG. 2. Purified AdPA83 vectors encoding the *Bacillus anthracis* protective antigen and its transgene-free counterpart (AdE) were administered dropwise in a volume of 0.05 ml into the nostril of each young A/J mouse (2 months old) using a mechanical pipet as described (Shi et al., 2001) prior to challenge. One or two days post-Ad administration, mice were challenged intranasally with a lethal dose [$1\times10^5$ colony-forming units (cfu)] of *B. anthracis* Sterne spores and monitored daily for survival.

Results of FIG. 2. Sixty-seven percent of mice (6/9) were protected against a lethal dose of anthrax spores by intranasal instillation of the AdPA.83 vector at a dose of $1.3\times10^8$ ifu 2 days prior to challenge (AdPAin−2); 30% of mice (3/10) were protected against anthrax by intranasal instillation of the AdE vector at a dose of $1.3\times10^8$ ifu 2 days prior to challenge (AdEin−2); no mice (0/9) were protected against anthrax by intranasal instillation of the AdE vector at a dose of $1.3\times10^6$ ifu. 2 days prior to challenge (AdE*in−2); 22% of mice (2/9) were protected against anthrax by intranasal instillation of the AdE vector at a dose of $1.3 \times 10^8$ ifu 1 day prior to challenge (AdEin-1); all control mice (Naive control) died within 4 days post-challenge. The data was plotted as % survival versus days after challenge. Numbers in parentheses represent the number of animals in each group.

Significance of FIG. 2. Protection of animals against anthrax by intranasal administration of an Ad vector 1 or 2 days prior to anthrax spore challenge shows that the Ad particle is able to rapidly induce an anti-bacterial state in the respiratory tract. Since Ad vectors encoding PA have been developed into anthrax vaccines (McConnell et al., 2007) and the AdPA83 vector encoding the PA still conferred rapid protection as an anthrax drug before adaptive immunity was elicited, there is compelling evidence that this regimen represents a drug-vaccine duo (DVD) that can confer rapid protection as an anti-bacterial drug followed by elicitation of protective immunity as an anti-bacterial vaccine, in a single package.

REFERENCES

Davies, J., and Davies, D. (2010). Origins and evolution of antibiotic resistance. Microbiol Mol Bioi Rev 74,417-433.
Hoelscher, M. A., Garg, S., Bangari, D. S., Belser, J. A., Lu, X., Stephenson, I., Bright, R. A., Katz, J. M., Mittal, S. K., and Sambhara, S. (2006). Development of adenoviral-vector-based pandemic influenza vaccine against antigenically distinct human H5N1 strains in mice. Lancet 367,475-481.
McConnell, M. J., Hanna, P. C., and Imeriale, M. J. (2007). Adenovirus-based prime-boost immunization for rapid vaccination against anthrax. Mol Ther 15,203-210.
Poland, G. A., Jacobson, R. M., and Ovsyannikova, I. G. (2009). Influenza virus resistance to antiviral agents: a plea for rational use. Clin Infect Dis 48, 1254.1256.
Shi, Z., Zeng, M., Yang, G., Siegel, F., Cain, L. J., Van Kampen, K. R., Elinets, C. A., and Tang, D. C. (2001). Protection against tetanus by needle-free inoculation of adenovirus-vectored nasal and epicutaneous vaccines. J Virol 75, 11474-11482.
Tang, D. C., Zhang, J., Toro, H., Shi, Z., and Van Kampen, K. A. (2009). Adenovirus as a carrier for the development of influenza virus-free avian influenza vaccines. Expert Rev Vaccines 8, 469-481,
Van Kampen, K. R., Shi, Z., Gao, P., Zhang, J., Foster, K. W., Chen, D. T., Marks, D., Elmets, C. A., and Tang, D. C. (2005), Safety and immunogenicity of adenovirus-vectored nasal and epicutaneous influenza vaccines in humans. Vaccine 23, 1029.1036.

Example 2

Adenovirus-Vectored Drug-Vaccine Duo as a Rapid-Response Tool for Conferring Seamless Protection Against Influenza Few other diseases exert such a huge toll of suffering as influenza. Applicant reports here that intranasal (i.n.) administration of E1/E3-defective (ΔE1E3) adenovirus serotype 5 (Ad5) particles rapidly induced an anti-influenza state as a means of prophylactic therapy which persisted for several weeks in mice. By encoding an influenza virus (IFV) hemagglutinin (HA) HA1 domain, an Ad5-HA1 vector conferred rapid protection as a prophylactic drug followed by elicitation of sustained protective immunity as a vaccine for inducing seamless protection against influenza as a drug-vaccine duo (DVD) in a single package. Since Ad5 particles induce a complex web of host responses, which could arrest influenza by activating a specific arm of innate immunity to impede IFV growth in the airway, it is conceivable that this multi-pronged influenza DVD may escape the fate of drug resistance that impairs the current influenza drugs.

Influenza is a resurging and emerging disease with virtually no possibility of eradicating the causal virus which triggers seasonal as well as pandemic influenza. As a zoonotic disease with the potential to sicken both animals and humans [1], a designer IFV can be rapidly generated by reverse genetics [2] and disseminated by terrorists to ravage agriculture, public health, and economy within a targeted region. Even though this highly contagious and potentially fatal disease has been partially controlled by vaccination, the licensed influenza vaccine is difficult to mass-produce [1] and unable to confer timely as well as broad protection against heterosubtypic IFV strains [3]. Another line of defense against influenza is the use of influenza drugs [e.g., oseltarnivir (Tamiflu); zanamivir (Relenza)]; however, this option is limited by the emergence of drug-resistant IFV due to selection under mutational pressure [4,5].

To develop a rapid-response anti-influenza agent, we serendipitously demonstrated that an Ad5-vectored nasal influenza vaccine could confer rapid protection as a drug-like manner. A replication-competent adenovirus (RCA)-free Ad5 vector encoding pathogen antigens thus potentially can confer seamless protection against mucosal pathogens as a DVD in a wide variety of clinical settings. RCA-free Ad5 vectors can be rapidly mass-produced in serum-free PER.C6 suspension cells; painlessly mass-administered by nasal spray [1]; followed by elicitation of innate as well as adaptive immune responses in the face of pre-existing Ad5 immunity. In the case of an influenza DVD, the chance to generate drug-resistant lFV is minimal since Ad5 particles conceivably induce an anti-influenza state without directly attacking the IFV. In contrast to a live attenuated IFV vaccine (LAIV), an Ad5-vectored DVD is non-replicating and does not reassort with wild IFV. It is expected that nasal spray of an Ad5-vectored influenza. DVD can confer broad protection against heterosubtypic IFV strains for several weeks as a prophylactic drug; followed by elicitation of strain-specific protective immunity as a vaccine for months or even years before the drug induced protection declines away. This novel regimen may add a rapid-response tool to the public health arsenal against influenza and other diseases if the DVD's protective effects should be reproduced in human subjects.

Figure 3A:
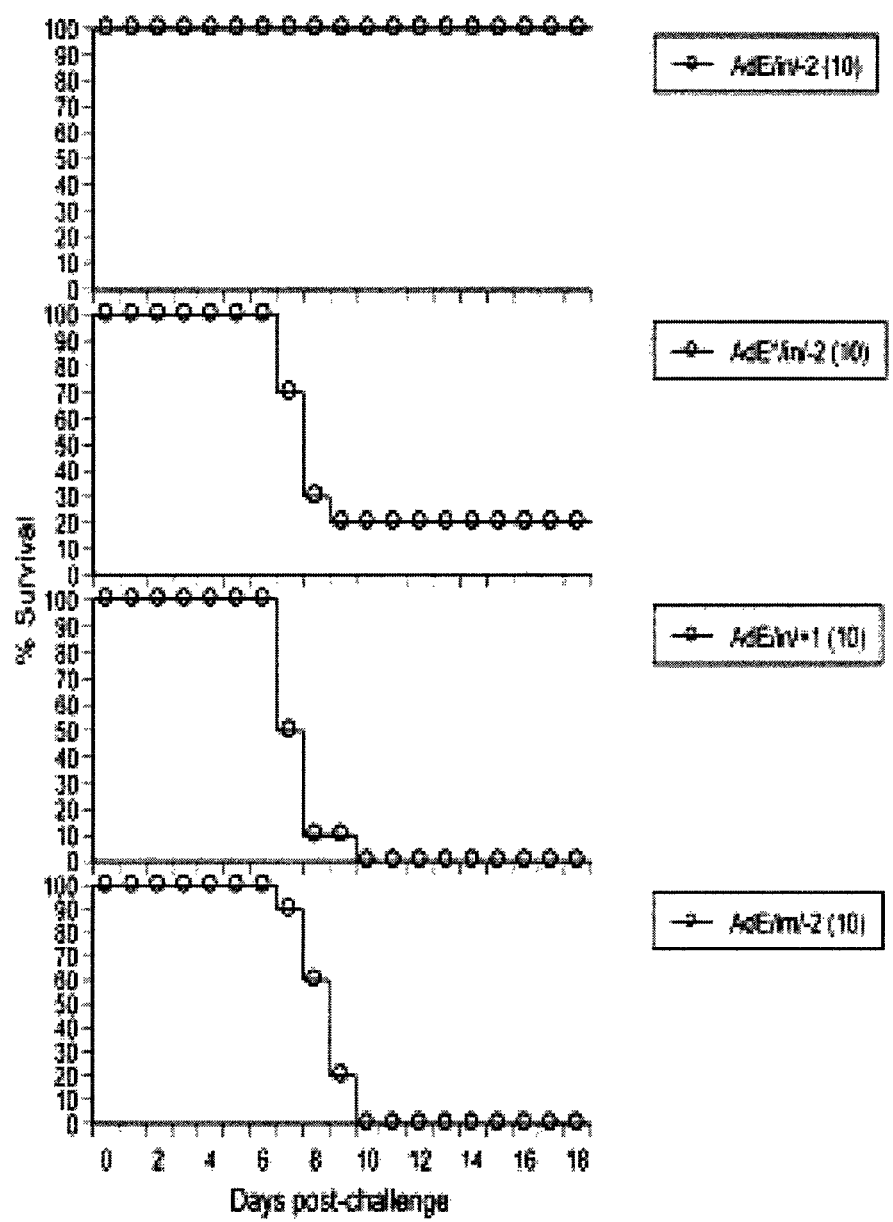
FIGS. 3A and 3B depict prophylactic therapy against lethal challenge by A/PR/8/34 (PR8) in mice. Prophylactic therapy was performed by i.n. administration of Ad5 particles shortly before PR8 challenge. AdE/in/−2 and AdE*/in/−2, i.n. administration of AdE on day −2; AdE*/in/+1, i.n. administration of AdE 1 day post-PR8 challenge; AdE/im/−2, i.m. injection of AdE on day −2; AdNC*/in/−2 and AdNC*/in/−2, i.n. administration of AdNC.H1.1 on day −2; AdNC/im/−2, i.m. injection of AdNC.H1.1 on day −2; untreated control, Balb/c mice without treatment prior to PR8 challenge; all groups were inoculated with AdE or AdNC.H1.1 at a dose of $1.7 \times 6 10^6$ ifu except AdE*/in/−2 and AdNC*/in/−2 groups that received a dose of $1.7 \times 610^6$ ifu; all groups were challenged by i.n. instillation of $4 \times LD_{50}$ of PR8 on day 0; body weights were recorded daily for 18 days post-challenge with 30% body weight loss taken as the disease endpoint; numbers in parentheses represent the number of animals in each group.
Figure 3B:
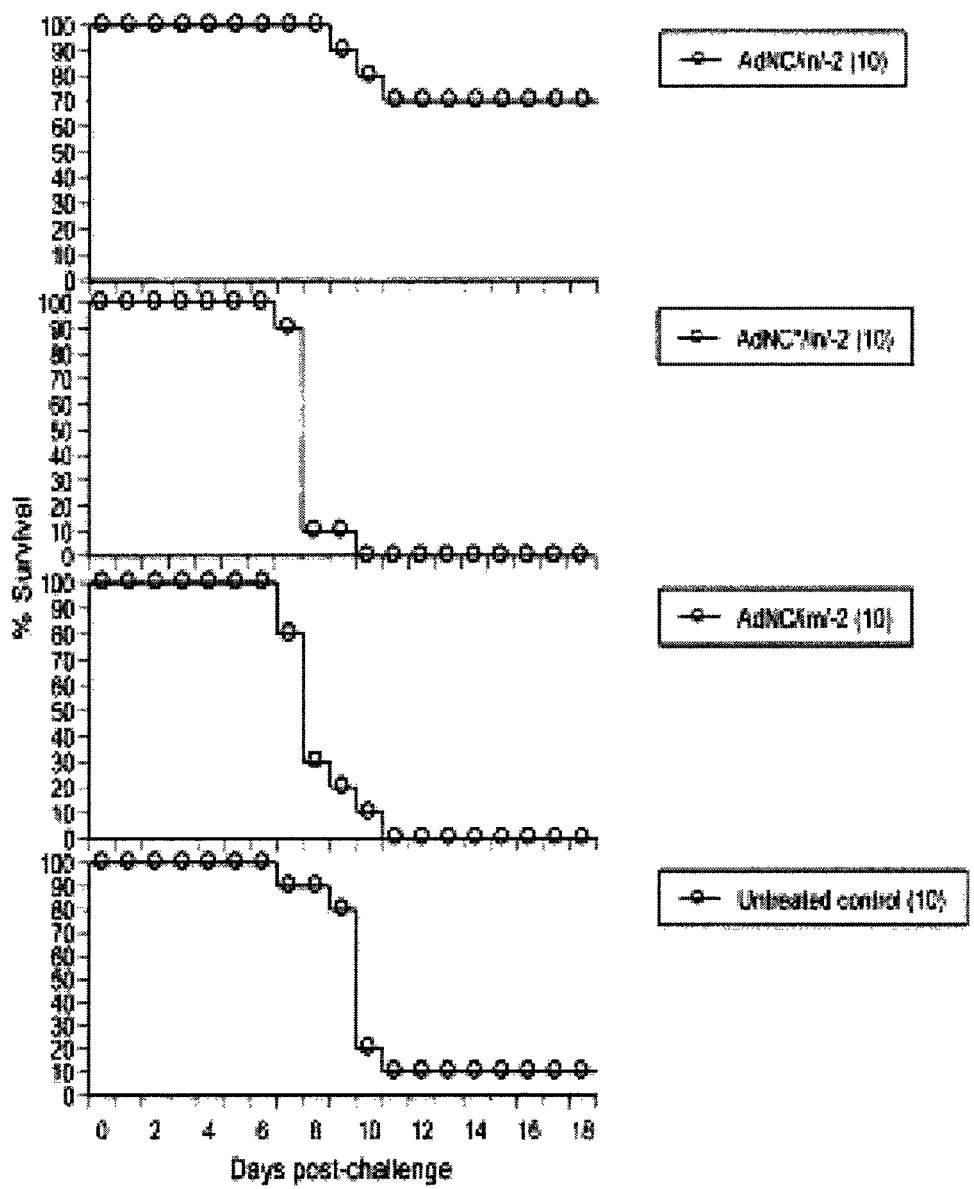

The ΔE1E3 Ad5 particle as an anti-influenza agent. The transgene-free ΔE1E3 Ad5 empty (AdE) particle and its counterpart AdNC.H1.1 encoding the A/New Caledonia/20/99 H1N1 IFV (NC20) HA1 domain were generated in PER.C6 cells as described [1]. As shown in FIG. 3A, i.n. instillation of $1.7 \times 10^8$ infectious units (ifu) of AdE 2 days (day -2) prior to challenge protected 100% (10/10) of mice against a lethal dose of live A/Puerto Rico/8/34 H1N1 IFV (PR8); only 20% (2/10) of the animals were protected when AdE's dose was reduced 100-fold to $1.7 \times 10^6$ ifu; and there was no protection when $1.7 \times 10^8$ ifu of AdE were administered into mice by i.n. instillation 1 day post-PR8 challenge or by i.m. injection on day -2. Insertion of the NC20 HA1 domain into the AdE genome mildly interfered with ΔE1E3 Ad53 s capacity to induce an anti-influenza state as only 70% (7/10) of animals were protected when $1.7 \times 10^8$ ifu of AdNC.H1.1 were i.n. administered into mice on day -2. Similar to AdE, neither i.n. instillation of $1.7 \times 10^6$ ifu nor i.m. injection of $1.7 \times 10^8$ ifu of AdNC.H1.1 conferred any protection against PR8 when administered on day −2 (FIG. 3). The protection afforded by i.n. administration of AdE (p,0.0001) or AdNC.H1.1 (P=0.0077) at a dose of 1.7×10$^8$ ifu on day −2 reached statistical significance when compared to that of the untreated control group (by Logrank tests).

Figure 4A:
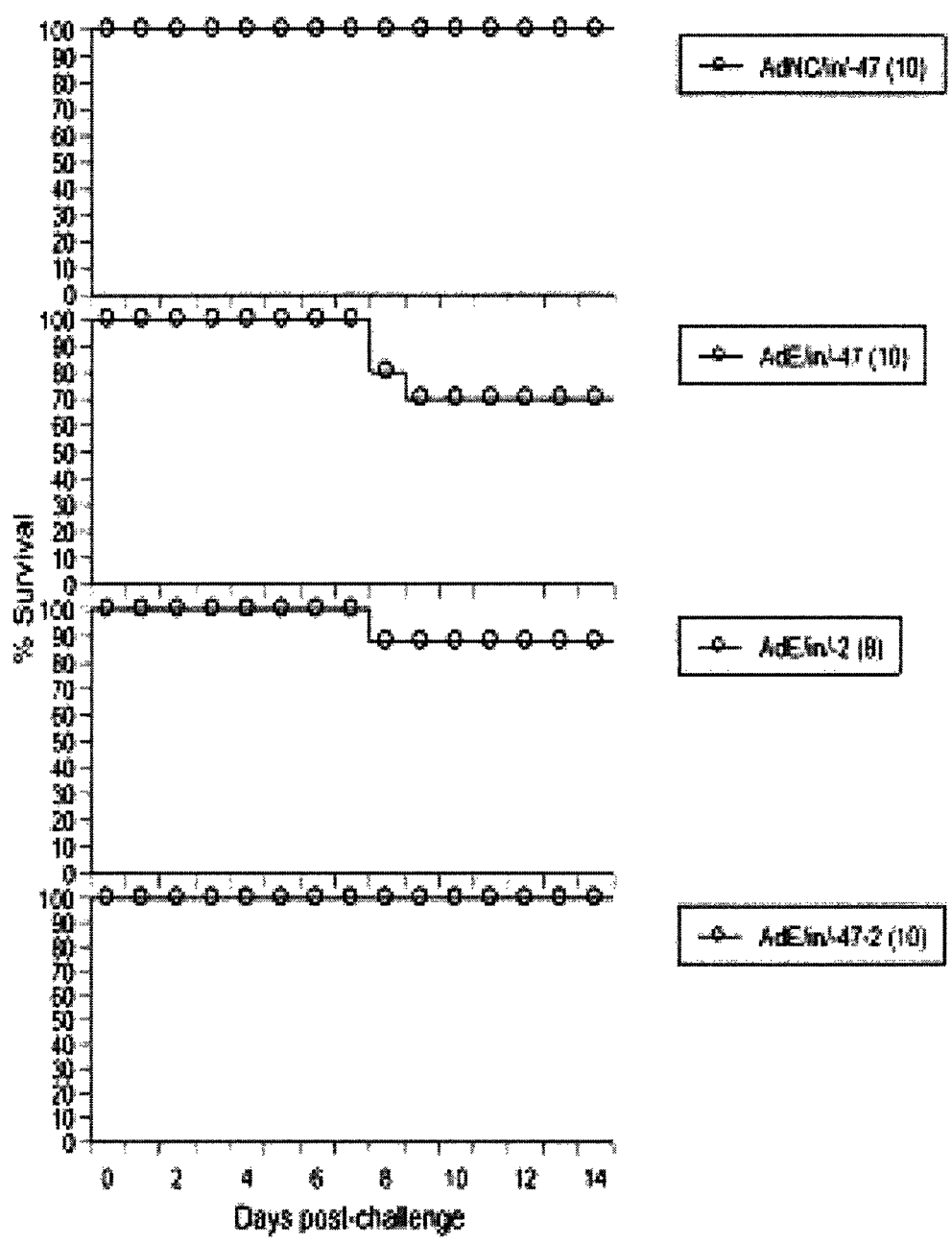
FIGS. 4A and 4B depict protection of mice by Ad5-mediated prophylactic therapy and vaccination against a higher dose of PR8 challenge. AdNC/in/−47, i.n. administration of AdNC.H1.1 on day −47; AdE/in/−47, i.n. administration of AdE on day −47; AdE/in/−47-2, i.n. administration of AdE on day −47 followed by a booster application of day −2; AdE/in/−1, i.n. administration of AdE on day −1; wtAd/in/−1, i.n. administration of E1+/E3+ wild-type Ad5 particles on day −1; all groups were inoculated with Ad5 particles at a dose of $1.2 \times 10^8$ ifu followed by challenge with $10 \times LD_{50}$ of PR8 on day 0; body weights were recorded daily for 14 days post-challenge; other symbols and protocols are the same as those described in FIG. 3 legend.

Intranasal administration of AdE on day −47 (47 days prior to PR8 challenge) protected 70% of animals (7/10) showing that the AdE-induced anti-influenza state could persist for several weeks (FIG. 4A). Intranasal instillation of AdNC.H1.1 on day −47 protected 100% (10/10) of mice (FIG. 4A) presumably due to NC20 HA1-induced adaptive immunity which cross-reacted with PR8 even though no serum hemagglutination-inhibition (HI) antibodies to PR8 were detectable (Table 1). Unlike immunization with AdNC.H1.1 on day −47 which elicited high HI antibody titers to NC20 and undetectable titers to PR8, challenge with PR8 induced high HI antibody titers to PR8 and low titers to NC20 in survivors, and administration of either AdE or AdNC.H1.1 on day −2 induced HI titers to neither NC20 nor PR8 (Table 1). The protection afforded by i.n. administration of AdNC.H1.1 on day −47 (P,0.0001), AdE on day −47 (P=0.0032), AdE double-dose regimen (day −47 followed by a booster application on day −2) (P,0.0001), AdE on day −1 (P,0.0001) or −2 (P=0.0005) at a dose of 1.2×10$^8$ ifu all reached statistical significance when compared to that of the untreated control group.

Figure 8:
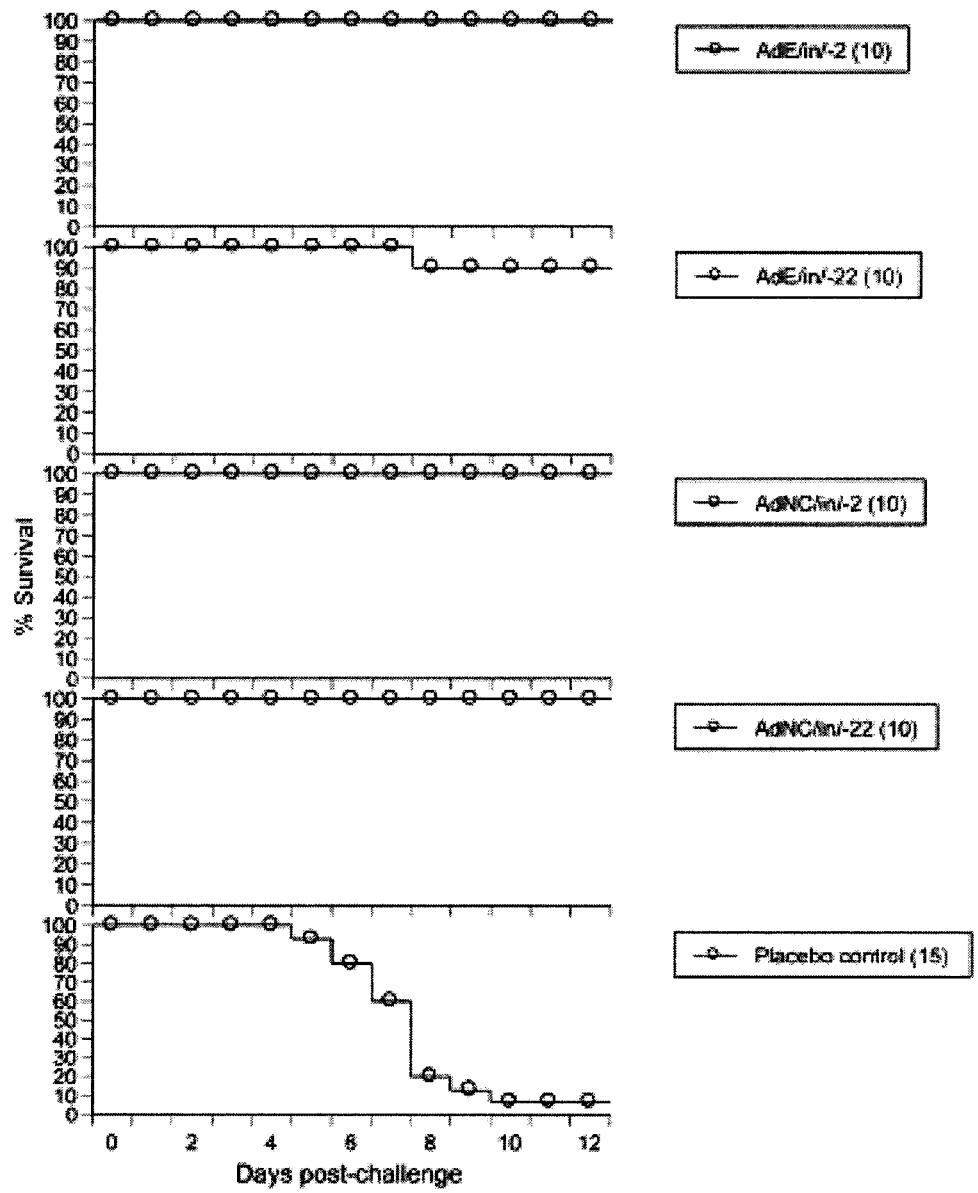
FIG. 8 depicts protection against lethal challenge by the pandemic CA04 in mice. AdE or, AdNC.H1.1 particles ($2.5 \times 10^8$ ifu per 50 µl) were i.n. instilled into mice at varying time points followed by CA04 challenge. AdE/in/−22, i.n. administration of AdE on day −22; AdNC/in/−22, i.n. administration of AdNC.H1.1 on day −22; placebo control, i.n. administration of 50 µl saline on day −22; animals were challenged by i.n. instillation of $3 \times LD_{50}$ of the pandemic CA04 on day 0; other symbols and protocols are the same as those described in FIG. 3 legend.

Protection against a pandemic IFV strain. To demonstrate that ΔE1E3 Ad5 particles can protect mice against not only PR8 but also a more clinically relevant IFV strain, 2.5×10$^8$ ifu of AdE or AdNC.H1.1 were i.n. administered into mice followed by challenging animals with a lethal dose of the (pandemic 2009 H1n1 swine flu isolate A/California/04/2009 (CA04). As shown in FIG. 8, 100% (10/10) of animals were protected by i.n. instillation of AdE or AdNC.H1.1 on day −2 and AdNC.H1.1 on day −22; 90% (9/10) were protected by i.n. administration of AdE on day −22. The protection afforded against CA04 in all these Ad5-exposed groups reached statistical significance when compared to that of the placebo control group (P,0.0001).

The non-replicating ΔE1E3 Ad5 vector has been bioengineered into a nasal influenza vaccine carrier with high potency and excellent safety profile [1]. In addition to the elicitation of protective immunity as a vaccine, we show here that this class of vaccine can also confer prophylactic therapy against influenza before adaptive immunity is elicited. It has been documented that administration of ΔE1E3 Ad5 particles into mice rapidly induces the production of a wide array of inflammatory cytokines and chemokines [6] including type I interferon (IFN-a and IFN-b) [7]; impairs lung dendritic cells [8]; activates natural killer cells [9]; induces production of the antiviral nitric oxide [10]; triggers multifaceted interactions between Ad5 and blood proteins,

TABLE 1

Serum H1 antibody titers induced by AdNCH1.1 immunization and PR8 challenge.

| Immunization | n | Day of serum collection | Log$_2$ [anti-NC20 HI GMT] (±SD) | Seroconversion to NC20 (%) | Log$_2$ [anti-PR8 HI GMT] (±SD) | Seroconversion to PR8 (%) |
|---|---|---|---|---|---|---|
| $^a$AdNC/in/−2 + PR8 | 7 | 19 | 7.9 (±0.5) | 100 | 8.9 (±0.5) | 100 |
| $^a$AdE/in/−2 + PR8 | 10 | 19 | 5.3 (±0.7) | 100 | 7.5 (±0.6) | 100 |
| $^b$AdNC/in/−47 | 10 | −1 | 10.2 (±1.7) | 100 | 2.3 (±0) | 0 |
| $^b$AdNC/in/−2 | 10 | −1 | 2.3 (±0) | 0 | 2.3 (±0) | 0 |
| $^b$AdE/in/−2 | 10 | −1 | 2.3 (±0) | 0 | 2.3 (±0) | 0 |
| $^b$Untreated control | 10 | −1 | 2.3 (±0) | 0 | 2.3 (±0) | 0 |

HI antibodies were measured against the respective IFV with titers expressed as GMT on a log$_2$ scale; a log$_2$ titer 2.3 was arbitrarily assigned to samples with undetectable titers; each serum samples was run in triplicate wells;
$^a$animals described in FIG 1. with sera collected 19 days post-PR8 challenge;
$^b$animals described in FIG 2. with sera collected 1 day prior to PR8 challenge. Seroconversion was defined as ≥ 4-fold rise in HI titer above the preimmune baseline; n, number of animals; GMT, geometric mean titer; SD, standard deviation.

Figure 4B:
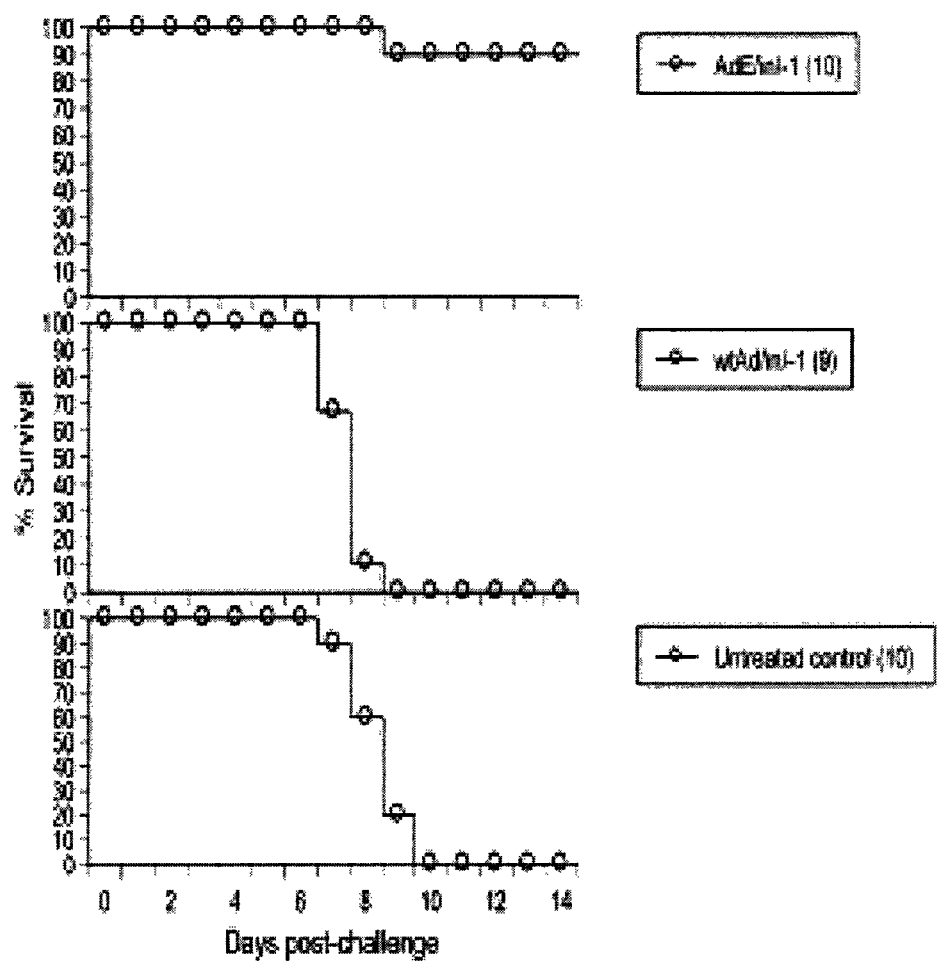
Figure 5:
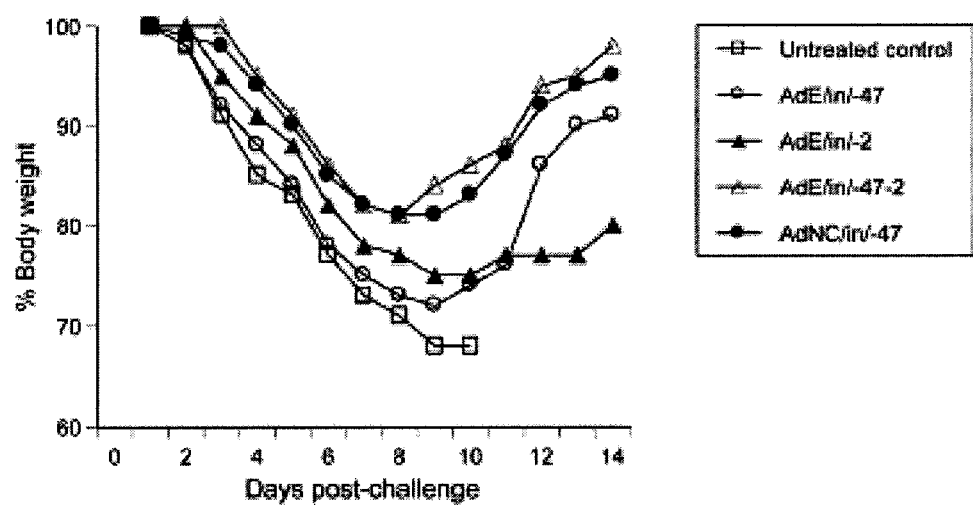
FIG. 5 depicts health status of PR8-challenged animals as shown by body weight loss. Post-challenge body weights are presented as mean % body weight by taking the body weight of individual mice on day 1 as 100%. Symbols and challenge protocols are the same as those described in FIGS. 3 and 4 legends. Although AdE/in/−47-2 and AdNC/in/−47 animals lost less weight than mice in other groups, the difference did not reach statistical significance (by one-way ANOVA with Turkey's multiple comparison post-tests; the untreated control group was excluded in statistical analysis due to early termination of data points).

Although several regimens protected mice against influenza-mediated mortality, the AdE double-dose regimen tended to confer more solid protection than its single-dose (day −47 or −2) counterpart as shown by less body weight loss after PR8 challenge even though the difference did not reach statistical significance (FIG. 5). To induce an anti-influenza state, it is essential to delete E1 and/or E3 since the E1+//E3+ wild-type Ad5 was unable to arrest influenza after i.n. administration into mice under identical conditions (FIG. 4B).

Ad5-induced protection of the lung against influenza. As shown by lung histopathology after PR8 challenge, i.n. administration of AdE or AdNC.H1.1 on day −2 protected mice against influenza by preventing the development of severe lung injuries. Intranasal instillation of PR8 without Ad5 protection induced massive pulmonary inflammation 19 days post-challenge one-way ANOVA with Turkey's multiple comparison post-tests) 7 days post-PR8 challenge.

platelets, macrophages, endothelial cells, and respective parenchymal cells [6]. Inhibition of Ad5-associated inflammation by Ad5 E1A, E1B, and E3 proteins [11] suggests that the E1+/E3+ Ad5's incompetence to induce an anti-influenza state (FIG. 4) may be attributed to suppression of inflammation, although other mechanisms cannot be excluded since ΔE1E3 Ad5 particles induce many immune as well as non-immune responses and some reactions remain undefined in animals [12]. It is conceivable that multiple reactions induced by the ΔE1E3 Ad5 particles may integrate for establishing an anti-influenza state in the airway, thus creating a multidimensional defense barrier that can hardly be bypassed by an IFV. This hypothesis is supported by the finding that the IFN-α/β receptor provides protection against influenza in a dispensable manner showing that animals have evolved overlapping mechanisms to respond to influenza [13]. Furthermore, Balb/c mice challenged in these studies carry a defective allele of the IFN-α/β-induced influenza-resistance factor Mx1. [14] implying that the ΔE1E3 Ad5-induced production of type I IFN [7] may not play a major role during the establishment of an anti-influenza state in this mouse strain.

The finding that i.n. administration of AdE 1 day post-PR8 challenge was unable to arrest influenza (FIG. 3A) suggests that the IFV may induce a pro-influenza state that is not disrupted by the ΔE1E3 Ad5 particle when the former enters the airway prior to the latter, similar to the Ad5-induced anti-influenza state that cannot be reversed by an IV when AdE particles were i.n. administered prior to PR8 or CA04 (FIGS. 3-9). To further develop the ΔE1E3 Ad5-based prophylactic drug into a post-exposure influenza drug, it is crucial to characterize the antagonistic reactions induced by the two types of viruses in the airway.

Pre-exposure to Ad5 has been associated with loss of Ad5's potency when this vector is i.m. injected [15]. However, emerging evidence shows that an Ad5-vectored nasal vaccine can bypass pre-existing Ad5 immunity in mice [15], macaques [16], and humans [17] probably due to high-efficiency gene delivery into cells in the superficial layer along the mucosal barrier in conjunction with potent antigen presentation associated with this immunocompetent interface tissue. The synergy between primary and booster applications induced by the AdE double-dose regimen (FIGS. 4A and 5) shows that the rapid anti-influenza responses induced by AdE were additive in the presence of pre-existing Ad5 immunity. These findings hold promise that this nasal influenza DVD not only is able to induce rapid and sustained protection against influenza in a single-dose regimen but also may be administered repeatedly (e.g., when a different HA is required for its vaccine component) without losing potency.

Although prophylactic influenza therapy can be performed by i.n. administration of complex bacterial lysates [18] or bacterial toxins [19], the bacterial component-induced anti-influenza state was very transient with its protective effects declining within a few days post-therapy [18, 19]. The finding that AdE-induced protective effects could persist for at least 3 weeks (FIG. 8) and up to 47 days (FIG. 4A) in a single-dose regimen suggests that the underlying mechanisms between bacterial component- and Ad5-induced anti-influenza states may differ. In addition, only the latter would allow sufficient time for the DVD's vaccine component to elicit adaptive immunity before its drug effects decline away. Moreover, the replicating wild-type Ad5 is a benign respiratory virus and its non-replicating counterpart used in this study should be even safer; notably, the safety profile of an Ad5-vectored nasal influenza vaccine in human subjects has been shown [17]. As a common respiratory virus, the human mucosal immune system is familiar with A.d.5 particles and must have evolved Ad5-specific protective mechanisms. In contrast, administration of a digestive tract-associated bacterial toxin into the respiratory tract as an influenza drug [19] would surprise the immune system and this unnatural regimen has been associated with the induction of Bell's palsy in human subjects [20].

The IFV is insidious in mutating into drug-resistant strains when it is attacked by an influenza drug [e.g., the M2 ion channel blocker (amantadine; rimantadine) or the neuraminidase inhibitor (oseltamivir; zanamivir)] [5]. Unlike contemporary influenza drugs, the Ad5-vectored DVD conceivably changes the habitat in the respiratory tract without directly attacking the IFV; hence the DVD confers no mutational pressure to induce drug resistance. In contrast to the oseltamivir-induced suppression of mucosal immunity with the risk to enhance vulnerability to subsequent mucosal pathogen infections [21], the Ad5-vectored DVD enhances mucosal innate immunity against at least a subset of mucosal. pathogens. The DVD's efficacy is further fortified by its vaccine component that elicits sustained adaptive immunity before its drug effects completely disappear (FIGS. 4A, 8 and Table 1). Since the licensed LAIV (e.g., FluMistH in the U.S.) contains live IFV [1], co-administration of LAIV with an influenza drug would be counter-productive because the drug would disable the vaccine by killing live IFV. The Ad5-vectored DVD not only is compatible with a licensed influenza drug, but also it confers prophylactic therapy as a drug by itself in addition to its vaccine capacity.

Emerging evidence shows that a number of nasal vaccines induce a weaker systemic adaptive immune response than their parenteral counterparts [22-26] even though nasal vaccines confer more robust protection against a respiratory mucosal pathogen by eliciting a more potent mucosal adaptive immune response [22,25]. Applicant provides evidence that not only adaptive immunity but also innate immunity could be induced with a focus on the respiratory tract against mucosal pathogens when the ΔE1E3 Ad5 particle is administered i.n. but not i.m., as shown by % survival afforded by i.n. and i.m. routes, respectively (FIG. 3). Whether the Ad5-vectored nasal DVD can confer protection against influenza induced by other routes (e.g., oral infection) remains to be seen.

The finding that i.n. administration of AdNC.H1.1 on day −47 induced more robust protection against PR8 challenge than its counterpart inoculated on day −2 or AdE administered on day −47 (FIGS. 3B and 4A) suggests that animals in the AdNC/in/−47 group may be protected by an NC20 HA1-mediated adaptive immune response that cross-reacted with PR8 47 days post-immunization in the absence of detectable serum HI antibody to PR8 (Table 1). The data corroborate other reports that serum HI antibody titer is an inadequate surrogate marker for predicting protective immunity induced by a nasal influenza vaccine [24,26].

The findings that the Ad5-vectored DVD can confer prophylactic therapy in conjunction with vaccination in a single package provide a foundation for the development of a novel anti-influenza agent that can be mass-produced in cultured cells, administered painlessly by nasal spray, with the capacity to bypass pre-existing Ad5 immunity and mobilize the innate as well as the adaptive immune repertoires toward a rapid and sustained beneficial response against influenza, without the potential to generate drug resistant IFV strains.

Adenovirus. To generate the AdE particle, homologous recombination between the shuttle pAdHigh and the Ad5 backbone pAdEasy-1 plasmids was performed in *Escherichia coli* BJ5183 cells followed by generation of the RCA-free AdE particle in PER.C6 cells (provided by Crucell Holland BV; Leiden, The Netherlands) as described [1]. AdE is thus a ΔE1E3 Ad5 with an expression cassette in its E1 region [1] without encoding any transgene. To generate the AdNC.H1.1 vector, the NC20 HA gene was synthesized at GENEART (Regensburg, Germany) with codons optimized to match the tRNA pool found in human cells in conjunction with the insertion of a eukaryotic ribosomal binding site immediately upstream from the initiation ATG codon[27]. The NC20 HAI fragment containing 347 amino acids was amplified from the synthetic HA template by polymerase chain reaction (PCR) using primers 5'-CACAGGTACCGC-CACCATGAAGGCCAAGCTG-3' (SEQ ID NO: 1) and 5'-GAGTCTAGAT-TATCAGCCGAACAGGCCTCTGCTCTGG-3' (SEQ ID NO: 2). The KpnI-XbaI fragment containing the amplified HAI fragment with a stop codon added in-frame was inserted into the KpnI-XbaI site of pAdHigh in the correct orientation under transcriptional control of the human cytomegalovirus (CMV) early promoter. An RCA-free Ad5 vector encoding the NC20 HAI (AdNC.H1.1) was subsequently generated in PER.C6 cells as described above. Both AdE and AdNC.H1.1 were validated by DNA sequencing; mass-produced in PER.C6 cells; purified by ultracentrifugation over a cesium chloride gradient as described [27]; dialyzed into A195 buffer [28] with titers (ifu per ml) determined in 293 cells [17] by the Spearman-Karber method [29] after staining Ad5-infected monolayers with a horseradish peroxidase (HRP)-conjugated anti-Ad5 hexon antibody and the 3,3'-diaminobenzidine tetrahydrochloride (DAB) substrate (Clontech Laboratories, Inc.; Mountain View, Calif.). The E1+/E3+ wild-type Ad5 (VR-1516) was obtained from the American Type Culture Collection (ATCC; Manassas, Va.).

Influenza virus. PR8 (VR-95) was obtained from the ATCC and grown in Madin Darby Canine Kidney (MDCK) cells in the presence of TPCK-trypsin as described [17] with titers determined by plaque assay [30]. The mouse-adapted CA04 was generated by Natalia A. Ilyushina and provided by Elena Govorkova at the St. Jude Children's Research Hospital (Memphis Tenn.). The CA04 virus was adapted to replication in the lungs of Balb/c mice by 9 sequential passages through mouse lungs. Virus was plaque purified in MDCK cells and a virus stock was prepared by growth in 10-day-old embryonated chicken eggs and then MDCK cells as described [31] with titers expressed as cell culture infectious doses (CCID50) as described [32]. NC20 was provided by the Center for Disease Control (CDC; Atlanta, Ga.)

Challenge studies. intranasal administration and i.m. injection of 50 μl of Ad5 particles into young (approximately 2 months old) female Balb/c mice were performed as described [27]. Mice were challenged by i.n. instillation of 50 μl of PR8 containing either $1.4 \times 10^6$ plaque-forming units (pfu) [equivalent to approximately $4 \times LD_{50}$ (50% lethal dose)] or $3.5 \times 10^6$ pfu (equivalent to approximately $10 \times LD50$) at University of Alabama at Birmingham (UAB), as well as 90 μl of CA04 containing 26105 CCID50 (equivalent to approximately $3 \times LD_{50}$) at Utah State University (USU). All experiments using mice were performed in accordance with the approval of the Institutional Animal Care and Use Committees at UAB and USU (LAB Approval ID, #7705; UAB Animal Welfare Assurance Number, A3255-01; USU Approval ID, #552; USU Animal Welfare Assurance Number, A3801-01). Animal facilities at both UAB and USU have been AAALAC accredited.

Figure 7:
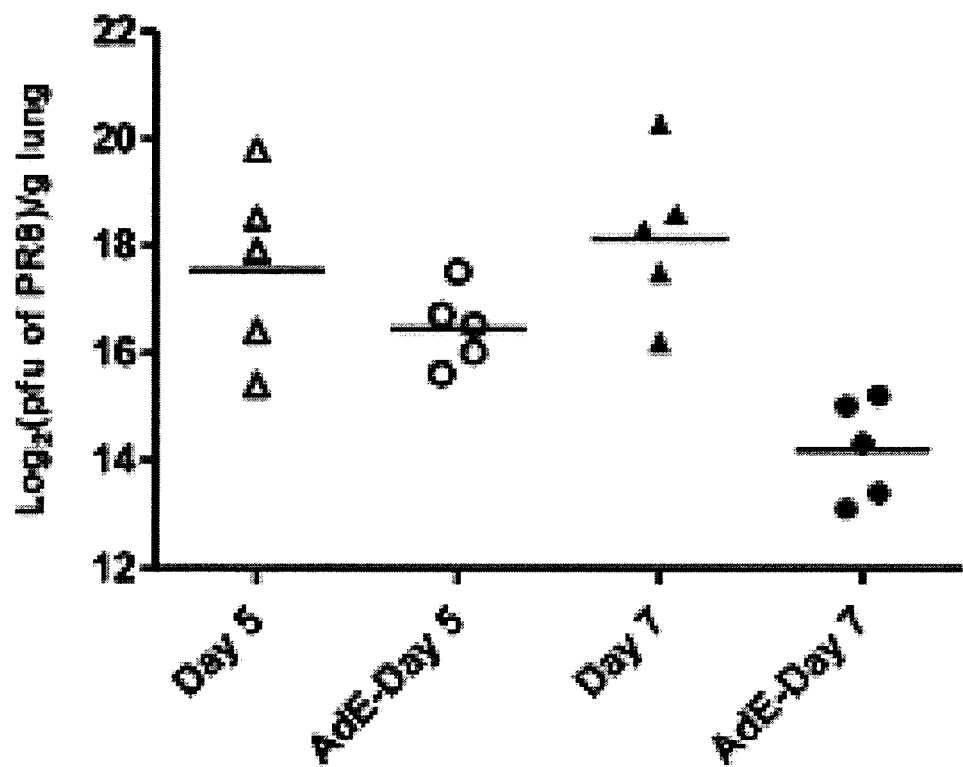
FIG. 7 depicts PR8 titers in lungs post-challenge. AdE particles ($1.2 \times 10^8$ ifu per 50 ml) were i.n. instilled into mice on day −2 followed by challenging control and AdE-exposed mice with $4.6 \times 10^6$ pfu of PR8 on day 0. Day 5, PR8 titers in lungs resected from control mice 5 days post-PR8 challenge; AdE-Day 5, PR8 titers in lungs resected from AdE-exposed mice 5 days post-PR8 challenge; Day 7, PR8 titers in lungs resected from control mice 7 days post-PR8 challenge; AdE-Day 7, PR8 titers in lungs resected from AdE-exposed mice 7 days post-PR8 challenge; triangle and circle, $\log_2$(pfu of PR8)/g lung in individual mice; bar, geometric mean of PR8 titers in lungs. No PR8 titers were detected in lungs resected from control mice that were not challenged with PR8. The difference between Day 7 and AdE-Day 7 reached statistical significance (by one-way ANOVA with Turkey's multiple comparison post-tests).

PR8 titers in lungs post-challenge. AdE particles were i.n. administered into young female Balb/c mice at a dose of $1.2 \times 10^8$ ifu in a volume of 50 μl on day −2 Five to seven days after i.n. instillation of $4.6 \times 10^6$ pfu of PR8 on day 0, control and AdE-exposed mouse lungs were immediately frozen on dry ice after resection and stored at 280 uC until analysis (FIG. 7). After thawing, a fraction of each lung was weighed and homogenized in cold phosphate buffered saline (PBS) as a 10% (w/v) suspension. Tissue debris was removed by centrifugation and the supernatant was transferred to another sterile tube for virus titration. Plaque assay of IFV was performed as described [30].

Hemagglutination-inhibition assay. Sera were tested for activity against PR8 or NC20 by standard HI assay after pre-treatment of the sera with a receptor-destroying enzyme as described [17]. Each serum sample was tested beginning at a dilution of 1:10. All sera were tested in a blinded fashion on code-labeled, matched pre- and post-immunization samples. Animals were considered seronegative and assigned an HI antibody titer of 5 (2.3 on a log 2 scale) if their serum specimen had an HI titer of <10.

Lung histopathology assay. Mouse lungs were fixed by perfusing 10% buffered. formal in through the trachea. Paraffin-embedded tissues were cut into 5-μm-thick slices followed by staining sections with hematoxylin and eosin (FIG. 6).

Statistical analysis. All statistical analysis was performed using GraphPad Prism version 5.04 (GraphPad Software, San Diego, Calif.). Log-rank tests were performed for comparing Kaplan-Meier survival curves; and one-way ANOVA with Turkey's multiple comparison post-tests were performed for comparing body weight loss as well as PR8 titers in lungs. Statistical significance was set at P,0.05.

REFERENCES

1. Tang D C, Zhang J, Toro H, Shi Z, Van Kampen K R (2009) Adenovirus as a carrier for the development of influenza virus-free avian influenza vaccines. Expert Rev Vaccines 8: 469-481.
2. Neumann G, Watanabe T, Ito H, Watanabe S, Goto H, et al. (1999) Generation of influenza A viruses entirely from cloned cDNAs. Proc. Natl. Acad. Sci. USA 96: 9345-9350.
3. Wei C J, Boyington J C, McTamney P M, Kong W P, Pearce M B, et al. (2010) Induction of broadly neutralizing H1N1 influenza antibodies by vaccination. Science 329: 1060-1064. 4. 4.
   Konig R, Steitz S, Zhou Y, Inoue A, Hoffmann H H, et al. (2010) Human host factors required for influenza virus replication. Nature 463: 813-817.
5. Poland G A, Jacobson R M, Ovsyannikova I G (2009) influenza virus resistance to antiviral agents: a plea for rational use. Clin Infect Dis 48: 1254-1256.
6. Hartman Z C, Appledore D M, Amalfitano A (2008) Adenovirus vector induced innate immune responses: impact upon efficacy and toxicity in gene therapy and vaccine applications. Virus Res 132: 1-14.
7. Yamaguchi T, Kawabata K, Kouyama E, Ishii K J, Katayama K, et al. (2010) Induction of type I interferon by adenovirus-encoded small RNAs. Proc Natl Acad Sci USA 107: 17286-17291.
8. Thiele A T, Sumpter T L, Walker J A, Xu Q, Chang C H, et al. (2006) Pulmonary immunity to viral infection: adenovirus infection of lung dendritic cells renders T cells nonresponsive to interleukin-2. J Virol. 80: 1826-1836.
9. Zhu J, Huang X, Yang Y (2008) A critical role for type I IFN-dependent NK cell activation in innate immune elimination of adenoviral vectors in vivo. Mol Ther 16: 1300-1307.
10. Higashimoto Y, Yamagata Y, Itoh H (2006) Complex effect of adenovirus early region proteins on innate immune system. Inflamm Allergy Drug Targets 5: 229-237.
11. Schaack J, Bennett M L, Colbert J D, Torres A V, Clayton G H, et al. (2004) E1A and E1B proteins inhibit inflammation induced by adenovirus, Proc Natl Acad Sci. USA 101: 3124-3129.
12. Rhee E G, Blattman J N, Kasturi S P, Kelley R P, Kaufman D R, et al. (2011) Multiple innate immune pathways contribute to the immunogenicity of recombinant adenovirus vaccine vectors. J Virol 85: 315-323.
13. Goodman A G, Zeng H, Proll S C, Peng X, C, et al. (2010) The alpha/beta interferon receptor provides protection against influenza virus replication but is dispensable for inflammatory response signaling. J Virol 84: 2027-2037.
14. Tumpey T M, Szretter K J, Van Hoeven N, Katz J M, Kochs G, et al. (2007) The Mx1 gene protects mice against the pandemic 1918 and highly lethal human H5N1 influenza viruses. J Virol 81: 10818-10821.
15. Croyle M A, Patel A, Tran K N, Gray M, Zhang Y, et al. (2008) Nasal delivery of an adenovirus-based vaccine bypasses pre-existing immunity to the vaccine carrier and improves the immune response in mice. PLoS ONE 3: e3548,
16. Song K, Bolton D L, Wilson R L, Camp J V, Bao S, et al. (2010) Genetic immunization in the lung induces potent local and systemic immune responses. Proc Natl Acad Sci USA 107: 22213-22218.
17. Van Kampen K R, Shi Z, Gao P, Zhang J, Foster K W, et al. (2005) Safety and immunogenicity of adenovirus-vectored nasal and epicutaneous influenza vaccines in humans. Vaccine 23: 1029-1036.
18. Tuvim M J, Evans S E, Clement C G, Dickey B F, Gilbert B E (2009) Augmented lung inflammation protects against influenza A pneumonia. PLoS ONE 4: e4176.
19. Norton E B, Clements J D, Voss T G, Cárdenas-Freytag L (2010) Prophylactic administration of bacterially derived immunomodulators, improves the outcome of influenza virus infection in a murine model, J. Virol. 84: 2983-2995.
20. Couch R B (2004) Nasal vaccination, *Escherichia coli* enterotoxin, and Bell's palsy. N. Engl. J. Med 350: 860-861.
21. Takahashi E, Kataoka 1, Fujii 1, Chida J, Mizuno D, et al. (2010) Attenuation of inducible respiratory immune responses by oseltamivir treatment in mice infected with influenza. A virus, Microbes infect 12: 778-783.
22. Wang J, Thorson L, Stokes R W, Santosuosso M, Huygen K, et al. (2004) Single mucosal, but not parenteral, immunization with recombinant adenoviral-based vaccine provides potent protection from pulmonary tuberculosis. J Immunol 173: 6357-6365.
23. Lemiale F, Kong W P, Akyurek L M, Ling X, Huang Y, et al. (2003) Enhanced mucosal immunoglobulin A response of intranasal adenoviral vector human immunodeficiency virus vaccine and localization in the central nervous system. J Virol 77: 10078-10087.
24. Hoelscher M A, Garg 5, Bangari D 5, Belser J A, Lu X, et al, (2006) Development of adenoviral-vector-based pandemic influenza vaccine against antigenically distinct human H5N1 strains in mice. Lancet 367: 475-481,
25. Price G E, Soboleski M R, Lo C Y, Misplon J A, Quirion M R, et al. (2010) Single dose mucosal immunization with a candidate universal influenza vaccine provides rapid protection from virulent H5N1, H3N2 and H1N1 viruses. PLoS ONE 5: e13162.
26. Clements M L, Betts R F, Tierney E L, Murphy B R (1986) Serum and nasal wash antibodies associated with resistance to experimental challenge with influenza A wild-type virus. J Clift Microbiol 24: 157-160.
27. Shi Z, Zeng M, Yang G, Siegel F, Cain L J, et al. (2001) Protection against tetanus by needle-free inoculation of adenovirus-vectored nasal and epicutaneous vaccines. J Virol 75: 11474-11482.
28. Evans R K, Nawrocki D K, Isopi L A, Williams D M, Casimiro D R, et al. (2004) Development of stable liquid formulations for adenovirus-based vaccines. J Pharm Sci 93: 2458-2475.
29. Lynn D E (2001) Effects of temperature on the susceptibility of insect cells to infection by baculoviruses. Methods Cell Sci 23: 221-225. 30. Gaush C R, Smith T F (1968) Replication and plaque assay of influenza virus in an established line of canine kidney cells. Appl Microbiol 16: 588-594.
31. Ilyushina N A, Khaterikov A M, Seiler J P, Forrest H L, Bovin N V, et al. (2010) Adaptation of pandemic H1n1 influenza viruses in mice. J Virol 84: 8607-8616.
32. Barnard D L, Wong M H, Bailey K, Day C W, Bidwell R W, et al. (2007) Effect of oral gavage treatment with ZnAL42 and other metallo-ion formulations on influenza A H5N1. and H1N1 virus infections in mice. Antivir Chem Chemother 18: 125-132.

Example 3

Adenovirus-Vectored Drug-Vaccine Duo as a Potential Driver for Conferring Mass Protection Against Infectious Diseases The disease-fighting power of vaccines has been a public health bonanza credited with the worldwide reduction of mortality and morbidity. The goal to further amplify its power by boosting vaccine coverage requires the development of a new generation of rapid-response vaccines that can be mass produced at low costs and mass administered by nonmedical personnel. The new vaccines also have to be endowed with a higher safety margin than that of conventional vaccines. The nonreplicating adenovirus-vectored vaccine holds promise in boosting vaccine coverage because the vector can be rapidly manufactured in serum-free suspension cells in response to a surge in demand, and noninvasively administered by nasal spray into human subjects in compliance with evolutionary medicine. In contrast to parenteral injection, noninvasive mucosal vaccination minimizes systemic inflammation. Moreover, preexisting adenovirus immunity does not interfere appreciably with the potency of an adenovirus vectored nasal vaccine. Nasal administration of adenovirus vectors encoding pathogen antigens is not only fear-free and painless, but also confers rapid and sustained protection against mucosal pathogens as a drug-vaccine duo since adenovirus particles alone without transgene expression can induce an anti-influenza state in the airway. In addition to human vaccination, animals can also be mass immunized by this class of vectored vaccines.

A litany of demands for better vaccines. Although vaccination proves to be the most cost-effective method for the prevention of disease, a sweeping offensive to boost vaccine coverage remains a compelling goal in the movement toward improved public health worldwide. Current vaccines that have been licensed for marketing include killed whole microorganisms, live attenuated microorganisms, microbial extracts, purified or recombinant proteins, DNA vaccines and virus-like particles. Even though many diseases have been defeated by the broad distribution of these vaccines, the goal to generate community (herd) immunity in a wide variety of disease settings remains elusive owing to a number of problems in current vaccination programs. Specifically, vaccine-associated adverse side effects range from local and systemic inflammatory response, fever, platelet activation, cardiac autonomic dysfunction, anaphylactic reaction (induced by needle injection of certain vaccines) [1-4] to the rare occurrence of paralytic poliomyelitis (mediated by ingestion of the oral polio vaccine) [5], myopericarditis (induced by inoculation of the Dryvax smallpox vaccine) [6] and Bell's palsy (induced by a bacterial toxin nasal adjuvant) [7,8]. In 2010, a sudden rise of narcolepsy among vaccinees was reported in a few countries following needle injection of an H1N1 pandemic influenza vaccine containing the squalene adjuvant [201]. Injection of squalene alone can induce rheumatoid arthritis in animals [9]. As emerging evidence shows that chronic, low-grade inflammation is associated with cardiovascular disease [10], obesity [11], diabetes [11], cancer [12] and neurological disorder [13], vaccine-induced inflammation now needs focused attention. Whether an acute inflammatory reaction induced by injection of an immunostimulating vaccine-adjuvant complex [1-3] could evolve into a chronic, tow-grade inflammation and trigger any of these ailments in a subset of vaccinees over time is of paramount importance in public health; however, this potential hazard has not been rigorously investigated. Since the concept of vaccine safety is evolving from 'protection against pathogen-induced diseases' to 'no possibility of inducing adverse consequences', any known extraneous agents, toxicity and residual virulence found in a vaccine would not be allowed, and any possibility of inducing unknown side effects (e.g., inflammation in vital organs) should be avoided.

Mucosal and systemic immune responses are elicited and regulated with a considerable degree of independence and most vaccines have been administered invasively by intramuscular injection, which induces good systemic immunity but often weak mucosal immunity that is crucial in defense against mucosal pathogens (e.g., influenza virus, *Mycobacterium tuberculosis* and HIV) [14,15]. Efficient induction of mucosal immunity usually employs nasal or oral vaccination owing to the unique ability of resident mucosal dendritic cells (DCs) to induce IgA switching and to imprint mucosa-specific homing receptors (e.g., CCR9 and a4b7 integrin) on lymphocytes [15,16]. In addition to weak mucosal immunity induced by an injectable vaccine, the syringe needle as a vaccine administration device also poses serious problems through intentional or inadvertent unsterile re-use, needle-stick injury, improper waste disposal, as well as limited injection service by licensed medical personnel during a crisis [17]. Public fear of pointed needles (aichmophobia) plays another role in hindering vaccine coverage. Some people may thus prefer the odds of getting a disease versus the odds of inflicting pain, injury, or death by systemic vaccination. Since the objective of vaccination programs is to reduce the overall probability of infection by generating community (herd) immunity, the mission will be undermined by a hold-off on vaccination owing to public fear of risks. To date, enabling technologies for reversing negative perceptions by developing a new generation of rapid-response vaccines that are safe, efficacious, painless and economical are emerging on the horizon.

Noninvasive vaccination as a means to boost vaccine coverage. Needle-free noninvasive vaccination holds the promise of changing the public's attitude from 'being forced to get a needle shot' to 'proactively seeking vaccination without fear'. Vaccines can be administered noninvasively by oral ingestion [5], nasal spray [18,19], as well as topical application of a skin patch [19-23] in a painless manner. Noninvasive vaccination by administration of vaccines to the interface between the inner body and outside environment not only confers a high degree of vaccinee comfort, but may also lead to a qualitatively superior immune response as compared with conventional systemic vaccination. Mucocutaneous surfaces are covered by a highly immunocompetent epithelium that serves as a physical barrier and ensures that antigens penetrating into the superficial layer are efficiently captured and presented to the immune system. By logic, animals and humans must deploy the most competent immune cells along the surface barrier to ward off infections since it would be counter-productive to keep these 'professional immune soldiers' in deep tissues where they rarely encounter invading pathogens. Professional antigen-presenting cells (APCs) including multiple DC subsets [24,25], gdT cells [26] and others can be found in high densities along the mucocutaneous surface. A subset of mouse bone marrow cells expressing the retinoic acid-synthesizing enzyme are capable of providing retinoic acid to DC precursors for inducing mucosal DC functions, including generation of Foxp3+ regulatory T cells, IgA-secreting B cells and mucosa-specific homing receptors [27]. It has been shown that the route of vaccination critically impacts not only the magnitude but also the phenotype and trafficking of antigen-specific CD8+ T lymphocytes in mice. Intramuscular injection of an adenovirus (Ad)-vectored vaccine induced robust local transgene expression and elicited high-frequency, polyfunctional CD8+ T lymphocytes that trafficked broadly to both systemic and mucosal compartments. By contrast, intranasal instillation of the Ad-vectored vaccine led to similarly robust local transgene expression but generated low-frequency, monofunctional CD8+ T lymphocytes with restricted anatomic trafficking patterns [28]. Noninvasive vaccination thus takes advantage of an existing biological pathway that leverages the immune system's ability to respond at superficial but immunocompetent tissue sites along the mucocutaneous surface to elicit localized protective immunity against mucosal pathogens at the portal without inducing an over-reactive systemic immune response.

Although it is required to aseptically manufacture vaccines under current good manufacturing practices, contamination by unknown microorganisms or contamination below detection by modern instruments and high-throughput assays may still occur. Coadministration of these contaminants with a noninvasive vaccine onto the mucocutaneous surface would pose little danger to the vaccinee since the mucocutaneous immune system is well versed in counteracting microbial invasion at all times as the interface is in constant contact with microbes. By contrast, injection of a contaminated vaccine into deep tissues can, in theory, trigger an exponential growth of microorganisms within the body in the absence of a timely immune response, or conversely, an 'immune storm' induced by an over-reacting immune system. Overall, elicitation of protective immunity along the mucocutaneous surface is a daily routine; animals and humans have evolved adequate mechanisms for winning daily battles (daily microbial invasion) without losing the war (overall health). Noninvasive vaccination utilizes the daily operation of the immune system along the interface without surprising the immune system by physical delivery of immunostimulating vaccine-adjuvant complexes into deep tissues where immunocompetence is low.

The zigzag pathway to develop an adenovirus into a vaccine carrier. Adenovirus belongs to a family of icosahedral nonenveloped DNA viruses with a linear DNA genome of 30-38 kb (size varies from group to group) bracketed by inverted terminal repeats. An Ad particle contains a tightly coiled DNA genome packaged inside a hexagonal protein capsid (FIG. 9). The Ad genome contains both early genes encoding regulatory proteins and late genes encoding structural proteins [29]. Multiple Ad serotypes are commonly found in animals and humans, and there can be significant differences in the pathogenicity and course of disease among different serotypes; some are quite benign in immunocompetent human hosts (e.g., human Ad serotype 5 [30])

whereas others may cause diseases that are usually mild and self-limiting. A number of noteworthy reasons warrant the development of Ad into a vaccine carrier. Specifically, human Ad4- and Ad7-based oral vaccines (a type of noninvasive vaccine) have proven safe as well as efficacious during mass immunization of military recruits [31]. Potentially, replicating Ad4 or Ad7 can be further bioengineered into oral vaccine carriers to elicit immunity against other pathogen-derived antigens. However, it is difficult to quantitatively release a replicating bioengineered vector that represents a genetically modified organism in a controlled manner. Introduction of a genetically modified organism into the ecosystem is also undesirable in the public's perception. A nonreplicating vector thus would be safer and more acceptable than its replicating counterpart. Although a nonreplicating Ad5 vector was developed nearly three decades ago by truncating its E1 region (FIG. 9) [32], a critical issue for the E1-defective (ΔE1) Ad5 vector produced in human 293 cells is the intrinsic contamination by replication-competent Ad (RCA) that arises through homologous recombination between overlapping sequences framing the E1 locus displayed by transfected 293 cells and the vector backbone [33], RCA represents a biohazard because it can replicate in an infected host with the capacity for horizontal transmission to bystanders through virus shedding [30]. To circumvent the problem of RCA, RCA-free Ad vectors have been generated in human PER.C6 cells using PER.C6-compatible shuttle vectors that do not contain overlapping sequences with the PER.C6 genome [34,35]. Unlike replicating Ad4 and Ad7, the nonreplicating Ad5 does not immunize animals efficiently when administered orally due to its inability to undergo virus amplification and its susceptibility to low pH, gastric and pancreatic proteases, and extracellular mucins [36].

Figure 10:
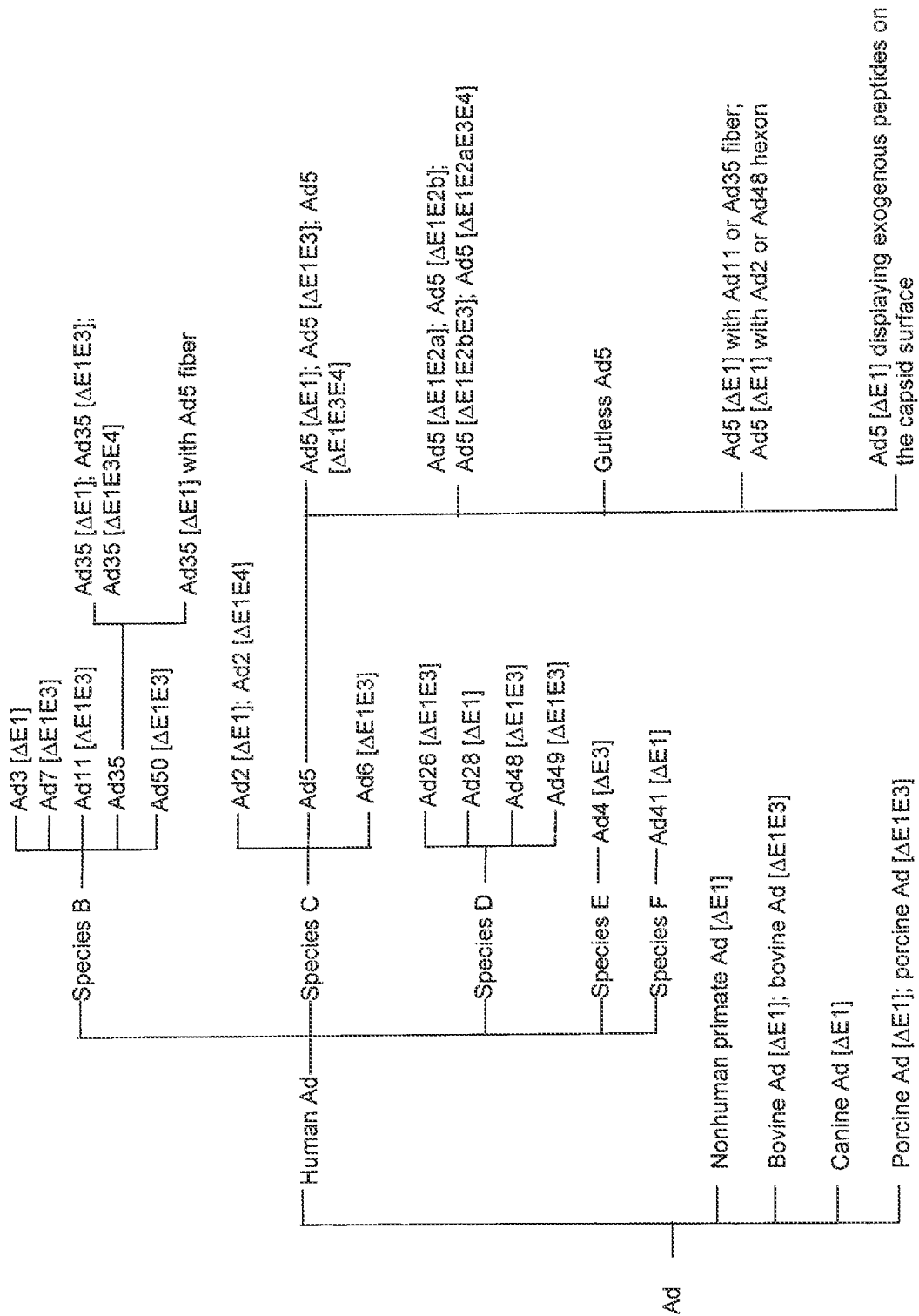
FIG. 10 depicts a pedigree chart of bioengineered non-replicating adenovirus vectors. Both human and animal Ad have been bioengineered into a wide variety of non-replicating Ad vectors for the delivery of exogenous genes into animal and human subjects. Ad: Adenovirus.

Despite problems observed following administration by the oral route, the nonreplicating E1/E3-defective (ΔE1E3) Ad5 (FIG. 9) has been developed and used as a parenteral gene-therapy vector in a large number of therapeutic trials owing to its high capacity for accommodating transgenes, high-titer production, high-efficiency gene delivery and high-level transgene expression (at least as an initial burst) [35]. However, Ad5 is not an ideal vector for classical gene therapy because transgene expression is transient [35]. Therefore, use of an Ad5 vector fails to meet a major goal of gene therapy, which usually requires sustained transgene expression. Moreover, the common presence of pre-existing Ad5 immunity in human populations [37-39] and the rapid development of an anti-Ad5 immune response following the first inoculation with the vector [40, 41] have impeded its clinical use by limiting gene transfer efficiencies. Strategies to circumvent these drawbacks include serotype switching, capsid modification and development of nonhuman Ad vectors, on the assumption that another Ad vector can substitute when the initial one is disabled by pre-existing Ad immunity. Although human Ad3, Ad4, Ad35, Ad41 or a chimeric Ad5 containing the Ad11 or Ad35 fibers have been bioengineered into nonreplicating Ad vectors (FIG. 10), Ad5 is still more potent and safer than other serotypes in pre-clinical animal models [42]. A number of nonhuman Ad5 such as bovine Ad [43], porcine Ad [43] and nonhuman primate Ad [44] have also been developed to expand the repertoire of Ad vectors (FIG. 10). Even though a porcine Ad-vectored vaccine can be at least as potent as its Ad5 counterpart in mice [45], the human Ad5 is still the premier gene-transfer vector owing to the risk of inducing unpredictable human ailments by a nonhuman Ad [46]. The genome of human Ad5 is remarkably stable in the field even after coinfection with other Ad serotypes [47]. Moreover, the Ad5 vector has been further developed to display foreign antigens on the surface after fusing pathogen epitopes to the pIX [48] or the hexon capsid proteins [49] in addition to encoding pathogen antigens in its DNA genome (FIG. 10). Less immunogenic Ad5 vectors were developed by deletion of E2b [50, 51] or nearly all Ad5 sequences except the inverted terminal repeats and the packaging signal (gutless Ad) (FIG. 10) [52]. To date, these sophisticated strategies have not yet yielded profound clinical improvement.

In contrast to intramuscular or intravenous injection of Ad5, it has been shown that intranasal administration (the natural route of Ad5 infection) would allow a ΔE 1E3 Ad5-vectored vaccine to bypass pre-existing Ad5 immunity without appreciably losing potency in mice [41, 53], non-human primates [54] and humans [19]. These observations are conceivably attributed to the high efficiency of gene delivery, robust transgene expression and potent antigen presentation along the mucosal barrier in the respiratory tract. Anti-Ad5 immunity is thus no longer an insurmountable limiting factor and refinement of bioengineered Ad vectors may no longer be a sine qua non for further development of Ad-vectored vaccines.

The Ad5 vector's reputation has been derailed multiple times during its development. In addition to pre-existing Ad5 immunity, the death of a patient with partial ornithine transcarbamylase (OTC) deficiency after infusing a high dose of Ad5-OTC vector into his hepatic artery during a human gene-therapy trial [55] marked Ad5 as a dangerous vector in the public's perception. Evidence shows that injection of Ad particles into the circulatory system (an unnatural route for Ad infection) is an unsafe approach because Ad particles rapidly induce systemic inflammation postinjection [56, 57], and a variety of Ad serotypes cause activation of coagulation, possibly through interaction with platelets [42]. During a large-scale human trial (Step Study) of an Ad5-vectored HIV vaccine, administration by intramuscular injection did not lower HIV viral load and vaccination was associated with increased risk of human HIV infection in Ad5-seropositive subjects [58, 59]. The counterintuitive results may again be attributed to a misuse of the vector since the potency of an Ad5-vectored vaccine surpasses that of other virus- and nonvirus-based vaccine platforms in eliciting cellular immunity [60]; consequently, the Ad5-induced expansion of CD4+ T cells would exacerbate this peculiar disease as CD4+ T cells are the specific targets for HIV infection [61]. In addition, human subjects were immunized by intramuscular injection of Ad5 particles during the Step Study [58, 59], which is not very potent in eliciting mucosal immunity against a mucosal pathogen such as HIV [14,62,63].

Reality check of current adenovirus-vectored vaccines. To develop the next generation of vaccines that are safe and effective, it is crucial for the vaccine to induce protective immunity rapidly with a high benefit-to-risk ratio. The manufacture, distribution and administration of the vaccine must be easy, fast and economical. In addition, the inherent stability of the formulated vaccine and final filled product has to allow for long-term stockpiling without a cold chain.

As shown in Table 2, protective immunity against a wide variety of pathogens has been elicited in mice, guinea pigs, chickens, hamsters, cotton rats, raccoons, skunks, pigs and nonhuman primates following immunization with Ad-vectored vaccines. Overall, Ad-vectored vaccines can confer rapid and more robust protection against live pathogens than other types of vaccines in animal models.

Although multiple human clinical trials of Ad-vectored vaccines have been performed, few immunized human subjects have been challenged with a virulent live pathogen (Table 3). Notably, a subset of human volunteers immunized by intramuscular injection of DNA and Ad5-vectored malaria vaccines (DNA-primed/Ad5-boosted) were protected against live malaria sporozoite challenge following mosquito feeding in Ad5-seronegative human subjects. It has been shown that DNA vaccination alone without Ad5 booster failed to protect humans against malaria; whether Ad5 vaccination alone could confer protection remains to be seen [64]. Even though immunized humans were not challenged with live pathogens during most human trials (Table 3), they have provided a broad safety database for the use of Ad vectors in humans.

Potency & safety of adenovirus-vectored nasal vaccines. As described earlier, nasal vaccination induces potent mucosal immunity in a needle-free manner. Respiratory tract DCs form a contiguous subepithelial network within the nasorespiratory tract, bridging innate and acquired immunity. The density of DCs within the respiratory tract is highest in those areas exposed to greater amounts of inhaled antigen [65]. Nasopharynx-associated lymphoid tissue, constituting Waldeyer's ring in humans, is a unique inductive site for B-cell responses and plasma cell generation. Nasal vaccination is thus a driver for the elicitation of humoral immunity including the formation of secretory IgA antibody within the respiratory tract [66]. Local humoral immune responses have been induced in nasal, vaginal and salivary secretions following intranasal administration of Ad-vectored vaccines into nonhuman primates [67]. An Ad5-vectored nasal vaccine induced greater antigen-specific IgA responses in mucosal secretions and sera in mice than its injectable counterpart [68]. In addition to humoral immunity, cellular immune responses were observed in systemic and mucosal immune compartments shortly after immunizing mice with an Ad-vectored herpes vaccine regardless of the route of inoculation; however, anamnestic cytotoxic T lymphocyte responses compartmentalized exclusively to mucosal or systemic lymphoid tissues after mucosal or systemic immunization, respectively, several months postimmunization [14].

Although the DNA-primed/Ad5-boosted malaria vaccine induced protection against live malaria sporozoite challenge in Ad5-seronegative human subjects, the failure to protect five Ad5-seropositive human volunteers [64] may be attributed to pre-existing Ad5 immunity [37, 38, 40, 41]. As described earlier, one approach to circumvent this hurdle is to inoculate Ad-vectored vaccines by nasal administration, which leverages what is a disadvantage for injectable vaccines to an advantage for noninvasive mucosal vaccines without reduced effectiveness of subsequent Ad5 re-administration [19, 41, 53, 54]. An Ad5-vectored nasal vaccine may induce focused mucosal immunity in the airway, as shown by findings that intranasal immunization, but not systemic immunization, induces long-lived cytotoxic T lymphocytes in mucosal tissues [14]. In addition, Ad.5-vectored nasal vaccines can protect animals against mucosal pathogens when systemic immunization fails, even though the latter induces a more robust systemic immune response [63, 69, 70]. The hypothesis that the focused mucosal immune response induced by nasal vaccination may greatly reduce the systemic burden (e.g., systemic inflammation) to unaffected internal tissues and organs was borne out by the finding that CD 103+ mucosal DCs can dampen inflammatory responses by fostering the conversion of naive T cells into Foxp3+ regulatory T cells [71].

The common adverse effects induced by systemically delivered Ad particles are liver damage and systemic toxicity owing to sequestration of Ad particles to the liver in large numbers following injection [72]. In contrast to parenteral injection, biodistribution of Ad is limited to the lung following intranasal administration [73] with no inflammation observed in any of the internal organs [68].

Owing to the proximity of the nasal cavity to the brain; it is crucial to determine whether Ad5 particles may induce inflammation and toxicity in the brain following nasal spray. Unlike influenza, which is associated with human neurological disorders [74], natural infection by Ad5 has not been reported to induce encephalitis in humans. Intranasal administration of ΔE1E3 Ad5 vectors into mice did not mediate transgene expression beyond the olfactory bulb, nor induction of inflammation in the brain [68]. It is thus conceivable that significant amounts of Ad5 cannot enter the brain following nasal delivery, Even though a small number of Ad5 particles may infiltrate into the brain on occasion, the nonreplicating Ad5 is likely to do less harm than its replicating wild-type counterpart due to its inability to amplify adverse effects through replication and late gene expression. The safety profile of the live-attenuated influenza virus vaccine (LAIV; known as FluMist® in the USA) [75] corroborates the hypothesis that the influenza virus-induced encephalitis [74] could be attributed to viral replication in the brain since LAIV can only replicate in the airway, where temperature is lower, but not within the brain, where it is too hot for the cold-adapted LAIV. The induction of herpes simplex encephalitis in TLR-3-deficient patients [76] suggests that it may be a common event for a small amount of virus to penetrate the brain through the olfactory tract and that an effective defense mechanism exists in immunocompetent people to arrest the virus before it replicates uncontrollably within the brain. Since natural infection by replicating wild-type Ad5 is not associated with encephalitis, nasal spray of nonreplicating Ad5 vector thus represents a driver in the pursuit of a safe carrier for vaccine delivery.

Even though it may have been a mistake to immunize humans via intramuscular injection of an Ad5-vectored HIV vaccine [58, 59], the ability of A.d5 to mobilize the CD4+ T-cell repertoire may be the driver, in part, for eliciting potent protective immunity against other pathogens [41, 53, 63, 77-79]. To date, intranasal administration of an Ad5-vectored influenza vaccine has induced seroconversion in human subjects without causing serious side effects in the presence of pre-existing Ad5 immunity [19]. The induction of sterile immunity against malaria [64] and seroconversion against influenza [19] in humans (Table 2) in conjunction with solid protective immunity induced in multiple animal models (Table 2) collectively prove the worth of Ad-vectored vaccines in preventing disease.

LAIV has been licensed for immunizing a subset of human populations (2-49 years of age in the USA) [75]. Like LAIV, it is conceivable that an Ad-vectored nasal vaccine may not be permitted to immunize the very young and the elderly, at least during the initial period before its safety profile is well established through large-scale field trials. Furthermore, nasal vaccination would not be recommended for people with respiratory illness (e.g., asthma). Whether pregnant women will be amenable to nasal vaccination using nonreplicating Ad particles remains to be seen.

Prospect for commercialization of Ad-vectored vaccines & other recombinant DNA-based vaccines. The nonreplicating ΔE1E3 Ad5-vectored vaccine without RCA contamination [35] can be classified as a variant of DNA vaccines because it consists of a linear DNA genome embedded in a protein capsid (FIG. 9) without the capability of replication in nonpermissive cells. Unlike naked DNA vaccines that have to be inoculated by trained personnel using a penetrating device such as the gene gun [80,81], syringe needle [82] or electroporator [83], Ad particles can autonomously penetrate cells along the mucosal barrier following nasal delivery [35]. Only a decade ago, DNA vaccines were an unproven novelty with limited acceptance in the scientific community, even though DNA vaccines forego many of the potential safety concerns related to contemporary vaccines and recombinant DNA technology can generate new vaccines rapidly and creatively at low costs [80, 82]. To date, four naked DNA vaccines have been licensed for animal use on a commercial scale [84]. An RCA-contaminated. Ad5 vector encoding p53 produced in 293 cells has been licensed for treating a large number of cancer patients in China since 2004 [85]. As the clinical picture is beginning to unfold as a result of years of increased usage and careful patient follow-up, it is conceivable that promising data may usher in a recombinant DNA-based vaccine age with the Ad-vectored vaccine as one of the essential tools in the public health arsenal against infectious disease.

Figure 11:
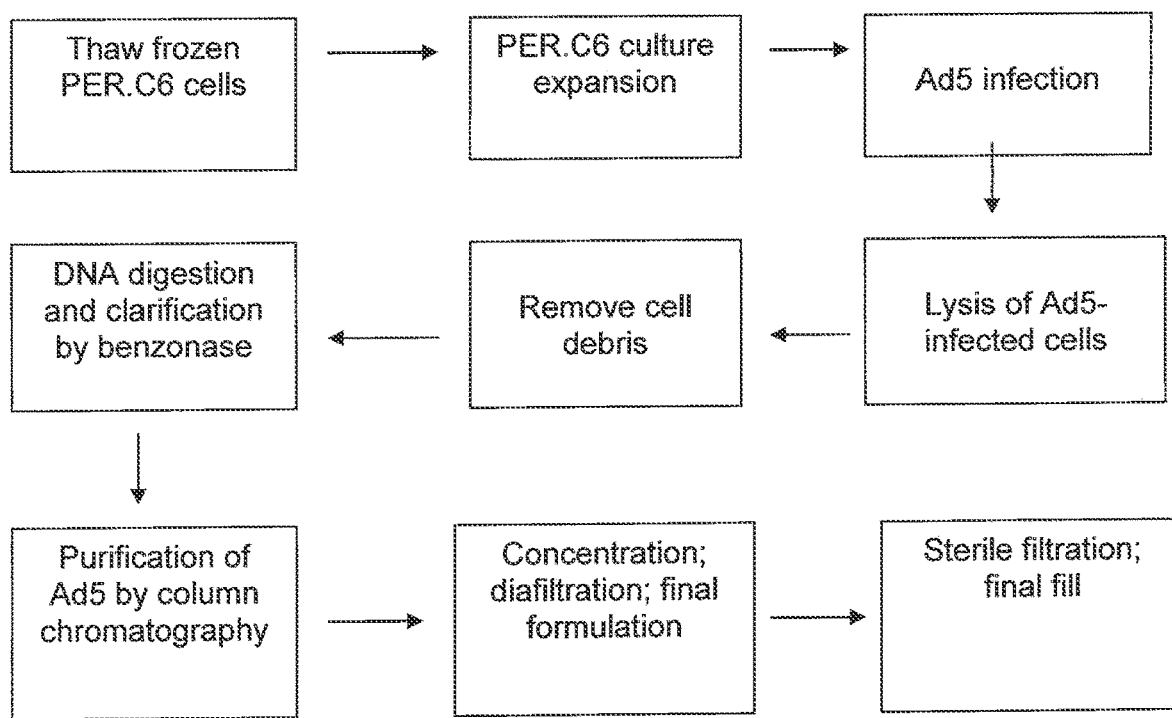
FIG. 11 depicts a manufacturing process for generating Adenoviral vectored vaccine.
Figure 12:
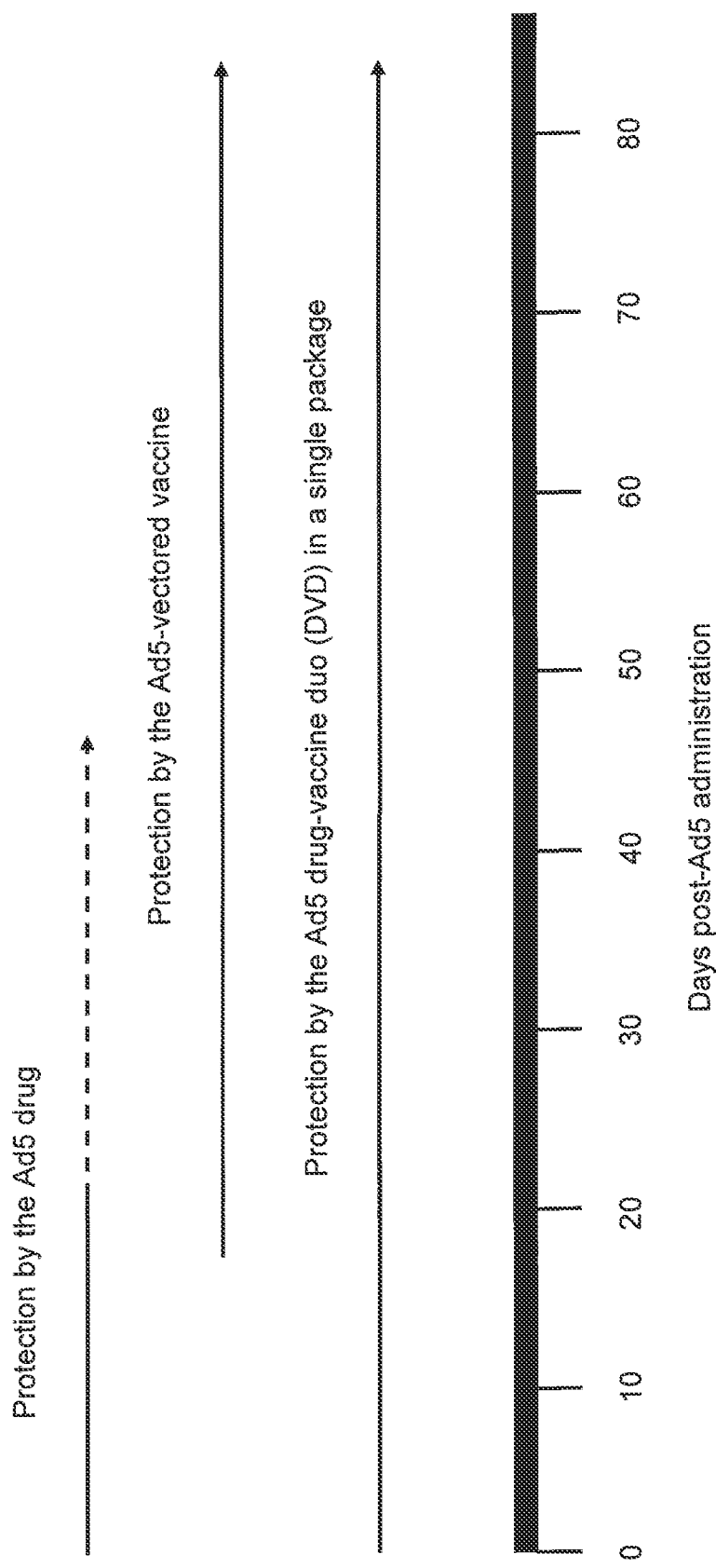
FIG. 12 depicts seamless protection conferred by intranasal administration of an Ad5-vectored drug-vaccine duo. It was recently demonstrated that intranasal instillation of AdE (an empty ΔE1E3 Ad5 particle without transgene) or AdNC.H.1.1 (a ΔE1E3 Ad5 vector encoding the A/New Caledonia/20/99 HA1 domain) can confer nearly immediate protection of mice against live influenza virus challenge [Zhang et al. PLoS ONE 6, e22605 (2011)]. The AdE-induced prophylactic therapy persisted in mice for at least 22 days, with partial decline of potency observed 47 days post-AdE administration. The AdNC.H1.1-induced protection was solid after 47 days. Solid timeframe of solid protection; dashed line: timeframe of partial protection. Since AdE-induced complete protection was observed for 22 days whereas partial protection was observed 47 days post-administration, it was assumed that the drug effects of DVD started declining after 22 days, as shown by the dashed line following the solid line. It was reported that an Ad5-vectored vaccine can elicit protective immunity as early as 2 weeks post-immunization [Boyer et al. Hum. Gene Ther. 16, 157-168 (2005)] as shown by a solid line starting on day 14 for the DVDs vaccine effects when Ad5 particles were inoculated on day 0. Results show that seamless protection against influenza may be achieved in mice by intranasal administration of an Ad5-vectored DVD since protective immunity can be elicited by the vaccine before the drug effects decline. Ad: Adenovirus; DVD: Drug-vaccine duo.
Figure 13:
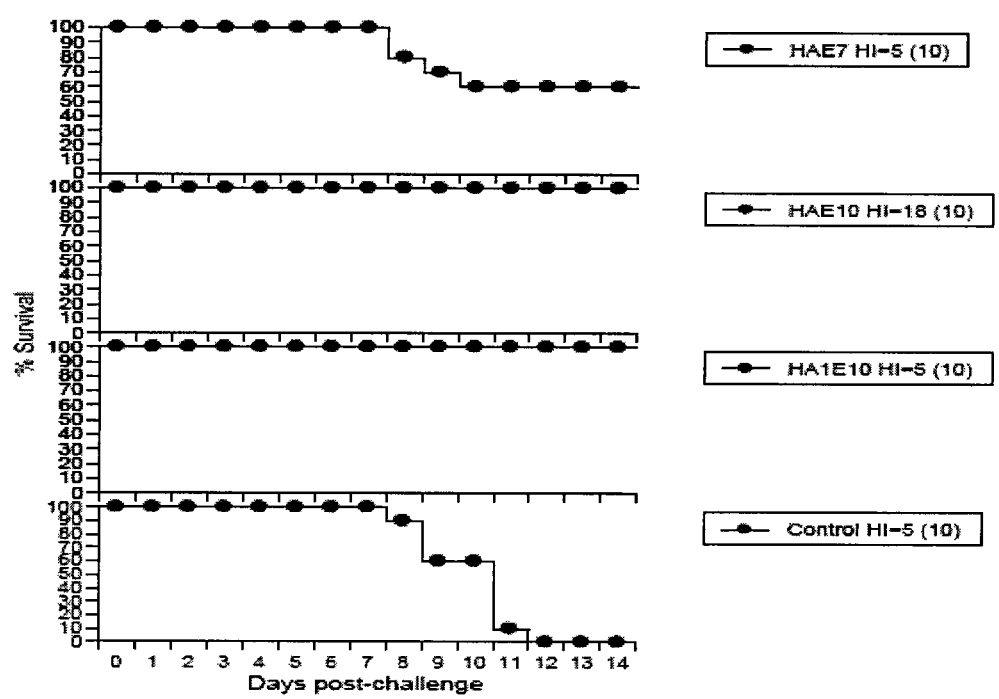
FIG. 13 depicts Ad5-vectored nasal vaccine protected mice against the A/VN/1203/04 (H5N1.) avian influenza virus. Mice were immunized i.n. on Day 0 and challenged with A/VN/1203/04 (H5N1) at a dose of $10 \times MLD_{50}$ ($10^{4.4}$ $EID_{50}$) at SRI on Day 63. HA, era. To date, over fifty-one human serotypes of adenoviruses have been identified (see, e.g., Fields et al., Virology 2, Ch. 67 (3d ed., Lippincott-Raven Publishers)). The adenovirus can be of serogroup A, B, C, E, or F. The human adenovirus can be a serotype 1 (Ad 1), serotype 2 (Ad2), serotype 3 (Ad3), serotype 4 (Ad4), serotype 6 (Ad6), serotype 7 (Ad7), serotype 8 (Ad8), serotype 9 (Ad9), serotype 10 (Ad10), serotype 11 (Ad11), serotype 12 (Ad12), serotype 13 (Ad13), serotype 14 (Ad14), serotype 15 (Ad15), serotype 16 (Ad16), serotype 17 (Ad17), serotype 18 (Ad18), serotype 19 (Ad19), serotype 19a (Ad19a), serotype 19p (Ad19p), serotype 20 (Ad20), serotype 21 (Ad21), serotype 22 (Ad22), serotype 23 (Ad23), serotype 24 (Ad24), serotype 25 (Ad25), serotype 26 (Ad26), serotype 27 (Ad27), serotype 28 (Ad28), serotype 29 (Ad29), serotype 30 (Ad30), serotype 31 (Ad31), serotype 32 (Ad32), serotype 33 (Ad33), serotype 34 (Ad34), serotype 35 (Ad35), serotype 36 (Ad36), serotype 37 (Ad37), serotype 38 (Ad38), serotype 39 (Ad39), serotype 40 (Ad40), serotype 41 (Ad41), serotype 42 (Ad42), serotype 43 (Ad43), serotype 44 (Ad44), serotype 45 (Ad45), serotype 46 (Ad46), serotype 47 (Ad47), serotype 48 (Ad48), serotype 49 (Ad49), serotype 50 (Ad50), serotype 51 (Ad51), or preferably, serotype 5 (Ad5), but are not limited to these examples.
Figure 14:
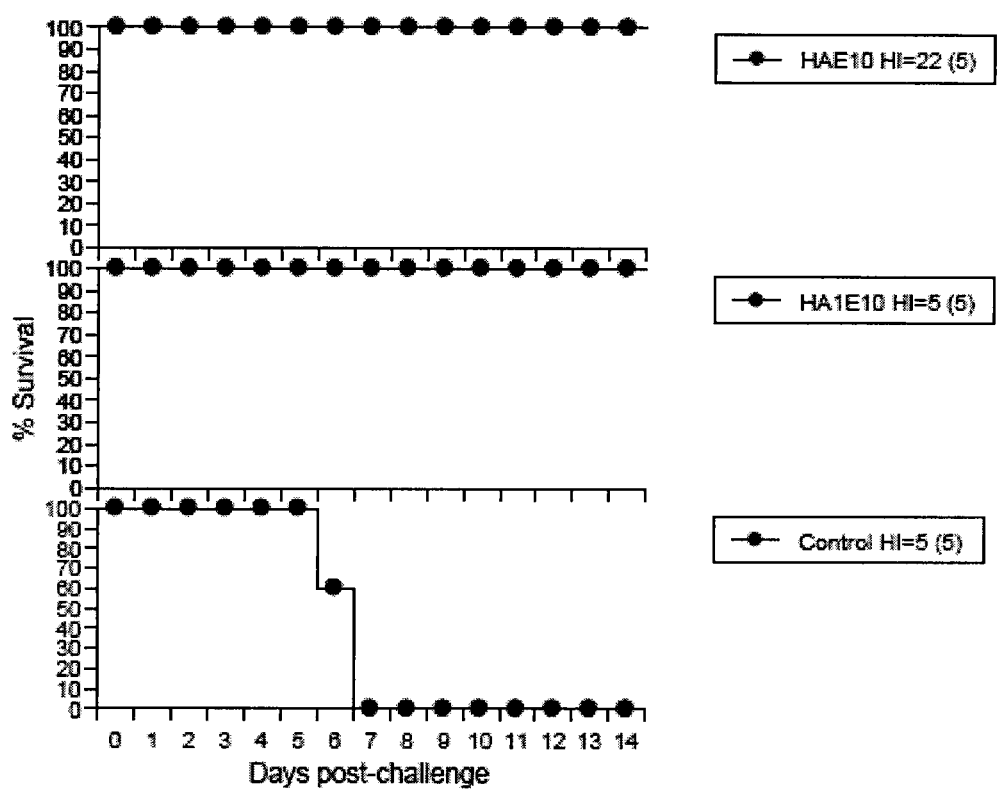

Maintenance of Ad vector viability during storage. In addition to safety and efficacy, the next generation of vaccines has to be less reliant on a chain of cold facilities to ensure wide dissemination of vaccines to the world's least affluent populations. To date, novel formulations have allowed Ad vectors to be stored in liquid buffer at 4° C. for at least a year [86]; at 45° C. in carbohydrate glass for at least 6 months [87]; or at 4° C. for at least a year as lyophilized dry powder [88]. Proprietary technologies for storing Ad particles at room temperature in either liquid or lyophilized form have also been developed at Stabilitech [202]. In summary, RCA-free. Ad5 vectors can be rapidly manufactured in serum-free PER.C6 suspension cells, purified easily by column chromatography, and formulated as final filled products that can be stored and shipped without a cold chain (FIG. 11).

Adenovirus-vectored drug-vaccine duo for conferring rapid & sustained, seamless protection against pathogens. Applicant recently demonstrated that intranasal administration but not intramuscular injection of $\Delta$E1E3 Ad5 particles, with or without a pathogen antigen encoded in the Ad5 genome, can confer prophylactic therapy against influenza before adaptive immunity is elicited [89]. An Ad5 vector encoding pathogen antigens may thus induce rapid and sustained seamless protection against a pathogen as a drug-vaccine duo (DVD). An Ad5-vectored influenza DVD confers a number of advantages when it is compared with licensed influenza vaccines (Table 4) and drugs (Table 5). It has been documented that administration of ΔE1E3 Ad5 particles into mice rapidly induces the production of a wide array of inflammatory cytokines and chemokines [56] including type I interferon (IFN-α and IFN-β) [90], impairs lung DCs [91], activates natural killer cells [92], induces production of antiviral nitric oxide [57], and triggers multifaceted interactions between Ad5 and blood proteins, platelets, macrophages, endothelial cells and respective parenchymal cells [56]. It is conceivable that multiple reactions induced by the ΔE1E3 Ad5 particles may combine to establish an anti-influenza state in the airway, thus creating a multidimensional defense barrier that cannot easily be bypassed by an influenza virus.

Although prophylactic influenza therapy can be performed by intranasal administration of complex bacterial lysates [93] or bacterial toxins [94], the bacterial component-induced anti-influenza state was very transient, with its protective effects declining within a few days post-therapy [93,94]. The finding that Ad5-induced protective effects could persist for at least 3 weeks with only a partial decline observed on day 47 in a single-dose regimen [89] suggests that the underlying mechanisms between bacterial component- and ΔE1E3-Ad5-induced anti-influenza states may differ. Notably, only the Ad5-mediated therapy would allow sufficient time for the DVD's vaccine component to elicit adaptive immunity before its drug effects decline (FIG. 12). Furthermore, administration of a digestive tract-associated bacterial toxin into the respiratory tract as an influenza drug [94] violates a core principle in evolutionary medicine by surprising the immune system, and this unnatural regimen has been associated with the induction of Bell's palsy in human subjects [7,8].

Influenza virus is insidious in mutating into drug-resistant strains when it is inhibited by an influenza drug (e.g., the M2 ion channel blocker [amantadine, rimantadine] or the neuraminidase inhibitor [oseltamivir, zanamivir]) [95]. Unlike contemporary influenza drugs, the Ad5-vectored DVD conceivably changes the habitat in the respiratory tract without directly effecting the influenza virus; hence the Ad5 particle confers no mutational pressure on influenza virus for inducing drug resistance. In contrast to the oseltamivir-induced suppression of mucosal immunity with the risk to enhance vulnerability to subsequent mucosal pathogen infections in drugged animals [96], the Ad5-vectored DVD enhances protective mucosal innate immunity, at least in the influenza setting [89]. Since the licensed nasal LAIV (e.g., FluMist) contains live influenza virus [35], coach inistration of LAIV with an influenza drug is counter-productive because the drug would disable the vaccine by killing live influenza viruses. The Ad5-vectored DVD is not only compatible with a licensed influenza drug due to its lack of the drug targets (e.g., ion channel or neuraminidase) (Table 4), but it also confers prophylactic therapy as a drug by itself in addition to its vaccine capacity (Table 5) [89].

It is unlikely lat influenza is the only disease that can be arrested by Ad5 particles; it is also unlikely that Ad5 can counteract all diseases as a panacea. The findings merely show that a single intranasal administration of Ad5-vectored DVD can confer prophylactic therapy against at least a subset of mucosal respiratory pathogens for many weeks in a preclinical animal model and use of the DVD should be unable to induce drug resistance. Subsequent elicitation of sustained protective immunity by the DVD's vaccine component fortifies efficacy. The development of a DVD platform will conceivably foster the development of novel clinical strategies in a wide variety of disease settings.

Mass immunization of animals with adenovirus-vectored vaccines. As shown in Table 2, Ad-vectored vaccines have been developed to mass immunize farm animals as well as wildlife. Notably, chickens can be immunized against avian influenza (possibly other poultry diseases as well) by intramuscular injection [78], in ovo administration [97-101], or aerosol spray [102,103] of human Ad5 vectors encoding avian influenza virus hemagglutinin. The versatility of Ad5-vectored vaccines in mass immunization of poultry thus outperforms that of other poultry vaccines. Pigs have also been successfully immunized with Ad5-vectored vaccines [104,105]. An oral canine Ad-vectored rabies vaccine has been developed as a bait to mass immunize wildlife [106]. Overall, Ad-vectored vaccines are emerging as a promising tool in mass immunization programs.

Conclusion. Evidence shows that Ad-vectored vaccines and the new DVD provide a potentially revolutionary approach, allowing precisely designed, easily manufactured and highly effective DVD to confer rapid and sustained, seamless protection of humans and animals in a wide variety of disease settings, without the side-effect profile, shelf instability or manufacturing challenges that other approaches have seen.

Expert commentary. To further boost vaccine coverage worldwide, it is urgent to develop a new generation of vaccines that can be rapidly manufactured at low costs and mass administered by nonmedical personnel without the requirement for a cold chain. Ad5-vectored vaccines comply with these criteria. The development of a DVD platform may potentially change the medical landscape by consolidating vaccines and drugs into a single package that is not impaired by drug resistance.

Five-year view. Two human Phase I clinical trials of Ad5-vectored nasal influenza vaccines have been completed with promising results. Challenge of human subjects with live influenza viruses following nasal spray of an A.d5-vectored DVD is expected to be performed within 5 years. Ad5-vectored poultry vaccines are expected to enter the commercial market within 5 years.

Key issues. There is an urgent need to develop a new generation of vaccines that can be rapidly manufactured and mass administered by nonmedical personnel during a crisis. Replication-competent adenovirus (RCA)-free adenovirus (Ad)5-vectored vaccines can be produced rapidly at low costs from PER.C6 suspension cells in serum-free medium in response to an escalation in demand. RCA-free Ad5-vectored vaccines can be mass administered to people by nasal spray, as well as to poultry by automated in ovo administration and aerosol spray. Wildlife can be mass immunized by baits containing canine Ad-vectored oral vaccines. Ad-vectored vaccines can induce highly specific immune interventions based on well-defined antigens that are the focus of specific immune reactivity. There should not be any safety concerns for nasal administration of an RCA-free Ad5 vector into people since the vector is nonreplicating and the procedure is in compliance with evolutionary medicine. There should not be any safety concerns for mass immunization of poultry by an Ad5 vector since chicken cells do not support replication of human Ad5. It is conceivable that chickens will rapidly eliminate Ad5 after the immune repertoire is mobilized toward a beneficial immune protection following vaccination. A DNA-primed/Ad.5-boosted malaria vaccine successfully protected human subjects against live malaria sporozoite challenge following mosquito feeding. An Ad5-vectored, nasal vaccine was serendipitously shown to confer rapid protection against influenza in a drug-like manner. Development of a drug-vaccine duo that consolidates drug and vaccine into a single package that is not impaired by drug resistance would fundamentally change the way influenza drugs and vaccines are prepared. Overall, more and more adverse effects induced by systemic vaccination have been identified. Non-invasive mucosal immunization is safer and more effective in conferring protection against mucosal pathogens than its systemic counterpart.

Tables

TABLE 2

Examples of protective immunity induced by adenovirus-vectored vaccines against live pathogens in animal models

| Vaccine | Pathogen antigen expressed from Ad | Route | Animal model | Challenge | Ref. |
|---|---|---|---|---|---|
| Ad26-primed/Ad35-boosted | Ebolavirus GP | im. | Nonhuman primate | Ebolavirus | [107] |
| Ad5 | Ebolavirus GP | im. | Nonhuman primate | Ebolavirus | [108 |
| Ad5 | Angola Marburg virus OP | im. | Nonhuman primate | Angola Marburg virus | [109] |
| BCG-primed/Ad5-boosted | Ag85A | in., im. | Guinea pig | *Mycobacterium tuberculosis* | [110] |
| Ad5 | PA | im. | Mouse | *Bacillus anthracis* Sterne spore | [111] |
| Ad5 | Avian influenza virus H5 HA | in., im. | Mouse | Avian influenza virus | [77, 78] |
| Influenza vaccine-primed/Ad5-boosted | Influenza virus HA | im. | Mouse | Heterosubtypic influenza virus | [112] |
| Ad5 | Avian influenza virus H5 HA | im., in ovo, ovular | Chicken | Avian influenza virus | [78, 97, 98, 102] |

TABLE 2-continued Examples of protective immunity induced by adenovirus-vectored vaccines against live pathogens in animal models

| Vaccine | Pathogen antigen expressed from Ad | Route | Animal model | Challenge | Ref. |
|---|---|---|---|---|---|
| Ad5 | Influenza virus HA/nucleoprotein | im. | Pig | Swine influenza virus | [104] |
| Ad5 | Hantavirus nucleocapsid/GP | im. | Hamster | Hantavirus | [113] |
| Ad5 | Botulinum neurotoxin C-fragment | in. | Mouse | Botulinum neurotoxin | [114] |
| Ad5 | Measles virus fusion protein/HA | in., im. | Cotton rat | Measles virus | [70] |
| Canine Ad | Rabies virus GP | Oral | Raccoon, skunk | Rabies virus | [106] |
| Ad5 | V antigen | im. | Mouse | *Yersinia pestis* | [115] |

Ad: Adenovirus;
BCG: *Bacillus* Calmette-Guérin;
GP: Glycoprotein;
HA: Hemagglutinin;
im.: Intramuscular;
in.: Intranasal;
PA: Protective antigen.

TABLE 3

Examples of human clinical trials of adenovirus and adenovirus-vectored vaccines

| Vaccine | Pathogen antigen expressed from Ad | Route | Challenge | Ref. |
|---|---|---|---|---|
| Ad4 and Ad7 | None | Oral | Natural infection by Ad | [31] |
| DNA-primed/Ad5-boosted | CSP/AMA1 | im. | Malaria sporozoite | [64] |
| Ad5 | HIV-1 gag/pol/nef | im. | Natural infection by HIV-1 | [58, 59] |
| DNA-primed/Ad5-boosted | HIV-1 gag/pol/env | im. | None | [203] |
| Ad5-primed/Ad5-boosted | HIV-1 gag | im. | None | [203] |
| Ad5-primed/NYVAC-boosted; NYVAC-primed/ | HIV-1 gag/pol/env/nef | im. | None | [203] |
| Ad5-boosted Ad5 | Influenza virus H1 HA | in. and skin patch | None | [203] |
| Ad4-primed/Ad4-boosted | Avian influenza virus H5 HA | Oral | None | [203] |
| Encapsulated and adjuvanted Ad5 | Avian influenza virus H5 HA | Oral | None | [203] |
| Ad5 | Mycobacterium tuberculosis 85A | im. | None | [203] |
| BCG-primed/Ad35-boosted | M. tuberculosis 85A/85B/10.4 | im. | None | [203] |

Ad: Adenovirus;
AMA1: Apical membrane antigen 1;
BCG: *Bacillus* Calmette-Guérin;
CSP: Circumsporozoite protein;
HA: Hemagglutinin;
im.: Intramuscular;
in.: Intranasal.

TABLE 4

Rational to develop an adenovirus serotype 5 vectored influenza drug-vaccine duo in light of licensed influenza vaccines.

| Vaccine | Requirement to propagate an influenza virus | Requirement to use embryonated chicken eggs as the substrate | Production speed | Replication post-administration | Mode of administration | Concomitant use with licensed influenza drugs |
|---|---|---|---|---|---|---|
| TIV | Yes | Yes | Slow | No** | Needle injection | Yes** |
| LAIV* | Yes | Yes | Slow | Yes | Nasal Spray** | No |
| DVD [89] | No** | No** | Fast** | No** | Nasal Spray** | Yes** |

TABLE 4-continued

Rational to develop an adenovirus serotype 5 vectored influenza drug-vaccine duo in light of licensed influenza vaccines.

|

13. Witte M F, Geurts J J, de Vries H E, van der Valk P, van Horssen J. Mitochondrial dysfunction: a potential link between neuroinflammation and neurodegeneration? Mitochondrion 10, 411-418 (2010).
14. Gallichan W S, Rosenthal K L. Long-lived cytotoxic T lymphocyte memory in mucosal tissues after mucosal but not systemic immunization. J. Exp. Med. 184, 1879-1890 (1996).
15. Saurer L, McCullough K C, Summerfield A. In vitro induction of mucosa-type dendritic cells by all-trans retinoic acid. J. Immunol. 179, 3504-3514 (2007).
16. Molenaar R, Greuter M, van der Marel A P et al. Lymph node stromal cells support dendritic cell-induced gut-homing of T cells. J. Immunol. 183, 6395-6402 (2009).
17. Tang D C, Van Kampen K R. Toward the development of vectored vaccines in compliance with evolutionary medicine. Expert Rev. Vaccines 7(4), 399-402 (2008).
18. Karron R A, Talaat K, Luke C et al. Evaluation of two live attenuated cold adapted H5N1 influenza virus vaccines in healthy adults. Vaccine 27, 4953-4960 (2009).
19. Van Kampen K R, Shi. Z, Gao P et al. Safety and immunogenicity of adenovirus vectored nasal and epicutaneous influenza vaccines in humans. Vaccine 23, 1029-1036 (2005).
20. Tang D C, Shi Z, Curiel D T. Vaccination onto bare skin. Nature 388, 729-730 (1997).
21. Zhang J, Shi Z, Kong F K et al. Topical application of *Escherichia coli*-vectored vaccine as a simple method for eliciting protective immunity. Infect. Immun. 74, 3607-3617 (2006).
22. Glenn G M, Taylor D N, Li X et al. Transcutaneous immunization: a human vaccine delivery strategy using a patch. Nat. Med. 6, 1403-1406 (2000).
23. Sullivan S P, Koutsonanos D G, del Pilar Martin M et al. Dissolving polymer microneedle patches for influenza vaccination. Nat. Med. 16, 915-920 (2010).
24. Kaplan D H. In vivo function of Langerhans cells and dermal dendritic cells. Trends Immunol, 31, 446-451 (2010).
25. Soloff A C, Barratt-Boyes S M. Enemy at the gates: dendritic cells and immunity to mucosal pathogens. Cell Res. 20, 872-885 (2010).
26. Brandes M, Willmann K, Moser B. Professional antigen-presentation function by human gammadelta T cells. Science 309, 264-268 (2005).
27. Feng T, Cong Y, Qin H, Benveniste E N, Elson C O. Generation of mucosal dendritic cells from bone marrow reveals a critical role of retinoic acid. J. Immunol. 185, 5915-5925 (2010).
28. Kaufman D R, Bivas-Benita M, Simmons N L, Miller D, Barouch D H. Route of adenovirus-based HIV-1 vaccine delivery impacts the phenotype and trafficking of vaccine-elicited CD8+ T lymphocytes. J. Virol. 84, 5986-5996 (2010)
29. San Martin C, Burnett R M. Structural studies on adenoviruses. Curr. Top. Microbiol. Immunol. 272, 57-94 (2003).
30. Lichtenstein D L, Wold W S. Experimental infections of humans with wild-type adenoviruses and with replication competent adenovirus vectors: replication, safety, and transmission. Cancer Gene Ther. 11, 819-829 (2004).
31. Howell M R, Nang R N, Gaydos C A, Gaydos J C. Prevention of adenoviral acute respiratory disease in Army recruits: cost-effectiveness of a military vaccination policy. Am. J. Prev. Med. 14, 168-175 (1998).
32. Haj-Ahmad Y, Graham F L. Development of a helper-independent human adenovirus vector and its use in the transfer of the herpes simplex virus thymidine kinase gene. J. Virol. 57, 267-274 (1986).
33. Zhu J, Grace M, Casale J et al. Characterization of replication-competent adenovirus isolates from large-scale production of a recombinant adenoviral vector. Hum. Gene Ther. 10, 113-121 (1999).
34. Fallaux F J, Bout A, van der Velde I et al. New helper cells and matched early region 1-deleted adenovirus vectors prevent generation of replication-competent adenoviruses. Hum. Gene Ther. 9, 1909-1917 (1998).
35. Tang D C, Zhang J, Toro H, Shi. Z, Van Kampen K R. Adenovirus as a carrier for the development of influenza virus-free avian influenza vaccines. Expert Rev. Vaccines 8, 469-481 (2009).
36. Wang L, Cheng C, Ko S Y et al. Delivery of human immunodeficiency virus vaccine vectors to the intestine induces enhanced mucosal cellular immunity. J. Virol. 83, 7166-7175 (2009).
37. Tang J, Olive M, Champagne K et al. Adenovirus hexon epitope is recognized by most adults and is restricted by HLA DP4, the most common class II allele, Gene Ther. 11, 1408-1415 (2004).
38. Nwanegbo E, Vardas E, Gao W et al. Prevalence of neutralizing antibodies to adenoviral serotypes 5 and 35 in the adult populations of The Gambia, South Africa, and the United States. Clin. Diagn, Lab. Immunol, 11, 351-357 (2004).
39. Barouch D H, Kik S V, Weverling G J et al. International seroepidemiology of adenovirus serotypes 5, 26, 35, and 48 in pediatric and adult populations. Vaccine 29, 5203-5209 (2011).
40. Yang Y, Nunes F A, Berencsi K et al. Cellular immunity to viral antigens limits E1-deleted adenoviruses for gene therapy. Proc. Natl Acad, Sci, USA 91, 4407-4411 (1994).
41. Croyle M A, Patel A, Tran K N et al. Nasal delivery of an adenovirus-based vaccine bypasses pre-existing immunity to the vaccine carrier and improves the immune response in mice. PLoS ONE 3, e3548 (2008).
42. Stone D, Liu Y, Li Z Y et al. Comparison of adenoviruses from species B, C, E, and F after intravenous delivery. Mol. Ther. 15, 2146-2153 (2007).
43. Sharma A, Bangari D S, Tandon M et al. Comparative analysis of vector biodistribution, persistence and gene expression following intravenous delivery of bovine, porcine and human adenoviral vectors in a mouse model. Virology 386, 44-54 (2009).
44. Roy 5, Medina-Jaszek A, Wilson M J et al. Creation of a panel of vectors based on ape adenovirus isolates. J. Gene Med. 13, 17-25 (2011).
45. Patel A, Tikoo 5, Kobinger G. A porcine adenovirus with low human seroprevalence is a promising alternative vaccine vector to human adenovirus 5 in an H5N1 virus disease model. PLoS ONE 5, e15301 (2010).
46. Chen E C, Yagi S, Kelly K R et al. Crossspecies transmission of a novel adenovirus associated with a fulminant pneumonia outbreak in a new world monkey colony. PLoS Pathog. 7, e1002155 (2011).
47. Seto J, Walsh M P, Metzgar D, Seto D. Computational analysis of adenovirus serotype 5 (HAdV-C5) from an HAdV coinfection shows genome stability after 45 years of circulation. Virology 404, 180-186 (2010).
48. Boyer J L, Sofer-Podesta. C, Ang J et al. Protective immunity against a lethal respirato Yersinia pestis challenge induced by V antigen or the F1 capsular antigen incorporated into adenovirus capsid. Hum. Gene Ther. 21, 891-901 (2010).

49. Worgall S, Krause A, Qiu J et al. Protective immunity to *Pseudomonas aeruginosa* induced with a capsid-modified adenovirus expressing *P. aeruginosa* OprF. J. Virol. 81, 13801-13808 (2007).
50. Osada T, Yang X Y, Hartman Z C et al. Optimization of vaccine responses with an E1, E2b and E3-deleted Ad5 vector circumvents pre-existing anti-vector immunity. Cancer Gene Ther. 16, 673-682 (2009).
51. Gabitzsch E S, Xu Y, Yoshida L H et al. Novel adenovirus type 5 vaccine platform induces cellular immunity against HIV-1 Gag, Pol, Nef despite the presence of Ad5 immunity, Vaccine 27, 6394-6398 (2009).
52. Parks R J, Chen L, Anton M et al, A helper-dependent adenovirus vector system: removal of helper virus by Cre-mediated excision of the viral packaging signal. Proc. Natl Acad. Sci, USA 93, 13565-13570 (1996).
53. Shi Z, Zen; NI, Yang G et al. Protection against tetanus by needle-free inoculation of adenovirus-vectored nasal and epicutaneous vaccines. J. Virol. 75, 11474-11482 (2001).
54. Song K, Bolton D L, Wilson R L et al. Genetic immunization in the lung induces potent local and systemic immune responses. Proc. Natl Acad. Sci. USA 107, 22213-22218 (2010).
55. Raper S E, Chirmule N, Lee F S et al, Fatal systemic inflammatory response syndrome in a ornithine transcarbamylase deficient patient following adenoviral gene transfer. Mot. Genet. Metab. 80, 148-158 (2003).
56. Hartman Z C, Appledore D M, Amalfitano A. Adenovirus vector induced innate immune responses: impact upon efficacy and toxicity in gene therapy and vaccine applications. Virus Res. 132, 1-14 (2008).
57. Higashi moto Y, Yamagata Y, Itoh H. Complex effect of adenovirus early region proteins on innate immune system. Inflamm. Allergy Drug Targets 5, 229-237 (2006).
58. Buchbinder S P, Mehrotra D V, Duerr A et al. Efficacy assessment of a cell-mediated. immunity HIV-1 vaccine (the Step study): a double-blind, randomised, placebo controlled, test-of-concept trial. Lancet 372, 1881-1893 (2008).
59. McElrath M J, De Rosa S C, Moodie Z et al. HIV-1 vaccine-induced immunity in the test-of-concept Step Study: a case-cohort analysis. Lancet 372, 1894-1905 (2008).
60. Appledorn D M, Aldhamen Y A, Godbehere S, Seregin S S, Amalfitano A, Sublingual administration of an adenovirus serotype 5 (Ad5)-based vaccine confirms Toll-like receptor agonist activity in the oral cavity and elicits improved mucosal and systemic cell-mediated responses against HIV antigens despite preexisting Ad5 immunity. Clin. Vaccine Immunol. 18, 150-160 (2011).
61. Benlahrech A, Harris J, Meiser A et al. Adenovirus vector vaccination induces expansion of memory CD4 T cells with a mucosal homing phenotype that are readily susceptible to HIV-1. Proc. Natl Acad. Sci. USA 106, 19940-19945 (2009).
62. Joseph A, Itskovitz-Cooper N, Samira S et al. A new intranasal influenza vaccine based on a novel polycationic lipid-ceramide carbamoyl-spermine (CCS) I. Immunogenicity and efficacy studies in mice. Vaccine 24, 3990-4006 (2006).
63. Wang J, Thorson L, Stokes R W et al. Single mucosal, but not parenteral, immunization with recombinant adenoviral based vaccine provides potent protection from pulmonary tuberculosis. J. Immunol. 173, 6357-6365 (2004).
64. Ockenhouse C. Prime boost regimens of DNA and adenovirus-vectored malaria vaccines: lessons learned from preclinical and clinical studies. Presented at: Conference of Gene Based Vaccines. Vienna, Austria, 13-14 Sep. 2010.
65. McWilliam A S, Nelson D J, Holt P G. The biology of airway dendritic cells. Immunol. Cell Biol. 73, 405-413 (1995).
66. Brandtzaeg P. Potential of nasopharynx associated lymphoid tissue for vaccine responses in the airways. Am. J. Respir. Crit. Care Med. 183, 1595-1604 (2011).
67. Lubeck M D, Natuk R J, Chengalvala M et al. Immunogenicity of recombinant adenovirus-human immunodeficiency virus vaccines in chimpanzees following intranasal administration. AIDS Res. Hum. Retroviruses 10, 1443-1449 (1994).
68. Lemiale F, Kong W P, Akyurek I, M et al. Enhanced mucosal immunoglobulin A response of intranasal adenoviral vector human immunodeficiency virus vaccine and localization in the central nervous system. J. Virol. 77, 10078-10087 (2003).
69. Gallichan W S, Rosenthal K L. Long-term immunity and protection against herpes simplex virus type 2 in the murine female genital tract after mucosal but not systemic immunization. J. Infect. Dis. 177, 1155-1161 (1998).
70. Lobanova L M, Baig T T, Tikoo S K, Zakhartchouk A N. Mucosal adenovirus-vectored vaccine for measles. Vaccine 28, 7613-7619 (2010).
71. del Rio M L, Bernhardt G, Rodriguez-Barbosa J I, Förster R. Development and functional specialization of CD103+ dendritic cells. Itnmunol. Rev. 234, 268-281 (2010).
72. Zhang Z, Krimmel J, Zhang Z, Hu Z, Seth P. Systemic delivery of a novel liverdetargeted oncolytic adenovirus causes reduced liver toxicity but maintains the antitumor response in a breast cancer bone metastasis model. Hum. Gene Ther. (In Press) (2011).
73. Li C, Ziegler R J, Cherry M et al. Adenovirus-transduced lung as a portal for delivering alpha-galactosidase A into systemic circulation for Fabry disease. Mol. Ther. 5, 745-754 (2002).
74. Toovey S. Influenza-associated central nervous system dysfunction: a literature review. Travel Med. Infect. Dis. 6, 114-124 (2008).
75. Carter N J, Curran M P. Live attenuated influenza vaccine (F uMist®; Fluenez™): a review of its use in the prevention of seasonal influenza in children and adults. Drugs 71, 1591-1622 (2011).
76. Zhang S Y, Jouanguy E, Ugolini S et al. TLR3 deficiency in patients with herpes simplex encephalitis. Science 317, 1522-1527 (2007).
77. Hoelscher M A, Garg S, Bangari D S et al, Development of adenoviral-vector-based pandemic influenza vaccine against antigenically distinct human H5N1 strains in mice. Lancet 367, 475-481 (2006).
78. Gao W, Soloff A C, Lu X et al. Protection of mice and poultry from lethal H5N1 avian influenza virus through adenovirus-based immunization. J. Virol. 80, 1959-1964 (2006).
79. Xiang Z Q, Yang Y, Wilson J M, Ertl H C. A replication-defective human adenovirus recombinant serves as a highly efficacious vaccine carrier. Virology 219, 220-227 (1996).
80. Tang D C, DeVit M, Johnston S A. Genetic immunization is a simple method for eliciting an immune response. Nature 356, 152-154 (1992).

81. Jones S, Evans K, McElwaine-Johnn H et al. DNA vaccination protects against an influenza challenge in a double-blind randomised placebo-controlled Phase 1b clinical trial. Vaccine 27, 2506-2512 (2009).
82. Ulmer J B, Donnelly J J, Parker S E et al. Heterologous protection against influenza by injection of DNA encoding a viral protein. Science 259, 1745-1748 (1993).
83. van Drunen Littel-van den Hurk S, Hannaman D. Electroporation for DNA immunization: clinical application. Expert Rev. Vaccines 9(5), 503-517 (2010).
84. Kutzler M A, Weiner D B. DNA vaccines: ready for prime time? Nat. Rev. Genet. 9, 776-788 (2008).
85. Peng Z. Current status of gendicine in China: recombinant human Ad-p53 agent for treatment of cancers. Hum. Gene Ther. 16, 1016-1027 (2005).
86. Evans R K, Nawrocki D K, Isopi L A et al. Development of suable liquid formulations for adenovirus-based vaccines. J. Pharm. Sci. 93, 2458-2475 (2004).
87. Alcock R, Cottingharn M G, Bonier C S et al. Long-term thermostabilization of live pox viral and adenoviral vaccine vectors at supraphysiological temperatures in carbohydrate glass. Sci, Transl. Med. 2, 19ra12 (2010).
88. Croyle M A, Cheng X, Wilson J M. Development of formulations that enhance physical stability of viral vectors for gene therapy. Gene Ther. 8, 1281-1290 (2001).
89. Zhang J, Tarbet E B, Feng T et al. Adenovirus-vectored drug-vaccine duo as a rapid-response tool for conferring seamless protection against influenza. PLoS ONE 6, e22605 (2011).
90. Yamaguchi T, Kawabata K, Kouyama E et al. Induction of type I interferon by adenovirus-encoded small RNAs. Proc. Natl Acad. Sci. USA 107, 17286-17291 (2010).
91. Thiele A T, Sumpter T L, Walker J A et al. Pulmonary immunity to viral infection: adenovirus infection of lung dendritic cells renders T cells nonresponsive to interleukin-2. J. Virol. 80, 1826-1836 (2006).
92. Zhu J, Huang X, Yang Y. A critical role for type I IFN-dependent NK cell activation in innate immune elimination of adenoviral vectors in vivo. Mol. Ther. 16, 1300-1307 (2008).
93. Tuvim M J, Evans S E, Clement C G, Dickey B F, Gilbert B E. Augmented lung inflammation protects against influenza A pneumonia. PLoS ONE 4, e4176 (2009).
94. Norton E B, Clements J D, Voss T G, Cardenas-Freytag L. Prophylactic administration of bacterially derived immunomodulators improves the outcome of influenza virus infection in a murine model. J. Virol. 84, 2983-2995 (2010).
95. Poland G A, Jacobson R M. Ovsyannikova I G. Influenza virus resistance to antiviral agents: a plea for rational use. Clin. Infect. Dis. 48, 1254-1256 (2009).
96. Takahashi E, Kataoka K, Fujii K et al. Attenuation of inducible respiratory immune responses by oseltamivir treatment in mice infected with influenza A virus. Microbes Infect. 12, 778-783 (2010).
97. Toro H, Tang D C, Suarez D L et al. Protective avian influenza in ovo vaccination with non-replicating human adenovirus vector. Vaccine 25, 2886-2891 (2007).
98. Toro H, Tang D C, Suarez D L, Zhang J, Shi Z. Protection of chickens against avian influenza with non-replicating adenovirus-vectored vaccine. Vaccine 26, 2640-2646 (2008).
99. Toro H, Tang D C. Protection of chickens against avian influenza with non-replicating adenovirus-vectored vaccine. Poult. Sci. 88, 867-871 (2009).
100. Avakian A P, Poston R M, Kong F K, Van Kampen K R, Tang D C. Automated mass immunization of poultry: the prospect for nonreplicating human adenovirus-vectored in ovo vaccines. Expert Rev. Vaccines 6(3), 457-465 (2007),
101. Singh S, Toro H, Tang D C et al. Nonreplicating adenovirus vectors expressing avian influenza virus hemagglutinin and nucleocapsid proteins induce chicken specific effector, memory and effector memory CD8+ T lymphocytes. Virology 405, 62-69 (2010).
102. Toro H, Suarez D L. Tang D C, van Ginkel F W, Breedlovea C. Avian influenza mucosal vaccination in chickens with replication-defective recombinant adenovirus vaccine. Avian Dis. 55, 43-47 (2011).
103. van Ginkel F, Tang D C, Gulley S L, Toro H. Induction of mucosal immunity in the avian Harderian gland with a replication deficient Ad5 vector expressing avian influenza. H5 hemagglutinin. Dev. Comp. Immunol. 33, 28-34 (2009).
104. Wesley R D, Tang M, Lager K M. Protection of weaned pigs by vaccination with human adenovirus 5 recombinant viruses expressing the hemagglutinin and the nucleoprotein of H3N2 swine influenza virus. Vaccine 22, 3427-3434 (2004).
105. Toro H, van Ginkel F W, Tang D C et al. Avian influenza vaccination in chickens and pigs with replication-competent adenovirus-free human recombinant adenovirus 5. Avian Dis. 54(1 Suppl.), 224-231 (2010).
106. Henderson H, Jackson F, Bean K et al. Oral immunization of raccoons and skunks with a canine adenovirus recombinant rabies vaccine. Vaccine 27, 7194-7197 (2009).
107. Geisbert T W, Bailey M, Hensley L et al. Recombinant adenovirus serotype 26 (Ad26) and Ad35 vaccine vectors bypass immunity to Ad5 and protect nonhuman primates against ebolavirus challenge. J. Virol. 85, 4222-4233 (2011).
108. Pratt W D, Wang D, Nichols D K et al. Protection of nonhuman primates against two species of Ebola virus infection with a single complex adenovirus vector, Clin. Vaccine Immunol. 17, 572-581 (2010).
109. Geisbert T W, Bailey M, Geisbert J B et al. Vector choice determines irnmunogenicity and potency of genetic vaccines against Angola Marburg virus in nonhuman primates. J. Virol. 84, 10386-10394 (2010).
110. Xing Z, McFarland C T, Sallenave J M et al. Intranasal mucosal boosting with an adenovirus-vectored vaccine markedly enhances the protection of BCG-primed guinea pigs against pulmonary tuberculosis, PLoS ONE 4, e5856 (2009).
111. McConnell M J, Hanna P C, Imperiale M J. Adenovirus-based prime-boost immunization for rapid vaccination against anthrax. Mol. Ther. 15, 203-210 (2007).
112. Wei C J, Boyington J C, McTamney P M et al. Induction of broadly neutralizing H1N1 influenza antibodies by vaccination. Science 329, 1060-1064 (2010).
113. Safronetz D, Hegde N R, Ebihara H et al. Adenovirus vectors expressing hantavirus proteins protect hamsters against lethal challenge with andes virus. J. Virol, 83, 7285-7295 (2009),
114. Xu Q, Pichichero M E, Simpson L L et al. An adenoviral vector-based mucosal vaccine is effective in protection against botulism. Gene Ther. 16, 367-375 (2009).
115. Chiuchiolo M J, Boyer J L, Krause A et al. Protective immunity against respiratory tract challenge with Yersinia pestis in mice immunized with an adenovirus-based vaccine vector expressing V antigen. J. Infect. Dis. 194, 1249-1257 (2006).

116. Fox J L. FDA, producers moving toward mammalian cell-based flu vaccines. Microbe 1, 54-55 (2006).
117. Boyer i L, Kobinger G, Wilson J M, Crystal R G. Adenovirus-based genetic vaccines for biodefense. Hum. Gene Ther. 16, 157-168 (2005).

Example 4

Adenovirus-Vectored Influenza Rapid-and-Prolonged-Immunologicals-Therapeuticals

The goal of Ad5-vectored influenza RAPIT is to develop an influenza rapid-and-prolonged-immunologic-therapeutic (RAPIT) that can be mass-produced at low costs and mass-administered by non-medical personnel; with the capability to confer rapid/sustained protection against influenza but without the potential to induce drug resistance and reassortment with a wild influenza virus. There is no requirement to propagate an influenza virus and no requirement for needle injection by licensed medical personnel.

It is possible to rapidly generate Ad5-vectored influenza vaccine without growing influenza virus. In an influenza virus, growth varies from strain to strain, some strains are lethal, it is prone to reassortment and mutation events and there is low-titer protection in eggs. In an Ad vector encoding influenza HA, there are more consistent growth rates, the vector is benign, there are no reassortment events, there is high-titer production in PER.C6 cells and a new RCA-free Ad can be generated by the AdHigh system within one month.

Ad5-vectored influenza vaccines in cultured suspension cells may be mass produced. For an Ad-vectored flu vaccine, cloning of influenza HA into Ad does not require growth of influenza virus, a 500-liter wave bioreactor can produce $10^{16}$ Ad particles at one time from PER.C6 suspension cells in serum-free medium, Ad particles can be purified by column chromatography and production of Ad-vectored flu vaccines can be streamlined in rapid response to an escalation in demand (FIG. 11). For a conventional flu vaccine, some influenza virus strains do not grow well in eggs, the average yield is approximately one dose per egg, contamination is more difficult to identify in eggs than in cell cultures, there may be egg-associated allergies and the processing is cumbersome.

Ad5-mediated gene therapy and nasal vaccination may be compared as follows. In gene therapy, a therapeutic protein is expressed from Ad and a biological effect is induced directly by a correct dose of therapeutic protein expressed from Ad in transduced cells. In nasal vaccination, the antigen protein is expressed from Ad, the antigen is presented and an immune response is induced through a cascade of reactions triggered by antigen expressed from Ad in transduced cells. Reports in support of the hypothesis that preexisting immunity to Ad does not interfere with the potency of Ad-vectored nasal vaccines include Shi Z et al. J. Virol. 75: 11474, 2001 (mice), Hoelscher M A et al. Lancet 367: 475, 2006 (mice), Croyle M A et al. PLoS ONE 3: e3548, 2008 (mice), Song K et al. PNAS 107: 22213, 2010 (macaques) and Van Kampen K R et al. Vaccine 23: 1029, 2005 (humans).

The study design of a human phase I clinical trial of an Ad5-vectored nasal avian influenza vaccine was as follows. An AdhVN1203/04.H5 vector encoded HA1+HA2 of the A/VN/1203/04 (H5N1) avian influenza virus. The study was a randomized, double-blind, placebo-controlled, single-site study. There were three cohorts at an escalating dose of $10^8$, $10^9$, and $10^{10}$ vp. The doses were administered by nasal spray and two doses on Days 0 and 28. There was a total of 48 healthy volunteers, aged 19-49. There were sixteen human subjects per dose cohort, including 4 placebo controls per cohort. The cell culture was a RCA free, cell culture based manufacturing in PER.C6 suspension cells in serum-free medium. The adverse events in the respiratory system in 30% or more of subjects included rhinorrhea, nasal irritation, nasal congestion, cough and/or sore throat.

Example 5

Adenovirus Particle as a Broad-Spectrum Rapid-and-Prolonged-Immunologic-Therapeutic (RAPIT) Against Respiratory Pathogens FIG. 15 depicts prophylactic anthrax therapy by intranasal instillation of adenovirus particles shortly before spore challenge.

Methods. AdE (E1/E3-defective Ad5 empty vector without transgene) and AdVAV (E1/E3-defective Ad5 vector encoding Bacillus anthracis protective antigen) particles were intranasally (i.n.) administered dropwise into the nostrils of young (2-month-old) female A/J mice in a volume of 0.05 ml in a single-dose regimen shortly before i.n. challenge with $1\times10^5$ cfu ($\sim25\times LD_{50}$) of Bacillus anthracis Sterne spores. Challenged animals were monitored for survival on a daily basis for 14 days.

Results. AdVAV particles administered 2 days prior to challenge protected 67% of mice against anthrax; AdE particles administered 2 days prior to challenge protected 30% of mice against anthrax; AdE particles administered 1 day prior to challenge protected 22% of mice against anthrax; untreated control mice and mice administered with diluted. AdE particles all succumbed to anthrax within 5 days. AdVAV/–2, AdVAV particles i.n. instilled 2 days prior to challenge at a dose of $1.3\times10^8$ ifu; AdE/–2, AdE particles i.n. instilled 2 days prior to challenge at a dose of $1.3\times10^8$ ifu; AdE*/–2, AdE particles i.n. instilled 2 days prior to challenge at a dose of $1.3\times10^6$ ifu (100-fold dilution in PBS); AdE/–1, ME particles i.n. instilled 1 day prior to challenge at a dose of $1.3\times10^8$ ifu; Control, untreated control mice; numbers in parentheses represent the number of animals in each group.

Significance. Data suggest that AdE or AdVAV particles may confer prophylactic anthrax therapy in a drug-like manner, probably by activating a specific arm of innate immunity that impedes growth of Bacillus anthracis in infected animals, Data suggest that the PA gene expressed from AdVAV may confer synergy with AdE-mediated protection against anthrax. It is conceivable that nasal spray of AdVAV particles may confer more rapid protection against anthrax than other anthrax vaccines during a crisis.

Figure 16:
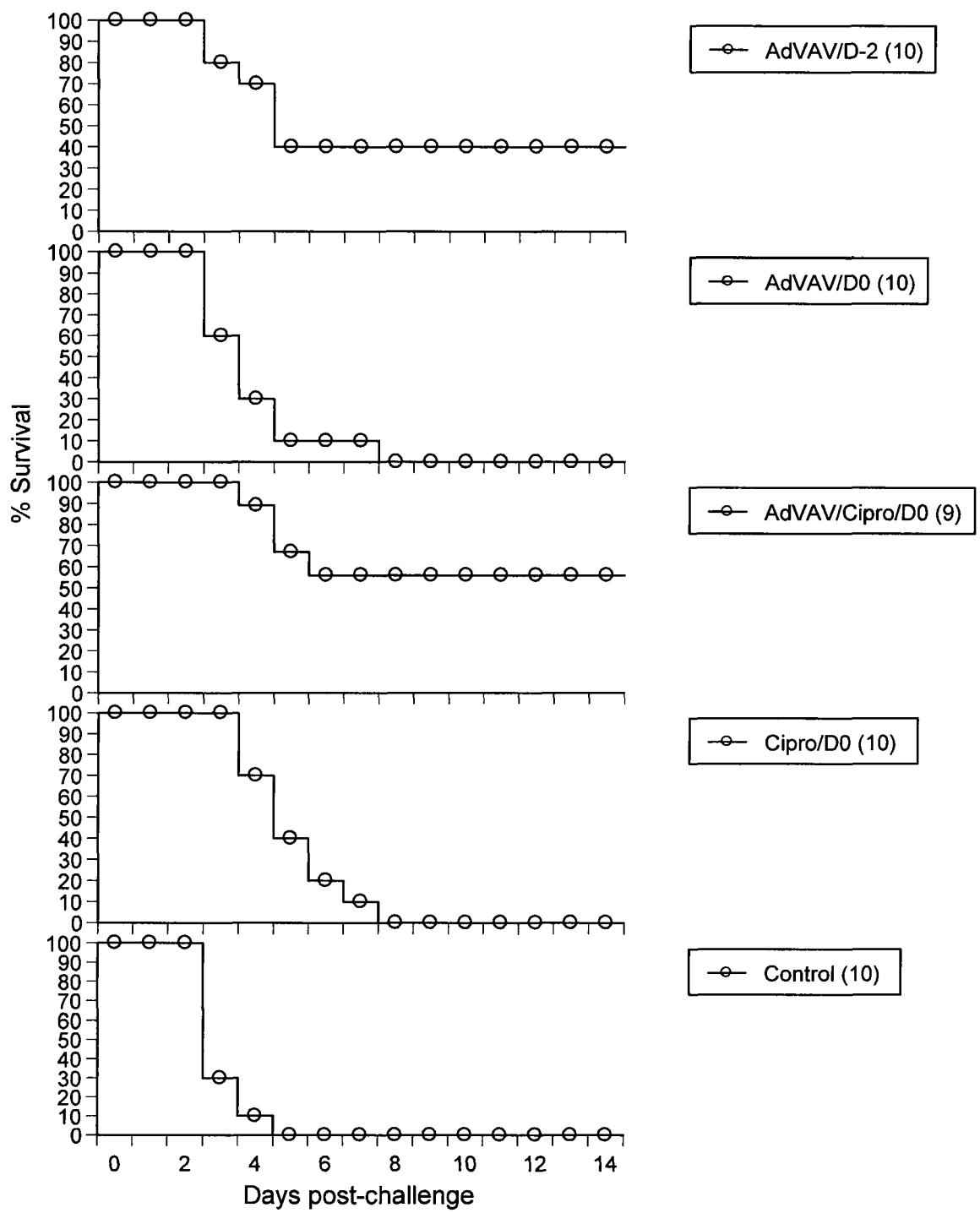

FIG. 16 depicts post-exposure anthrax therapy by i.n. instillation of AdVAV particles.

Methods. AdVAV particles were i.n. administered dropwise into the nostrils of young (2-month-old) female A/J mice in a volume of 0.05 ml in a single-dose regimen, either before or after i.n. challenge with $4\times10^5$ cfu ($\sim100\times LD_{50}$) of Bacillus anthracis Sterne spores. Ciprofloxacin was administered by i.p. injection at a dose of 30 mg/kg (1 injection per day for 2 days; injected 1 and 24 hours post-challenge). Challenged animals were monitored for survival on a daily basis for 14 days.

Results. AdVAV particles administered 2 days prior to challenge protected 40% of mice against anthrax nfirmation of FIGS. 2 and 15 results); AdVAV particles administered 1 hour post-challenge delayed death but failed to improve survival rate; ciprofloxacin injected 1 hour post-challenge also delayed death without success in improving survival rate; AdVAV particles administered in conjunction with ciprofloxacin injection 1 hour post-challenge protected 56% of mice against anthrax; all untreated control mice died within 5 days. AdVAV/D–2, AdVAV particles i.n. instilled 2 days prior to challenge at a dose of $1.3\times10^8$ ifu; AdVAV/D0, AdVAV particles i.n. instilled 1 hour post-challenge at a dose of $1.3\times10^8$ ifu; AdVAV/Cipro/D0, AdVAV particles i.n. instilled 1 hour post-challenge at a dose of $1.3\times10^8$ ifu in conjunction with i.p. injection of ciprofloxacin; Cipro/D0, i.p. injection of ciprofloxacin; Control, untreated control mice without treatments prior to challenge; numbers in parentheses represent the number of animals in each group.

Significance. Data suggest that AdVAV particles may confer post-exposure anthrax therapy in conjunction with antibiotic treatments. Synergy between AdVAV and antibiotics was revealed in this experiment. It is conceivable that nasal spray of AdVAV particles may be able to reduce the requirement for antibiotic use in a post-exposure setting.

Example 6

Adenovirus Particle as a Broad-Spectrum Rapid-and-Prolonged-Immunologic-Therapeutic (RAPIT) Against Respiratory Pathogens Recently, it has been demonstrated that intranasal (i.n.) administration of ΔE1E3 adenovirus type 5 (Ad5) particles, with or without a pathogen antigen encoded in the Ad5 genome, can confer prophylactic therapy against influenza before adaptive immunity is elicited. An Ad5 vector encoding pathogen antigens may thus induce rapid and sustained seamless protection against a pathogen as a drug-vaccine duo (DVD). It has been documented that administration of ΔE1E3 Ad5 particles into mice rapidly induces the production of a wide array of inflammatory cytokines and chemokines including type I interferon (IFN-α and IFN-β); impairs lung dendritic cells; activates natural killer cells; induces production of the antiviral nitric oxide; triggers multifaceted interactions between Ad5 and blood proteins, platelets, macrophages, endothelial cells, and respective parenchymal cells. It is conceivable that multiple reactions induced by the ΔE1E3 Ad5 particles may combine to establish an anti-influenza state in the airway, thus creating a multidimensional defense barrier that can hardly be bypassed by an influenza virus. It is unlikely that influenza is the only disease that can be arrested by Ad5 particles; it is also unlikely that Ad5 particles can counteract all diseases as a panacea. The findings merely show that a single i.n. administration of AdE particles can confer prophylactic therapy against at least a subset of mucosal respiratory pathogens for many weeks in mice and use of the DVD should be unable to induce drug resistance because AdE particles change the habitat in the airway without directly conferring mutational pressure to other viruses. Subsequent elicitation of sustained protective immunity by the DVD's vaccine component fortifies efficacy. The development of a DVD platform will conceivably foster the development of novel clinical strategies in a wide variety of disease settings.

Figure 17:
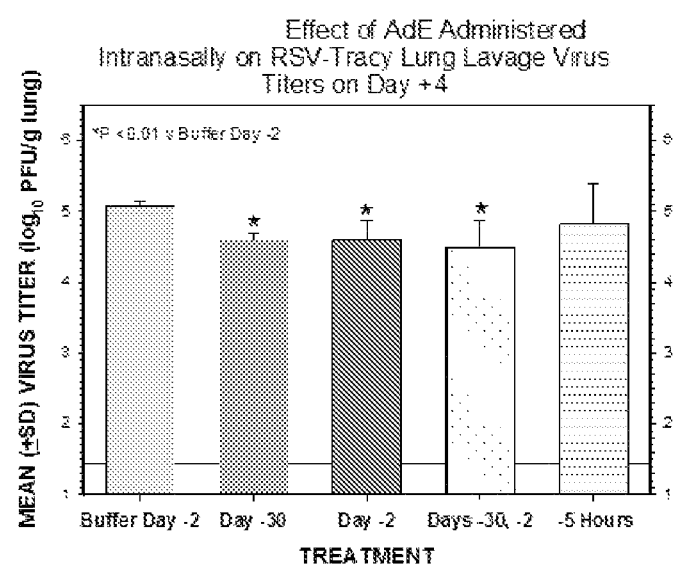

The goal of this Example is to evaluate prophylactic intranasal treatment with Vaxin's AdE (Ad5 empty vector without an RSV transgene) on respiratory syncytial virus (RSV)-infected cotton rats (CR). The endpoints of this study are the demonstration of reduced virus titers in the lung lavage (3 mL) and nasal wash (2 mL) fluids of the infected cotton rats (ca. 60-125 gm in weight) compared to untreated cotton rats. Virus quantification will be done by plaque reduction assay. FIG. 17 depicts the effect of AdE administered intranasally on RSV-Tracy nasal wash as well as lung lavage virus titers on Day +4.

Prophylactic Effectiveness in the RSV-Cotton Rat Model: Cotton Rats (60-125 grn body weight):

Group 1: 6 CR prophylactically (day −2) treated intranasally with vehicle (A195 buffer).

Group 2: 6 CR prophylactically (day −30) treated intranasally with $2.4\times10^8$ ifu of AdE.

Group 3: 6 CR prophylactically (day −2) treated intranasally with $2.4\times10^8$ ifu of AdE.

Group 4: 6 CR prophylactically (days =30 and −2) treated intranasally with $2.4\times10^8$ ifu of AdE during each treatment cycle (primeiboost).

Group 5: 6 CR prophylactically (−5 h) treated intranasally with $2.4\times10^8$ ifu of AdE.

Challenge Virus: RSV-Tracy (P3 w.p. 1/20/12 grown in HEp-2 cells), $2.25\times10^5$ PFU intranasally (100 µL) to cotton rats (60-125 gm) lightly anesthetized with isoflurane. Stock: $2.25\times10^6$ PFU/mL.

AdE vector: Vehicle (A195 buffer) AdE at concentrations of $2.4\times10^9$ are stored at −80° C. Just before use, materials are warmed to room temperature. At least 0.8 mL of each treatment for each group (6 CR/group×0.1 mL of inoculum) is needed. Unused material is kept at −80° C.

Collection of organs and samples. Following euthanasia with $CO_2$, each cotton rat are weighed and the sex and age recorded. The left and one of the large right lobes of the lungs will be removed, rinsed in sterile water to remove external blood contamination and weighed. The left lobe is transpleurally lavaged using 3 mL of Iscove's media with 15% glycerin mixed with 2% FBS-MEM (1:1, v:v) in a 3 mL syringe with a 26 g % needle and injecting at multiple sites to totally inflate the lobe. Lavage fluid is recovered by gently pressing the inflated lobe flat and used to transpleurally lavage the right lobe following the same technique. The lavage fluid is collected and stored on ice until titered. For nasal washes of the upper respiratory tract, the jaws are disarticulated. The head is then be removed and 1 mL of Iscove's media with 15% glycerin mixed with 2% FBS-MEM (1:1, v:1,7) are pushed through each nare (total of 2 mL). The effluent is collected from the posterior opening of the pallet and stored on ice until titered. Samples are not frozen before titration which occurs at the end of sample collecting.

RSV Tracy lung lavage titers (PFU/gm lung) and nasal wash titers (total PFU). Plaque assays are performed using 24-well tissue cultures plates containing nearly confluent monolayers (20 to $40\times10^4$ cells/well) of HEp-2 cells prepared in 10% FCS 24 hr prior to start of assay. At the start of each assay, dilutions (usually serial log 10) are made of the test samples. A 0.2 mL sample of each is then be added to wells in duplicate and allowed to adsorb for 90 min with occasional gentle agitation. After the inoculum is removed, the monolayers is then overlayed with 0.75% methylcellulose in 2% FBS-MEM containing antibiotics, vitamins and other nutrients. Tissue culture and positive virus controls are included in each assay. The plates is placed in a 36° C., 5% $CO_2$ incubator. Day 6±1 day later, plates are stained with 0.1% crystal violet/10% formalin solution (1.5 mL/well) and allowed to sit for 24-48 hr at room temperature. Wells are rinsed with water. Plaques when present are easily visible (clear circles on a very dark blue background). All of the plaques in wells containing between 20 and 80 plaques will be enumerated, averaged and the virus titers calculated as total log 10 PFU for nasal wash fluid or log 10 PFU/g of tissue for lungs or other organs. The lower limit of detection by this method is approximately 1.5 log 10 PFU/g tissue.

Antibody Response to AdE: Blood is collected from the orbital plexus from Groups 2 and 4 (3 CR/group) on day −30 and Groups 2 and 4 (6 CRIgroup) on day −2. Blood will be collected from Groups 1-5 on Day +4. Serums are stored at −20° C.

Reserve samples. Aliquots of nasal wash and lung lavage fluids (Groups 1-5) are saved, stored at −80° C. Serum samples from day +4 are saved, stored at −80° C.

TABLE 6

Proposed plan of study

| Group[1] | Treatment[2] | Route | Volume (mL) | AdE Particles (ifu/CR) | Treatment Schedule | Harvest | Endpoint |
|---|---|---|---|---|---|---|---|
| 1 | Buffer Day −2 | — | 0 | 0 | Day −2 | Day +4 | Virus titer in Lung lavage and nasal wash fluids by PFU |
| 2 | AdE, Day −30 | i.n. | 0.100 | $2.4 \times 10^8$ | Day −2 | | |
| 3 | AdE, Day −2 | i.n. | 0.100 | $2.4 \times 10^8$ | Day −30 | | |
| 4 | AdE, Days −30, −2 | i.n. | 0.100 | $2.4 \times 10^8$ | Days −30 and −2 | | |
| 5 | AdE, −5 Hours | i.n. | 0.100 | $2.4 \times 10^8$ | Hour −5 | | |

Abbreviations:
i.n., intranasal;
PFU, plaque forming units,
[1] N = 6 animals/group; 30 animals total.
[2] All animals to be challenged i.n. (100 μl) with RSV-Tracey (ca. $2.25 \times 10^5$ PFU) on day 0.

TABLE 7

Daily Schedule:

| Wednesday Day −30 Jan. 18, 2012 | Wednesday Day −2 Feb. 15 | Friday Day 0 Feb. 17 | Saturday- Monday Day +1 to +3 | Tuesday Day +4 Feb. 21 | Days +5 to +16 |
|---|---|---|---|---|---|
| Treat Groups 2 and 4 with i.n. AdE; Bleed Groups 2 and 4 (3 CR/gp) | Treat Group 1 with i.n. Vehicle; Groups 3 and 4 with i.n. AdE; Bleed Groups 2 and 4 (6 CR/gp) | At −5 h, treat Group 5 with i.n. AdE At 0 h, infect Groups 1-5 i.n. with RSV-Tracy | Monitor animals | Collect nasal wash and lavage 2 lobes of lungs for virus titers; Collect blood from Groups 1-5 | Monitor titrations for PFU |

Abbreviations: i.n., intranasal; PFU, plaque forming units; gp, group.

Timeline Day 0:
9 am ⇒ Treat group 5 i.n. AdE
2 pm ⇒ Infect all groups
Dosage and Lung and Body Weights on Day +4.

TABLE 8

Lung and Body Weights on Day +4

| Group | Treatment | AdE Dose (ifu/cr) | Lung Lobe Weight (g)[1] Mean | SD | Body Weight (g)[2] Mean | SD |
|---|---|---|---|---|---|---|
| 1 | Buffer Day −2 | 0 | 0.31 | 0.02 | 163.0 | 16.1 |
| 2 | AdE, Day −30 | $2.4 \times 10^8$ | 0.35 | 0.05 | 155.9 | 12.1 |
| 3 | AdE, Day −2 | $2.4 \times 10^8$ | 0.36 | 0.05 | 139.8 | 19.9 |
| 4 | AdE, Days −30, −2 | $2.4 \times 10^8$ | 0.37 | 0.03 | 141.7 | 19.1 |
| 5 | AdE, −5 Hours | $2.4 \times 10^8$ | 0.38 | 0.04 | 146.1 | 8.7 |

[1] There was a statistically significant difference between groups 1 v 3, 4, 5; P = 0.41, 0.011 and 0.004, respectively.
[2] There was a statistically significant difference between groups 1 v 5; P = 0.047.

RSV-Tracy Nasal Wash and Lung Lavage Plaque Reduction Titers:

TABLE 9

RSV-Tracy titers in nasal wash fluids on day +4

| Group | Treatment | RSV titer ($\log_{10}$ total PFU) in cotton rat | | | | | | | | T test/2 | |
| | | A | B | C | D | E | F | Mean | SD | change ($\log_{10}$) | v.Gp 1* |
|---|---|---|---|---|---|---|---|---|---|---|---|
| 1 | Buffer Day −2 | 4.99 | 5.40 | 4.98 | 4.98 | 5.09 | 5.02 | 5.08 | 0.16 | — | — |
| 2 | AdE, Day −30 | 5.04 | 5.09 | 4.86 | 5.07 | 5.00 | 4.69 | 4.96 | 0.16 | −0.12 | 0.230 |
| 3 | AdE, Day −2 | 4.86 | 5.51 | 5.39 | Died | 4.94 | 5.55 | 5.25 | 0.32 | 0.17 | 0.280 |
| 4 | AdE, Days −30, −2 | 5.45 | 5.23 | 4.99 | 5.13 | 5.10 | 5.03 | 5.15 | 0.17 | 0.08 | 0.425 |
| 5 | AdE, −5 Hours | 5.56 | 5.35 | 5.51 | 5.45 | 5.51 | 5.13 | 5.42 | 0.16 | 0.34 | 0.0042 |

*Minimum detection = 0.7 log10 Total PFU. For statistical analysis (Student t test, two tailed) minimum detection (0 plaques) was counted as 0.35 log10 Total PFU. Additional significant P values: Group 5 v 2, 4, P < 0.02.

TABLE 10

RSV-Tracy titers in lung lavage fluids on day +4

| Group | Treatment | RSV titer ($\log_{10}$ PFU/g lung) in cotton rat | | | | | | | | T test/2 | |
|---|---|---|---|---|---|---|---|---|---|---|---|
| | | A | B | C | D | E | F | Mean | SD | Change ($\log_{10}$) v.Gp 1* | |
| 1 | Buffer Day -2 | 5.06 | 5.18 | ** | 5.06 | 5.01 | 5.03 | 5.07 | 0.07 | — | — |
| 2 | AdE, Day -30 | 4.74 | 4.59 | 4.44 | 4.52 | 4.65 | 4.52 | 4.58 | 0.11 | -0.49 | 0.000010 |
| 3 | AdE, Day -2 | 5.03 | 4.26 | 4.60 | Died | 4.60 | 4.49 | 4.60 | 0.28 | -0.47 | 0.0063 |
| 4 | AdE, Days -30, -2 | 3.95 | 5.01 | 4.14 | 4.54 | 4.65 | 4.68 | 4.49 | 0.39 | -0.57 | 0.0098 |
| 5 | AdE, -5 Hours | 5.02 | 5.34 | 4.53 | 3.88 | 5.45 | 4.65 | 4.81 | 0.59 | -0.26 | 0.357 |

*Minimum detection = 1.3 log10/g lung.
**There were no plaques although there was virus in the nasal fluid. Therefore, it was assumed that the lungs were not infected or technical error. Did not include in there data for analysis. For Statistical analysis (Student t test, two-tailed) minimal detection (0 plaques) was counted as 1.1 log10/g lung. There was no additional significant P values.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

SPECIFIC EMBODIMENTS

Specific Embodiment A: A method for inducing a rapid and prolonged protective response against respiratory pathogens in a mammalian subject in need thereof comprising administering intranasally an effective amount of at least $10^7$ infectious units (ifu) of E1 and/or E3 deleted adenovirus, with or without encoding a pathogen-derived antigen, wherein the protective immune response begins within about five hours of administration and lasts at least 45 days if an influenza virus-derived antigen is not included.

Specific Embodiment B: The method of Specific Embodiment A, wherein the respiratory pathogen is a virus.

Specific Embodiment C: The method of Specific Embodiment B, wherein the virus is an influenza virus, a respiratory syncytial virus (RSV), a common cold virus or a measles virus.

The method of Specific Embodiment C, wherein the common cold virus is a rhinovirus or a coronavirus.

Specific Embodiment D: The method of Specific Embodiment A, wherein the respiratory pathogen is a bacterium.

Specific Embodiment E: The method of Specific Embodiment D, wherein the bacterium is selected from the group consisting of *Bacillus, Mycobacterium, Staphylococcus, Streptococcus, Pseudomonas, Klebsiella, Haemophilus,* and *Mycoplasma.*

The method of Specific Embodiment E, wherein the bacterium is *Bacillus anthracis.*

Specific Embodiment F: The method of Specific Embodiment A, wherein the respiratory pathogen is a fungus.

The method of Specific Embodiment A, wherein the fungus is *Aspergillus.*

The method of Specific Embodiment A, wherein the effective amount is at least $10^7$ infectious units (ifu) of E1 and/or E3 deleted adenovirus.

The method of Specific Embodiment A, wherein the effective amount is at least $10^8$ infectious units (ifu) of E1 and E3 deleted or disrupted empty adenovirus.

The method of Specific Embodiment A, wherein the effective amount is at least $10^9$ infectious units (ifu) of E1 and E3 deleted or disrupted empty adenovirus.

The method of Specific Embodiment A wherein the subject in need thereof is an adult.

The method of Specific Embodiment A wherein the subject in need thereof is a child.

The method of Specific Embodiment A wherein the subject in need thereof is an immunocompromised patient.

Specific Embodiment G: The method of Specific Embodiment A comprising at least two steps of administering.

The method of Specific Embodiment G wherein the administering is about 40 days apart, about 41 days apart, about 42 days apart, about 43 days apart, about 44 days apart, about 45 days apart, about 46 days apart, about 47 days apart, about 48 days apart, about 49 days apart or about 50 days apart.

The method of Specific Embodiment A wherein the adenovirus is a human adenovirus.

The method of Specific Embodiment A wherein the adenovirus is a bovine adenovirus, a canine adenovirus, a non-human primate adenovirus, a chicken adenovirus, or a porcine or swine adenovirus.

What is claimed is:

1. A method of inducing a therapeutic innate immune response against a coronavirus in a mammalian subject in need thereof, comprising selecting a mammalian subject in need of reduced severity of coronavirus infection as the mammalian subject in need of the therapeutic innate immune response against coronavirus:
   administering intranasally to the mammalian subject at least $10^8$ viral particles (vp) of an E1 and E3 deleted human adenovirus, without encoding any heterologous antigen to the adenovirus,
   wherein the at least $10^8$ viral particles (vp) administered intranasally is an effective amount for inducing the therapeutic innate immune response against the coronavirus in the mammalian subject.

2. The method of claim 1, wherein the therapeutic innate immune response begins within about twenty-four hours of intranasal administration and lasts at least about 21 days, whereby the method is a method of inducing a therapeutic innate immune response in an mammalian subject in need thereof within about twenty-four hours of intranasal administration that lasts at least about 21 days.

3. The method of claim 1, wherein the coronavirus is a severe acute respiratory syndrome-associated coronavirus.

4. The method of claim 1, wherein the therapeutic innate immune response begins within twenty-four hours of intranasal administration, whereby the method is a method of inducing a therapeutic innate immune response within 24 hours of intranasal administration.

5. The method of claim 1, wherein the therapeutic innate immune response lasts about 47 days, whereby the method is a method of inducing a therapeutic innate immune response that lasts about 47 days.

6. The method of claim 1, wherein the subject in need thereof is an adult, whereby the method is a method of inducing a therapeutic innate immune response in an adult mammalian subject in need thereof.

7. The method of claim 1, wherein the at least $10^8$ vp of the E1 and E3 deleted human adenovirus is administered to the mammalian subject prior to exposure to the severe acute respiratory syndrome-associated coronavirus, whereby the method is a method of inducing a therapeutic innate immune response against a severe acute respiratory syndrome-associated coronavirus in a mammalian subject in need thereof prior to exposure to the severe acute respiratory syndrome-associated coronavirus.

8. The method of claim 1, wherein the at least $10^8$ vp of the E1 and E3 deleted human adenovirus is administered to the mammalian subject post exposure to the severe acute respiratory syndrome-associated coronavirus, whereby the method is a method of inducing a therapeutic innate immune response against a severe acute respiratory syndrome-associated coronavirus in a mammalian subject in need thereof after exposure to the severe acute respiratory syndrome-associated coronavirus.

9. The method of claim 1, wherein the at least $10^8$ vp of the E1 and E3 deleted human adenovirus induces a mucosal innate immune response, whereby the method is a method of inducing a therapeutic innate immune response and a mucosal innate immune response against a severe acute respiratory syndrome-associated coronavirus in a mammalian subject in need thereof.

10. The method of claim 1, wherein the at least $10^8$ vp of the E1 and E3 deleted human adenovirus is at least $10^9$ vp of E1 and E3 deleted human adenovirus or at least $10^{10}$ vp of E1 and E3 deleted human adenovirus.

11. The method of claim 1, wherein the coronavirus is a common cold virus.

* * * * *

SEQUENCE LISTING

<160> NUMBER OF SEQ ID NOS: 2

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cacaggtacc gccaccatga aggccaagct g                                31

```
<210> SEQ ID NO 2
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gagtctagat tatcagccga acaggcctct gctctgg                              37
```